United States Patent [19]

Tsai et al.

[11] Patent Number: 5,830,760
[45] Date of Patent: Nov. 3, 1998

[54] CREATING NOVEL HEMATOPOIETIC CELL LINES BY EXPRESSING ALTERED RETINOIC ACID RECEPTORS

[75] Inventors: Schickwann Tsai, Redmond; Steven J. Collins, Seattle, both of Wash.

[73] Assignee: Fred Hutchinson Cancer Research Center, Seattle, Wash.

[21] Appl. No.: 592,383

[22] PCT Filed: Jul. 28, 1994

[86] PCT No.: PCT/US94/08450

§ 371 Date: Jan. 26, 1996

§ 102(e) Date: Jan. 26, 1996

[87] PCT Pub. No.: WO95/04143

PCT Pub. Date: Feb. 9, 1995

Related U.S. Application Data

[63] Continuation-in-part of Ser. No. 99,242, Jul. 28, 1993, abandoned.

[51] Int. Cl.$^6$ ............................................. C12N 5/16
[52] U.S. Cl. ........................ 435/377; 435/69.1; 435/325
[58] Field of Search ............................ 435/69.1, 240.2, 435/240.21, 325, 377

[56] References Cited

PUBLICATIONS

Breitman, T.R., S.E. Selonick, and S.J. Collins. 1980. Induction of differentiation of the human promyelocytic leukemia cell line (HL–60) by retinoic acid. *Proc. Natl. Acad. Sci. USA* 77: 2936–2940.

Collins, S.J., R.C. Gallo, and R.E. Gallagher. 1977. Continuous growth and differentiation of human myeloid leukemia cells in suspension culture. *Nature* 270; 347–349.

Collins, S.J., K. Robertson, and L. Mueller. 1990. Retinoic acid–induced granulocyte differentiation of HL–60 myeloid leukemia cells is mediated directly through the retinoic acid receptor (RAR–α). *Mol. Cell. Biol.* 10:2154–2161.

Denburg, J.A. 1992. Basophil and mast cell lineages *in vitro* and *in vivo*. *Blood* 79: 846–860. (A review).

deThe, H., A. Marchio, P. Tiollais, and A. Dejean. 1989. Differential expression and ligand regulation of the retinoic acid receptor α and α' genes. *EMBO J.* 8: 429–433.

deThe, H., M. Vivanco–Ruiz, P. Tiollais, H. Stunnenberg, and A. Dejean. 1990. Identification of a retinoic acid responsive element in the retinoic acid receptor α gene. *Nature* 343: 177–180.

deThe, H., C. Chomienne, M. Lanotte, L. Degos, and A. Dejean. 1990. The t(15:17) translocation of acute promelocytic leukemia fuses the retinoic acid receptor α gene to a novel transcribed locus. *Nature* 347: 558–561.

Evans, R. 1988. The steroid and thyroid hormone receptor superfamily. *Science* 240: 889–895.

Gallagher, R., F. Said, I. Pua, P. Papenhausen, E. Paietta, and P. Wiernik. 1989. Expression of retinoic acid receptor α in human luekemia cells with variable responsiveness to retinoic acid. *Leukemia* 3: 789–795.

Gigure, V., E. Ong, P. Segui, and R. Evans. 1987. Identification of a receptor for the morphogen retinoic acid. *Nature* 330: 624–629.

Heyworth, C.M., T.M. Dexter, O. Kan ,and A.D. Whetton. 1990. *Growth Factors* 2: 197–211.

Largman, C., K. Detmer, J. Corral, F. Hack, and H. Lawrence. 1989. Expression of retinoic acid receptor alpha mRNA in human leukemic cells. *Blood* 74: 99–102.

Lotan, R. 1980. Effects of vitamin A and its analogs (retinoids) on normal and neoplastic cells. *Biochem. Biophys. Acta* 605 : 33–91.

Spooncer, E.C., Boettingen, D. and T.M. Dexter. 1984. *Nature* 310: 228–230.

Spooncer, E., C. Heyworth, A. Dunn, and T.M. Dexter. 1986. Self–renewal and differentiation of interleukin–3–dependent multipotent stem cells are modulated by stromal cells and serum factors. *Differentiation* 31: 111–118.

Tsai, S., S. Bartelmez, R. Heyman, K. Damm, R. Evans and S.J. Collins. 1992. *Genes & Development* 6: 2258–2269.

Tsai, S.–F., D. Martin, L. Zon, A. D'Andrea, G. Wong, and S. Orkin. 1989. Cloning of cDNA for the major DNA–binding protein of the erythroid lineage through expression in mammalian cells. *Nature* 339: 446–451.

Umesono, K., V. Giguere, C. Glass, M. Rosenfeld, and R. Evans. 1988. Retinoic acid and thyroid hormone induce gene expression through a common responsive element. *Nature* 336: 262–265.

Zon, I.L., M.F. Gurish, R. Stevens, C. Mather, D.S. Reynolds, K.F. Austen, and S.H. Orkin. 1991. GATA–binding transcription factors in mast cells regulate the promoter of the mast cell carboxypeptidase A gene. *J. Biol. Chem.* 266: 22948–22953.

Tsai, S., and S.J. Collins. Aug. 1993. A dominant negative retinoic acid recept blocks neutrophil differentiation at the promyelocyte stage. *Proc. Natl. Acad. Sci. USA* 90: 7153–7157.

Tsai, S., et al. , "Lymphohematopoietic progenitors immortalized by a retroviral vector harboring a dominant–negative retinoic acid receptor can racapitulate lymphoid, myeloid, and erythroid development," *Genes and Development,* 8:2831–2841, 1994.

*Primary Examiner*—Stephen Walsh
*Assistant Examiner*—Michael D. Pak
*Attorney, Agent, or Firm*—Christensen O'Connor Johnson & Kindness PLLC

[57] ABSTRACT

Methods for establishing continuous SCF dependent lympho-hematopoietic progenitor cell lines capable of differentiating into erythroid, myeloid, and B lymphocytic lineages, and GM-CSF dependent neutrophil progenitor cell lines capable of differentiating into neutrophils but not into monocytes, mast cells, or basophils, by introducing into bone marrow, fetal spleen, fetal liver, or other hematopoietic myeloid cells nucleic acid encoding a dominant negative suppressor of a retinoic acid receptor-alpha and a selectable marker, and culturing the recombinant cells in culture medium containing SCF or GM-CSF, agents allowing for selective growth of the recombinant cells, and a level of retinoic acid of less than about $10^{-8}$M to about $10^{-9}$M in the case of establishing neutrophilic progenitor cell lines. Addition of a retinol compound induces the latter cell line to differentiate into neutrophils.

12 Claims, 35 Drawing Sheets

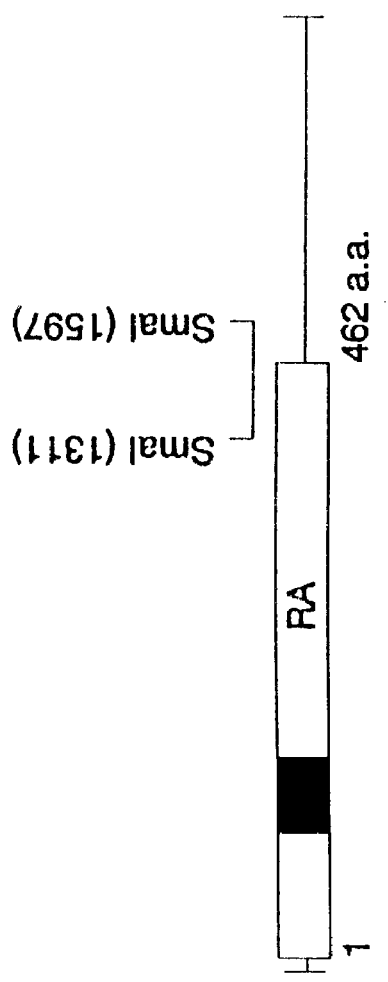
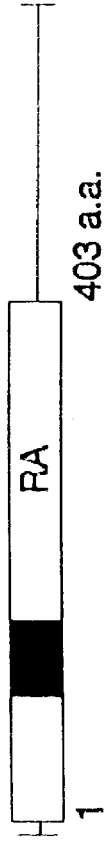
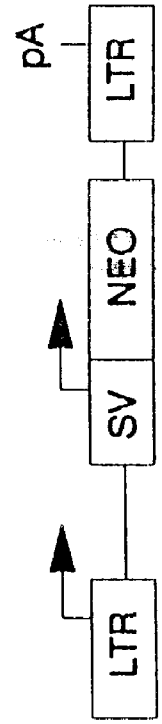
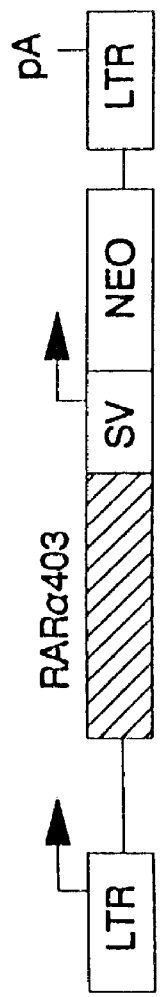
Fig. 1A. A. RARα
Fig. 1B. B. RARα403
Fig. 1C. C. LXSN
Fig. 1D. D. LRARα403SN

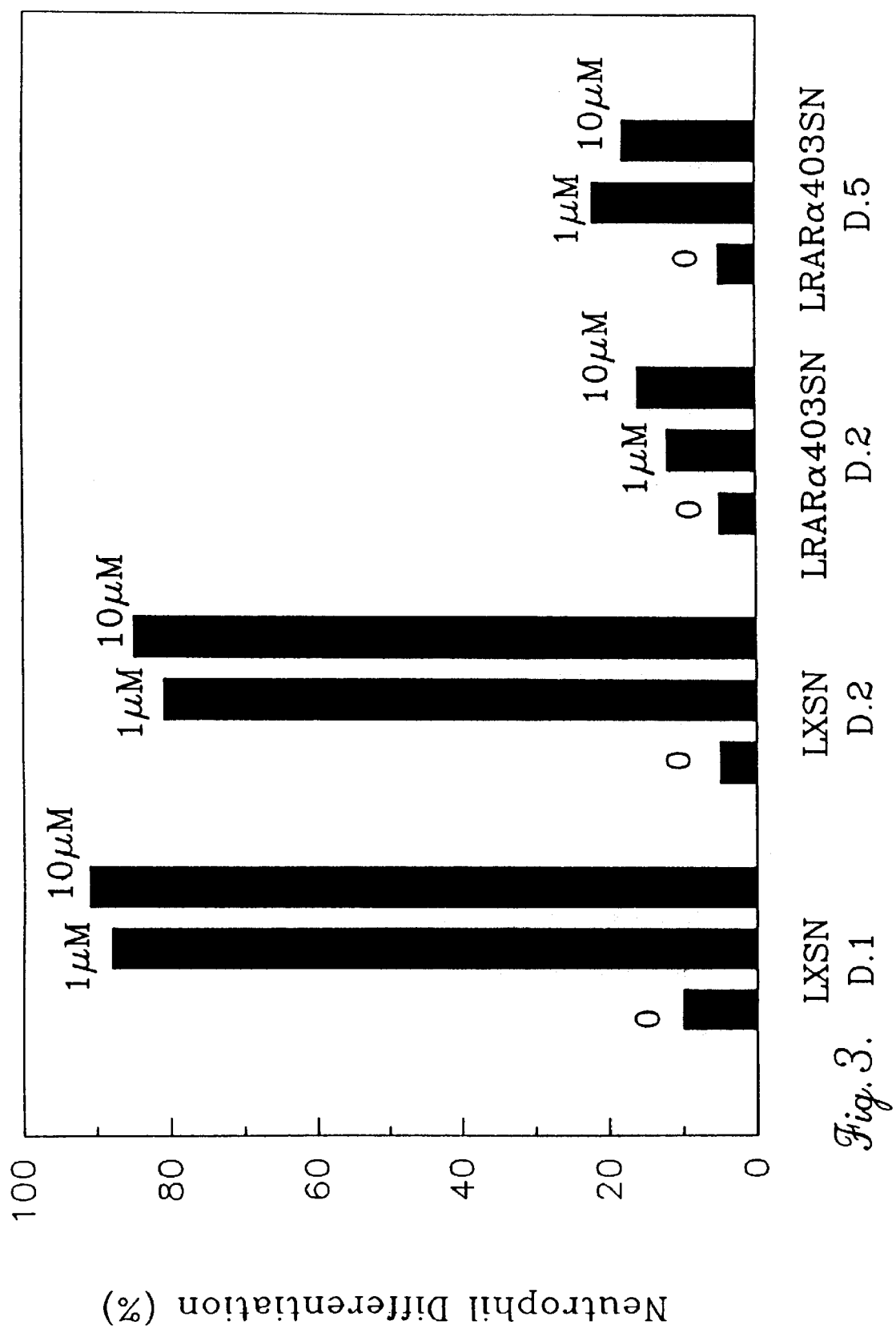

A. Normal RARα

B. RARα Suppressed

Fig. 16B.

```
  1 GCCATCTGGGGCCCAGGCCCCATGCCCCGAGGAGGGTGGTCTGAAGCCCACCAGAGCCCCCTGCCAGACTGTCTGCCTCCCTTCTGACTG
                         1                                         21
 91 TGGCCGCTTGGCATGGCCAGCAACAGCAGTCCTGCCCGACACCTGGGGCGGGCACTCAATGGTTACCCGGTGCCTCCCTACGCCTTC
      MetAlaSerAsnSerSerCysProThrProGlyGlyHisLeuAsnGlyTyrProValProProTyrAlaPhe
                                          31                                        51
181 TTCTTCCCCCCTATGCTGGGTGGACTCTCCCCGGCGCTCTCCAGCACTCTCCAGCTTCCAGTTAGTGGATATAGCACCA
    PhePheProProMetLeuGlyLeuSerProProGlyAlaLeuThrThrLeuGlnHisGlnLeuProValSerGlyTyrSerThrPro
                      61                                        81
271 TCCCCAGCCACCATTGAGACCCAGCAGTTCTGAAGAGATAGTGCCCAGCCCTCCCTCGCCACCCCTCTACCCGCATCTACAAG
    SerProAlaThrIleGluThrGlnSerSerSerGluIleValProSerProProProLeuProProArgIleTyrLys
                          91                                        111
361 CCTGCTTTGTCTGCAGGACAAGTCCTCAGCTACCACTATGGGTGCCTGTGAGGGCTTCTTCCGCCGCAGCATC
    ProCysPheValCysGlnAspLysSerSerSerGlyTyrHisTyrGlyCysLysGlyPheArgArgSerIle
                          121                                        141
451 CAGAAGAACATGGTGTACACGTGTCACCGGGACAAGAACTGCATCATCAACAAGGTGACCCGGAACCGCTGCCAGTACTGCCGACTGCAG
    GlnLysAsnMetValTyrThrCysHisArgAspLysAsnCysIleIleAsnLysValThrArgAsnArgCysGlnTyrCysArgLeuGln
                          151                                        171
541 AAGTGCTTTGAAGTGGGCATGTCCAAGGAGTCTGTCAGGAATGACAGAAACAAGAAGAAGAAGGAGGTGCCCAAGCCCGAGTGCTCTGAG
    LysCysPheGluValGlyMetSerLysGluSerValArgAsnAspArgAsnLysLysLysLysGluValProLysProGluCysSerGlu
                          181                                        201
631 AGCTACACGCTGACGCCGGAGGTGGGGGAGCTCATTGAGAAGGTGCGCAAAGCGCACCAGGAAACCTTCCCTGCCCTGTGCCAGCTGGGC
    SerTyrThrLeuThrProGluValGlyGluLeuIleGluLysValArgLysAlaHisGlnGluThrPheProAlaLeuCysGlnLeuGly
                          211                                        231
721 AAATACACTACGAACAACAGCTCAGAACAACGTGTCTCTCTGGACATTGACCTGTGGGACAAGTTCAGTGAACTCTCCACCAAGTGCATC
    LysTyrThrThrAsnAsnSerSerGluGlnArgValSerLeuAspIleAspLeuTrpAspLysPheSerGluLeuSerThrLysCysIle
                          241                                        261
    IleLysThrValGluPheAlaLysGlnLeuProGlyPheThrThrLeuThrIleAlaAspGlnIleThrLeuLeuLysAlaAlaCysLeu
```

Fig. 16E.

2071 AAGGAATTTGTGCTGTGTATTGGGGAGCTGGATCCAGAGCTGGAGGGGTGGCTCCGGGGAGGAGTGGCTCGGAAGGGCCCCCAC
2161 TCTCCTTTCATGTCCCTGCCCCTCCCCTGCCCCTCCCCAGTTCTCCTCCTCAGCCTTTCTCTTTAAAACTGTGAAGTACTAACTTTCC
2251 AAGGCCTGCCTTCCCCTCCCCACTGGAGAAGCCGCCAGCCCCTTTCTCCTGCCTGACCACTGGGTGTGGACGGTGTGGGGCAGC
2341 CCTGAAAGGACAGGCTCCTGGCCTTGCCTGCACCCATGAGGCATGAGAGCAGGGCAAGGGCCCCGGGACAGAGTTT
2431 TCCCAGACCTGGCTCCTCGGCAGAGCTGCCTCCCGTCAGGCTCAGCCACCAGACTCATCTAGGCTCCCCAGCTGTGAAGGGCTGGCCAGG
2521 GGCCCGAGCTGCCCCCACCCCCAGCCTCAGCCACCAGACCCCCAGACACCACACATGCGCGTGCGCACACACAA
2611 ACACACACACTGGACAGTAGATGGGCCGACACACTTGGCCCGAGTTCCTCCATTTCCCTGCCTGCCCCCACCCCCAACCTGTCC
2701 CACCCCCGTGCCCCCTCCTTACCCCGCAGGACGGGCTCTCCCCGTGGGTCTCCCCTGCACCCCCAGCTGGGGGAGCTGGCTCTG
2791 CCCCGACCTCCTTCACCAGGGGTTGGGGCCCCTTGGGGCCCCTGGAGCCCGCACCTGTTACTGTGTTGGGCTTTCCACTGAGATCTACTG
2881 GATAAAGAATAAAGTTCTATTTATTCTAAAAAAAAAAAAAAAAAAAAAA

*Fig. 16D.*

| SCF | + | + | + | + |
|---|---|---|---|---|
| IL-3 | − | − | + | + |
| RA ($10^{-5}$M) | − | + | − | + |
| *Exp. 1 (n=2)* | | | | |
| Total Cells on Day 3 (x$10^6$) | 2.0 | 0.6 | 3.9 | 3.1 |
| Total CFU-GM | 2.5 | 0 | 1,115 | 32,040 |
| Total SCF-supported clonogenic cells | 5,200 | 1,000 | 7,400 | 2,000 |
| *Exp. 2 (n=3)* | | | | |
| Total cells on day 4 (x$10^6$) | 7.0 | ND | 17.4 | 13.3 |
| Total CFU-GM | 0 | ND | 150 | 12,850 |
| Total SCF-supported clonogenic cells | 58,600 | ND | 68,600 | 8,600 |
| Total BFU-E | 182,800 | ND | 276,000 | 42,800 |

*Fig. 17.*

Ig C$_{\mu 3}$ probe

RAG-1 probe

β-Globin Probe

| | | | | |
|---|---|---|---|---|
| EML C1 | EML C1 + W20 + IL-7 x 8d | EML C1 + W20 + IL-7 x17d | EPRO C1 | W20 |
| 1 | 2 | 3 | 4 | 5 |

Neo Probe

Fig. 24E.

SEQUENCE LISTING ( 1 ) GENERAL INFORMATION:

( i i i ) NUMBER OF SEQUENCES:10

( 2 ) INFORMATION FOR SEQ ID NO:1:

( i ) SEQUENCE CHARACTERISTICS:
        ( A ) LENGTH:2940 base pairs
        ( B ) TYPE:nucleic acid
        ( C ) STRANDEDNESS:double
        ( D ) TOPOLOGY:linear ( i i ) MOLECULE TYPE:cDNA to mRNA
        ( A ) DESCRIPTION:see Figure 16B; RAR- alpha ( v i i ) IMMEDIATE SOURCE:
        ( A ) LIBRARY:cDNA ( i x ) SEQUENCE DESCRIPTION: SEQ ID NO:1:

```
GCCATCTGGG  CCCAGGCCCC  ATGCCCCGAG  GAGGGGTGGT  CTGAAGCCCA  CCAGAGCCCC      60
CTGCCAGACT  GTCTGCCTCC  CTTCTGACTG  TGGCCGCTTG  GCATGGCCAG  CAACAGCAGC     120
TCCTGCCCGA  CACCTGGGGG  CGGGCACCTC  AATGGGTACC  CGGTGCCTCC  CTACGCCTTC     180
TTCTTCCCCC  CTATGCTGGG  TGGACTCTCC  CCGCCAGGCG  CTCTGACCAC  TCTCCAGCAC     240
CAGCTTCCAG  TTAGTGGATA  TAGCACACCA  TCCCCAGCCA  CCATTGAGAC  CCAGAGCAGC     300
AGTTCTGAAG  AGATAGTGCC  CAGCCCTCCC  TCGCCACCCC  CTCTACCCCG  CATCTACAAG     360
CCTTGCTTTG  TCTGTCAGGA  CAAGTCCTCA  GGCTACCACT  ATGGGGTCAG  CGCCTGTGAG     420
GGCTGCAAGG  GCTTCTTCCG  CCGCAGCATC  CAGAAGAACA  TGGTGTACAC  GTGTCACCGG     480
GACAAGAACT  GCATCATCAA  CAAGGTGACC  CGGAACCGCT  GCCAGTACTG  CCGACTGCAG     540
AAGTGCTTTG  AAGTGGGCAT  GTCCAAGGAG  TCTGTGAGAA  ACGACCGAAA  CAAGAAGAAG     600
AAGGAGGTGC  CCAAGCCCGA  GTGCTCTGAG  AGCTACACGC  TGACGCCGGA  GGTGGGGGAG     660
CTCATTGAGA  AGGTGCGCAA  AGCGCACCAG  GAAACCTTCC  CTGCCCTCTG  CCAGCTGGGC     720
AAATACACTA  CGAACAACAG  CTCAGAACAA  CGTGTCTCTC  TGGACATTGA  CCTCTGGGAC     780
AAGTTCAGTG  AACTCTCCAC  CAAGTGCATC  ATTAAGACTG  TGGAGTTCGC  CAAGCAGCTG     840
CCCGGCTTCA  CCACCCTCAC  CATCGCCGAC  CAGATCACCC  TCCTCAAGGC  TGCCTGCCTG     900
GACATCCTGA  TCCTGCGGAT  CTGCACGCGG  TACACGCCCC  AGCAGGACAC  CATGACCTTC     960
TCGGACGGGC  TGACCCTGAA  CCGGACCCAG  ATGCACAACG  CTGGCTTCGG  CCCCCTCACC    1020
GACCTGGTCT  TTGCCTTCGC  CAACCAGCTG  CTGCCCCTGG  AGATGGATGA  TGCGGAGACG    1080
GGGCTGCTCA  GCGCCATCTG  CCTCATCTGC  GGAGACCGCC  AGGACCTGGA  GCAGCCGGAC    1140
CGGGTGGACA  TGCTGCAGGA  GCCGCTGCTG  GAGGCGCTAA  AGGTCTACGT  GCGGAAGCGG    1200
AGGCCCAGCC  GCCCCCACAT  GTTCCCCAAG  ATGCTAATGA  AGATTACTGA  CCTGCGAAGC    1260
ATCAGCGCCA  AGGGGGCTGA  GCGGGTGATC  ACGCTGAAGA  TGGAGATCCC  GGGCTCCATG    1320
CCGCCTCTCA  TCCAGGAAAT  GTTGGAGAAC  TCAGAGGGCC  TGGACACTCT  GAGCGGACAG    1380
CCGGGGGGTG  GGGGCGGGA   CGGGGGTGGC  CTGGCCCCCC  CGCCAGGCAG  CTGTAGCCCC    1440
AGCCTCAGCC  CCAGCTCCAA  CAGAAGCAGC  CCGGCACCC   ACTCCCGTG   ACCGCCACG     1500
CCACATGGAC  ACAGCCCTCG  CCCTCCGCCC  CGGCTTTTCT  CTGCCTTTCT  ACCGACCATG    1560
TGACCCCGCA  CCAGCCCTGC  CCCCACCTGC  CCTCCGGGC   AGTACTGGG   ACCTTCCTG     1620
GGGGACGGGG  AGGGAGGAGG  CAGCGACTCC  TTGGACAGAG  GCCTGGGCCC  TCAGTGGACT    1680
```

| | | | | | |
|---|---|---|---|---|---|
| GCCTGCTCCC | ACAGCCTGGG | CTGACGTCAG | AGGCCGAGGC | CAGGAACTGA | GTGAGGCCCC | 1740 |
| TGGTCCTGGG | TCTCAGGATG | GGTCCTGGGG | GCCTCGTGTT | CATCAAGACA | CCCCTCTGCC | 1800 |
| CAGCTCACCA | CATCTTCATC | ACCAGCAAAC | GCCAGGACTT | GGCTCCCCA | TCCTCAGAAC | 1860 |
| TCACAAGCCA | TTGCTCCCCA | GCTGGGGAAC | CTCAACCTCC | CCCTGCCTC | GGTTGGTGAC | 1920 |
| AGAGGGGGTG | GGACAGGGGC | GGGGGGTTCC | CCCTGTACAT | ACCCTGCCAT | ACCAACCCCA | 1980 |
| GGTATTAATT | CTCGCTGGTT | TTGTTTTTAT | TTTAATTTTT | TTGTTTTGAT | TTTTTAATA | 2040 |
| AGAATTTTCA | TTTTAAGCAC | ATTTATACTG | AAGGAATTTG | TGCTGTGTAT | TGGGGGAGC | 2100 |
| TGGATCCAGA | GCTGGAGGGG | GTGGGTCCGG | GGGAGGGAGT | GGCTCGGAAG | GGGCCCCAC | 2160 |
| TCTCCTTTCA | TGTCCCTGTG | CCCCCCAGTT | CTCCTCCTCA | GCCTTTCCT | CCTCAGTTTT | 2220 |
| CTCTTTAAAA | CTGTGAAGTA | CTAACTTTCC | AAGGCCTGCC | TTCCCTCCC | TCCCACTGGA | 2280 |
| GAAGCCGCCA | GCCCCTTTCT | CCCTCTGCCT | GACCACTGGG | TGTGGACGGT | GTGGGCAGC | 2340 |
| CCTGAAAGGA | CAGGCTCCTG | GCCTTGGCAC | TTGCCTGCAC | CCACCATGAG | GCATGGAGCA | 2400 |
| GGGCAGAGCA | AGGGCCCCGG | GACAGAGTTT | TCCAGACCT | GGCTCCTCGG | CAGAGCTGCC | 2460 |
| TCCCGTCAGG | GCCCACATCA | TCTAGGCTCC | CCAGCCCCA | CTGTGAAGGG | GCTGGCCAGG | 2520 |
| GGCCCGAGCT | GCCCCCACCC | CCGGCCTCAG | CCACCAGCAC | CCCCATAGGG | CCCCCAGACA | 2580 |
| CCACACACAT | GCGCGTGCGC | ACACACACAA | ACACACACAC | ACTGGACAGT | AGATGGGCCG | 2640 |
| ACACACACTT | GGCCCGAGTT | CCTCCATTTC | CCTGGCCTGC | CCCCCACCCC | CAACCTGTCC | 2700 |
| CACCCCCGTG | CCCCCTCCTT | ACCCCGCAGG | ACGGGCCTAC | AGGGGGGTCT | CCCCTCACCC | 2760 |
| CTGCACCCCC | AGCTGGGGGA | GCTGGCTCTG | CCCCGACCTC | CTTCACCAGG | GGTTGGGGCC | 2820 |
| CCTTCCCCTG | GAGCCCGTGG | GTGCACCTGT | TACTGTTGGG | CTTTCCACTG | AGATCTACTG | 2880 |
| GATAAAGAAT | AAAGTTCTAT | TTATTCTAAA | AAAAAAAAA | AAAAAAAAA | AAAAAAAAA | 2940 |

(2) INFORMATION FOR SEQ ID NO:2:

(i) SEQUENCE CHARACTERISTICS:
        (A) LENGTH: 462 amino acids
        (B) TYPE: amino acid
        (C) STRANDEDNESS: single
        (D) TOPOLOGY: linear (ii) MOLECULE TYPE: polypeptide
        (A) DESCRIPTION: sequence encoded by SEQ. ID. NO. 1

(ix) SEQUENCE DESCRIPTION: SEQ ID NO:2:

```
Met  Ala  Ser  Asn  Ser  Ser  Ser  Cys  Pro  Thr  Pro  Gly  Gly  Gly  His
                     5                   10                      15

Leu  Asn  Gly  Tyr  Pro  Val  Pro  Pro  Tyr  Ala  Phe  Phe  Phe  Pro  Pro
                    20                   25                      30

Met  Leu  Gly  Gly  Leu  Ser  Pro  Pro  Gly  Ala  Leu  Thr  Thr  Leu  Gln
                    35                   40                      45

His  Gln  Leu  Pro  Val  Ser  Gly  Tyr  Ser  Thr  Pro  Ser  Pro  Ala  Thr
                    50                   55                      60

Ile  Glu  Thr  Gln  Ser  Ser  Ser  Ser  Glu  Glu  Ile  Val  Pro  Ser  Pro
                    65                   70                      75

Pro  Ser  Pro  Pro  Pro  Leu  Pro  Arg  Ile  Tyr  Lys  Pro  Cys  Phe  Val
                    80                   85                      90

Cys  Gln  Asp  Lys  Ser  Ser  Gly  Tyr  His  Tyr  Gly  Val  Ser  Ala  Cys
                    95                  100                     105

Glu  Gly  Cys  Lys  Gly  Phe  Phe  Arg  Arg  Ser  Ile  Gln  Lys  Asn  Met
                   110                  115                     120
```

| Val | Tyr | Thr | Cys | His<br>125 | Arg | Asp | Lys | Asn | Cys<br>130 | Ile | Ile | Asn | Lys | Val<br>135 |
|---|---|---|---|---|---|---|---|---|---|---|---|---|---|---|
| Thr | Arg | Asn | Arg | Cys<br>140 | Gln | Tyr | Cys | Arg | Leu<br>145 | Gln | Lys | Cys | Phe | Glu<br>150 |
| Val | Gly | Met | Ser | Lys<br>155 | Glu | Ser | Val | Arg | Asn<br>160 | Asp | Arg | Asn | Lys | Lys<br>165 |
| Lys | Lys | Glu | Val | Pro<br>170 | Lys | Pro | Glu | Cys | Ser<br>175 | Glu | Ser | Tyr | Thr | Leu<br>180 |
| Thr | Pro | Glu | Val | Gly<br>185 | Glu | Leu | Ile | Glu | Lys<br>190 | Val | Arg | Lys | Ala | His<br>195 |
| Gln | Glu | Thr | Phe | Pro<br>200 | Ala | leu | Cys | Gln | Leu<br>205 | Gly | Lys | Tyr | Thr | Thr<br>210 |
| Asn | Asn | Ser | Ser | Glu<br>215 | Gln | Arg | Val | Ser | Leu<br>220 | Asp | Ile | Asp | Leu | Trp<br>225 |
| Asp | Lys | Phe | Ser | Glu<br>230 | Leu | Ser | Thr | Lys | Cys<br>235 | Ile | Ile | Lys | Thr | Val<br>240 |
| Glu | Phe | Ala | Lys | Gln<br>245 | Leu | Pro | Gly | Phe | Thr<br>250 | Thr | Leu | Thr | Ile | Ala<br>255 |
| Asp | Gln | Ile | Thr | Leu<br>260 | Leu | Lys | Ala | Ala | Cys<br>265 | Leu | Asp | Ile | Leu | Ile<br>270 |
| Leu | Arg | Ile | Cys | Thr<br>275 | Arg | Tyr | Thr | Pro | Glu<br>280 | Gln | Asp | Thr | Met | Thr<br>285 |
| Phe | Ser | Asp | Gly | Leu<br>290 | Thr | Leu | Asn | Arg | Thr<br>295 | Gln | Met | His | Asn | Ala<br>300 |
| Gly | Phe | Gly | Pro | Leu<br>305 | Thr | Asp | Leu | Val | Phe<br>310 | Ala | Phe | Ala | Asn | Gln<br>315 |
| Leu | Leu | Pro | Leu | Glu<br>320 | Met | Asp | Asp | Ala | Glu<br>325 | Thr | Gly | Leu | Leu | Ser<br>330 |
| Ala | Ile | Cys | Leu | Ile<br>335 | Cys | Gly | Asp | Arg | Gln<br>340 | Asp | Leu | Glu | Gln | Pro<br>345 |
| Asp | Arg | Val | Asp | Met<br>350 | Leu | Gln | Glu | Pro | Leu<br>355 | Leu | Glu | Ala | Leu | Lys<br>360 |
| Val | Tyr | Val | Arg | Lys<br>365 | Arg | Arg | Pro | Ser | Arg<br>370 | Pro | His | Met | Phe | Pro<br>375 |
| Lys | Met | Leu | Met | Lys<br>380 | Ile | Thr | Asp | Leu | Arg<br>385 | Ser | Ile | Ser | Ala | Lys<br>390 |
| Gly | Ala | Glu | Arg | Val<br>395 | Ile | Thr | Leu | Lys | Met<br>400 | Glu | Ile | Pro | Gly | Ser<br>405 |
| Met | Pro | Pro | Leu | Ile<br>410 | Gln | Glu | Met | Leu | Glu<br>415 | Asn | Ser | Glu | Gly | Leu<br>420 |
| Asp | Thr | Leu | Ser | Gly<br>425 | Gln | Pro | Gly | Gly | Gly<br>430 | Gly | Arg | Asp | Gly | Gly<br>435 |
| Gly | Leu | Ala | Pro | Pro<br>440 | Pro | Gly | Ser | Cys | Ser<br>445 | Pro | Ser | Leu | Ser | Pro<br>450 |
| Ser | Ser | Asn | Arg | Ser<br>455 | Ser | Pro | Ala | Thr | His<br>460 | Ser | Pro | | | |

( 2 ) INFORMATION FOR SEQ ID NO:3:

( i ) SEQUENCE CHARACTERISTICS:
        ( A ) LENGTH:2658 base pairs
        ( B ) TYPE:nucleic acid
        ( C ) STRANDEDNESS:double
        ( D ) TOPOLOGY:linear ( i i ) MOLECULE TYPE:cDNA to mRNA
        ( A ) DESCRIPTION:page 4,RAR-alpha403 dominant negative;

deleted of 1311-1596 of SEQ. ID. NO (vii) IMMEDIATE SOURCE:
    (A) LIBRARY:cDNA (ix) SEQUENCE DESCRIPTION: SEQ ID NO:3:

| | | | | | |
|---|---|---|---|---|---|
| GCCATCTGGG | CCCAGGCCCC | ATGCCCCGAG | GAGGGGTGGT | CTGAAGCCCA | CCAGAGCCCC | 60 |
| CTGCCAGACT | GTCTGCCTCC | CTTCTGACTG | TGGCCGCTTG | GCATGGCCAG | CAACAGCAGC | 120 |
| TCCTGCCCGA | CACCTGGGGG | CGGGCACCTC | AATGGGTACC | CGGTGCCTCC | CTACGCCTTC | 180 |
| TTCTTCCCCC | CTATGCTGGG | TGGACTCTCC | CCGCCAGGCG | CTCTGACCAC | TCTCCAGCAC | 240 |
| CAGCTTCCAG | TTAGTGGATA | TAGCACACCA | TCCCCAGCCA | CCATTGAGAC | CCAGAGCAGC | 300 |
| AGTTCTGAAG | AGATAGTGCC | CAGCCCTCCC | TCGCCACCCC | CTCTACCCCG | CATCTACAAG | 360 |
| CCTTGCTTTG | TCTGTCAGGA | CAAGTCCTCA | GGCTACCACT | ATGGGGTCAG | CGCCTGTGAG | 420 |
| GGCTGCAAGG | GCTTCTTCCG | CCGCAGCATC | CAGAAGAACA | TGGTGTACAC | GTGTCACCGG | 480 |
| GACAAGAACT | GCATCATCAA | CAAGGTGACC | CGGAACCGCT | GCCAGTACTG | CCGACTGCAG | 540 |
| AAGTGCTTTG | AAGTGGGCAT | GTCCAAGGAG | TCTGTGAGAA | ACGACCGAAA | CAAGAAGAAG | 600 |
| AAGGAGGTGC | CCAAGCCCGA | GTGCTCTGAG | AGCTACACGC | TGACGCCGGA | GGTGGGGGAG | 660 |
| CTCATTGAGA | AGGTGCGCAA | AGCGCACCAG | GAAACCTTCC | CTGCCCTCTG | CCAGCTGGGC | 720 |
| AAATACACTA | CGAACAACAG | CTCAGAACAA | CGTGTCTCTC | TGGACATTGA | CCTCTGGGAC | 780 |
| AAGTTCAGTG | AACTCTCCAC | CAAGTGCATC | ATTAAGACTG | TGGAGTTCGC | CAAGCAGCTG | 840 |
| CCCGGCTTCA | CCACCCTCAC | CATCGCCGAC | CAGATCACCC | TCCTCAAGGC | TGCCTGCCTG | 900 |
| GACATCCTGA | TCCTGCGGAT | CTGCACGCGG | TACACGCCCC | AGCAGGACAC | CATGACCTTC | 960 |
| TCGGACGGGC | TGACCCTGAA | CCGGACCCAG | ATGCACAACG | CTGGCTTCGG | CCCCCTCACC | 102 |
| GACCTGGTCT | TTGCCTTCGC | CAACCAGCTG | CTGCCCCTGG | AGATGGATGA | TGCGGAGACG | 108 |
| GGGCTGCTCA | GCGCCATCTG | CCTCATCTGC | GGAGACCGCC | AGGACCTGGA | GCAGCCGGAC | 114 |
| CGGGTGGACA | TGCTGCAGGA | GCCGCTGCTG | GAGGCGCTAA | AGGTCTACGT | GCGGAAGCGG | 120 |
| AGGCCCAGCC | GCCCCCACAT | GTTCCCCAAG | ATGCTAATGA | AGATTACTGA | CCTGCGAAGC | 126 |
| ATCAGCGCCA | AGGGGCTGA | GCGGGTGATC | ACGCTGAAGA | TGGAGATCGT | AGCCGGGCAG | 132 |
| TACTGGGGAC | CTTCCCTGGG | GGACGGGGAG | GGAGGAGGCA | GCGACTCCTT | GGACAGAGGC | 138 |
| CTGGGCCCTC | AGTGGACTGC | CTGCTCCCAC | AGCCTGGGCT | GACGTCAGAG | GCCGAGGCCA | 144 |
| GGAACTGAGT | GAGGCCCCTG | GTCCTGGGTC | TCAGGATGGG | TCCTGGGGGC | CTCGTGTTCA | 150 |
| TCAAGACACC | CCTCTGCCCA | GCTCACCACA | TCTTCATCAC | CAGCAAACGC | CAGGACTTGG | 156 |
| CTCCCCCATC | CTCAGAACTC | ACAAGCCATT | GCTCCCAGC | TGGGGAACCT | CAACCTCCCC | 162 |
| CCTGCCTCGG | TTGGTGACAG | AGGGGGTGGG | ACAGGGGCGG | GGGGTTCCCC | CTGTACATAC | 168 |
| CCTGCCATAC | CAACCCCAGG | TATTAATTCT | CGCTGGTTTT | GTTTTTATTT | TAATTTTTT | 174 |
| GTTTTGATTT | TTTTAATAAG | AATTTTCATT | TTAAGCACAT | TTATACTGAA | GGAATTTGTG | 180 |
| CTGTGTATTG | GGGGGAGCTG | GATCCAGAGC | TGGAGGGGT | GGGTCCGGGG | GAGGGAGTGG | 186 |
| CTCGGAAGGG | GCCCCCACTC | TCCTTTCATG | TCCCTGTGCC | CCCCAGTTCT | CCTCCTCAGC | 192 |
| CTTTTCCTCC | TCAGTTTTCT | CTTTAAAACT | GTGAAGTACT | AACTTTCCAA | GGCCTGCCTT | 198 |
| CCCCTCCCTC | CCACTGGAGA | AGCCGCCAGC | CCCTTTCTCC | CTCTGCCTGA | CCACTGGGTG | 2040 |
| TGGACGGTGT | GGGGCAGCCC | TGAAAGGACA | GGCTCCTGGC | CTTGGCACTT | GCCTGCACCC | 2100 |
| ACCATGAGGC | ATGGAGCAGG | GCAGAGCAAG | GGCCCCGGGA | CAGAGTTTTC | CCAGACCTGG | 2160 |
| CTCCTCGGCA | GAGCTGCCTC | CCGTCAGGGC | CCACATCATC | TAGGCTCCCC | AGCCCCCACT | 2220 |

```
GTGAAGGGGC  TGGCCAGGGG  CCCGAGCTGC  CCCCACCCCC  GGCCTCAGCC  ACCAGCACCC    2280

CCATAGGGCC  CCCAGACACC  ACACACATGC  GCGTGCGCAC  ACACACAAAC  ACACACACAC    2340

TGGACAGTAG  ATGGGCCGAC  ACACACTTGG  CCCGAGTTCC  TCCATTTCCC  TGGCCTGCCC    2400

CCCACCCCCA  ACCTGTCCCA  CCCCCGTGCC  CCCTCCTTAC  CCCGCAGGAC  GGGCCTACAG    2460

GGGGGTCTCC  CCTCACCCCT  GCACCCCCAG  CTGGGGGAGC  TGGCTCTGCC  CCGACCTCCT    2520

TCACCAGGGG  TTGGGGCCCC  TTCCCTGGA   GCCCGTGGGT  GCACCTGTTA  CTGTTGGGCT    2580

TTCCACTGAG  ATCTACTGGA  TAAAGAATAA  AGTTCTATTT  ATTCTAAAAA  AAAAAAAAA    2640

AAAAAAAAA   AAAAAAA                                                       2658
```

(2) INFORMATION FOR SEQ ID NO:4:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: polypeptide
        (A) DESCRIPTION: sequence encoded by SEQ. ID. NO. 3;
        RAR- alpha403

(ix) SEQUENCE DESCRIPTION: SEQ ID NO:4:

```
Met  Ala  Ser  Asn  Ser  Ser  Ser  Cys  Pro  Thr  Pro  Gly  Gly  Gly  His
                         5                    10                        15

Leu  Asn  Gly  Tyr  Pro  Val  Pro  Pro  Tyr  Ala  Phe  Phe  Phe  Pro  Pro
                        20                    25                        30

Met  Leu  Gly  Gly  Leu  Ser  Pro  Pro  Gly  Ala  Leu  Thr  Thr  Leu  Gln
                        35                    40                        45

His  Gln  Leu  Pro  Val  Ser  Gly  Tyr  Ser  Thr  Pro  Ser  Pro  Ala  Thr
                        50                    55                        60

Ile  Glu  Thr  Gln  Ser  Ser  Ser  Ser  Glu  Glu  Ile  Val  Pro  Ser  Pro
                        65                    70                        75

Pro  Ser  Pro  Pro  Pro  Leu  Pro  Arg  Ile  Tyr  Lys  Pro  Cys  Phe  Val
                        80                    85                        90

Cys  Gln  Asp  Lys  Ser  Ser  Gly  Tyr  His  Tyr  Gly  Val  Ser  Ala  Cys
                        95                    100                       105

Glu  Gly  Cys  Lys  Gly  Phe  Phe  Arg  Arg  Ser  Ile  Gln  Lys  Asn  Met
                       110                   115                        120

Val  Tyr  Thr  Cys  His  Arg  Asp  Lys  Asn  Cys  Ile  Ile  Asn  Lys  Val
                       125                   130                        135

Thr  Arg  Asn  Arg  Cys  Gln  Tyr  Cys  Arg  Leu  Gln  Lys  Cys  Phe  Glu
                       140                   145                        150

Val  Gly  Met  Ser  Lys  Glu  Ser  Val  Arg  Asn  Asp  Arg  Asn  Lys  Lys
                       155                   160                        165

Lys  Lys  Glu  Val  Pro  Lys  Pro  Glu  Cys  Ser  Glu  Ser  Tyr  Thr  Leu
                       170                   175                        180

Thr  Pro  Glu  Val  Gly  Glu  Leu  Ile  Glu  Lys  Val  Arg  Lys  Ala  His
                       185                   190                        195

Gln  Glu  Thr  Phe  Pro  Ala  leu  Cys  Gln  Leu  Gly  Lys  Tyr  Thr  Thr
                       200                   205                        210

Asn  Asn  Ser  Ser  Glu  Gln  Arg  Val  Ser  Leu  Asp  Ile  Asp  Leu  Trp
                       215                   220                        225

Asp  Lys  Phe  Ser  Glu  Leu  Ser  Thr  Lys  Cys  Ile  Ile  Lys  Thr  Val
                       230                   235                        240
```

| | | | | | | | | | | | | | | |
|---|---|---|---|---|---|---|---|---|---|---|---|---|---|---|
|Glu|Phe|Ala|Lys|Gln 245|Leu|Pro|Gly|Phe|Thr 250|Thr|Leu|Thr|Ile|Ala 255|
|Asp|Gln|Ile|Thr|Leu 260|Leu|Lys|Ala|Ala|Cys 265|Leu|Asp|Ile|Leu|Ile 270|
|Leu|Arg|Ile|Cys|Thr 275|Arg|Tyr|Thr|Pro|Glu 280|Gln|Asp|Thr|Met|Thr 285|
|Phe|Ser|Asp|Gly|Leu 290|Thr|Leu|Asn|Arg|Thr 295|Gln|Met|His|Asn|Ala 300|
|Gly|Phe|Gly|Pro|Leu 305|Thr|Asp|Leu|Val|Phe 310|Ala|Phe|Ala|Asn|Gln 315|
|Leu|Leu|Pro|Leu|Glu 320|Met|Asp|Asp|Ala|Glu 325|Thr|Gly|Leu|Leu|Ser 330|
|Ala|Ile|Cys|Leu|Ile 335|Cys|Gly|Asp|Arg|Gln 340|Asp|Leu|Glu|Gln|Pro 345|
|Asp|Arg|Val|Asp|Met 350|Leu|Gln|Glu|Pro|Leu 355|Leu|Glu|Ala|Leu|Lys 360|
|Val|Tyr|Val|Arg|Lys 365|Arg|Arg|Pro|Ser|Arg 370|Pro|His|Met|Phe|Pro 375|
|Lys|Met|Leu|Met|Lys 380|Ile|Thr|Asp|Leu|Arg 385|Ser|Ile|Ser|Ala|Lys 390|
|Gly|Ala|Glu|Arg|Val 395|Ile|Thr|Leu|Lys|Met 400|Glu|Ile|Pro| | |

(2) INFORMATION FOR SEQ ID NO:5:

(i) SEQUENCE CHARACTERISTICS:
        (A) LENGTH:704 base pairs
        (B) TYPE:nucleic acid
        (C) STRANDEDNESS:double
        (D) TOPOLOGY:linear (i i) MOLECULE TYPE:cDNA to mRNA
        (A) DESCRIPTION:page 11; RAR-alpha RA binding region;
            positions 692 to 1395 of SEQ. ID. NO (v i i) IMMEDIATE SOURCE:
        (A) LIBRARY:cDNA (i x) SEQUENCE DESCRIPTION: SEQ ID NO:5:

| | | | | | |
|---|---|---|---|---|---|
|AAACCTTCCC|TGCCCTCTGC|CAGCTGGGCA|AATACACTAC|GAACAACAGC|TCAGAACAAC|60|
|GTGTCTCTCT|GGACATTGAC|CTCTGGGACA|AGTTCAGTGA|ACTCTCCACC|AAGTGCATCA|120|
|TTAAGACTGT|GGAGTTCGCC|AAGCAGCTGC|CCGGCTTCAC|CACCCTCACC|ATCGCCGACC|180|
|AGATCACCCT|CCTCAAGGCT|GCCTGCCTGG|ACATCCTGAT|CCTGCGGATC|TGCACGCGGT|240|
|ACACGCCCCA|GCAGGACACC|ATGACCTTCT|CGGACGGGCT|GACCCTGAAC|CGGACCCAGA|300|
|TGCACAACGC|TGGCTTCGGC|CCCCTCACCG|ACCTGGTCTT|TGCCTTCGCC|AACCAGCTGC|360|
|TGCCCCTGGA|GATGGATGAT|GCGGAGACGG|GGCTGCTCAG|CGCCATCTGC|CTCATCTGCG|420|
|GAGACCGCCA|GGACCTGGAG|CAGCCGGACC|GGGTGGACAT|GCTGCAGGAG|CCGCTGCTGG|480|
|AGGCGCTAAA|GGTCTACGTG|CGGAAGCGGA|GGCCCAGCCG|CCCCCACATG|TTCCCCAAGA|540|
|TGCTAATGAA|GATTACTGAC|CTGCGAAGCA|TCAGCGCCAA|GGGGGCTGAG|CGGGTGATCA|600|
|CGCTGAAGAT|GGAGATCCCG|GGCTCCATGC|CGCCTCTCAT|CCAGGAAATG|TTGGAGAACT|660|
|CAGAGGGCCT|GGACACTCTG|AGCGGACAGC|CGGGGGGTGG|GGGG| |704|

(2) INFORMATION FOR SEQ ID NO:6:

(i) SEQUENCE CHARACTERISTICS:
        (A) LENGTH:201 base pairs ( B ) TYPE:nucleic acid
( C ) STRANDEDNESS:double
( D ) TOPOLOGY:linear ( i i ) MOLECULE TYPE:cDNA to mRNA
( A ) DESCRIPTION:page 11, RAR-alpha DNA binding region;
positions 364 to 564 of SEQ. ID. NO ( v i i ) IMMEDIATE SOURCE:
( A ) LIBRARY:cDNA ( i x ) SEQUENCE DESCRIPTION: SEQ ID NO:6:

| | | | | | | |
|---|---|---|---|---|---|---|
| TGCTTTGTCT | GTCAGGACAA | GTCCTCAGGC | TACCACTATG | GGGTCAGCGC | CTGTGAGGGC | 60 |
| TGCAAGGGCT | TCTTCCGCCG | CAGCATCCAG | AAGAACATGG | TGTACACGTG | TCACCGGGAC | 120 |
| AAGAACTGCA | TCATCAACAA | GGTGACCCGG | AACCGCTGCC | AGTACTGCCG | ACTGCAGAAG | 180 |
| TGCTTTGAAG | TGGGCATGTC | C | | | | 201 |

( 2 ) INFORMATION FOR SEQ ID NO:7:

( i ) SEQUENCE CHARACTERISTICS:
( A ) LENGTH:261 base pairs
( B ) TYPE:nucleic acid
( C ) STRANDEDNESS:double
( D ) TOPOLOGY:linear ( i i ) MOLECULE TYPE:cDNA to mRNA
( A ) DESCRIPTION:page 11, RAR-alpha N- terminal region;
positions 103 to 363 of SEQ. ID. NO.

( v i i ) IMMEDIATE SOURCE:
( A ) LIBRARY:cDNA ( i x ) SEQUENCE DESCRIPTION: SEQ ID NO:7:

| | | | | | | |
|---|---|---|---|---|---|---|
| ATGGCCAGCA | ACAGCAGCTC | CTGCCCGACA | CCTGGGGGCG | GGCACCTCAA | TGGGTACCCG | 60 |
| GTGCCTCCCT | ACGCCTTCTT | CTTCCCCCCT | ATGCTGGGTG | GACTCTCCCC | GCCAGGCGCT | 120 |
| CTGACCACTC | TCCAGCACCA | GCTTCCAGTT | AGTGGATATA | GCACACCATC | CCCAGCCACC | 180 |
| ATTGAGACCC | AGAGCAGCAG | TTCTGAAGAG | ATAGTGCCCA | GCCCTCCCTC | GCCACCCCCT | 240 |
| CTACCCCGCA | TCTACAAGCC | T | | | | 261 |

( 2 ) INFORMATION FOR SEQ ID NO:8:

( i ) SEQUENCE CHARACTERISTICS:
( A ) LENGTH:93 base pairs
( B ) TYPE:nucleic acid
( C ) STRANDEDNESS:double
( D ) TOPOLOGY:linear ( i i ) MOLECULE TYPE:cDNA to mRNA
( A ) DESCRIPTION:page 11, RAR-alpha N- terminal region;
positions 1396 to 1488 of SEQ. ID. N ( v i i ) IMMEDIATE SOURCE:
( A ) LIBRARY:cDNA ( i x ) SEQUENCE DESCRIPTION: SEQ ID NO:8:

| | | | | | | |
|---|---|---|---|---|---|---|
| CGGGACGGGG | GTGGCCTGGC | CCCCCCGCCA | GGCAGCTGTA | GCCCCAGCCT | CAGCCCCAGC | 60 |
| TCCAACAGAA | GCAGCCCGGC | CACCCACTCC | CCG | | | 93 |

( 2 ) INFORMATION FOR SEQ ID NO:9:

( i ) SEQUENCE CHARACTERISTICS:
( A ) LENGTH:16 base pairs
( B ) TYPE:nucleic acid
( C ) STRANDEDNESS:double
( D ) TOPOLOGY:linear -continued

```
    ( i i ) MOLECULE TYPE:cDNA to mRNA
            ( A ) DESCRIPTION:page 28, TRE ( v i i ) IMMEDIATE SOURCE:
            ( A ) LIBRARY:cDNA ( i x ) SEQUENCE DESCRIPTION: SEQ ID NO:9:

TCAGGTCATG ACCTGA                                                            16

( 2 ) INFORMATION FOR SEQ ID NO:10:

( i ) SEQUENCE CHARACTERISTICS:
            ( A ) LENGTH:24 base pairs
            ( B ) TYPE:nucleic acid
            ( C ) STRANDEDNESS:double
            ( D ) TOPOLOGY:linear ( i i ) MOLECULE TYPE:cDNA to mRNA
            ( A ) DESCRIPTION:page 28, RRE ( v i i ) IMMEDIATE SOURCE:
            ( A ) LIBRARY:cDNA ( i x ) SEQUENCE DESCRIPTION: SEQ ID NO:10:

GTAGGGTTCA CCGAAAGTTC ACTC                                                   24
```

CREATING NOVEL HEMATOPOIETIC CELL LINES BY EXPRESSING ALTERED RETINOIC ACID RECEPTORS

The present application is a U.S. National stage application under 35 U.S.C. 371 continuation of PCT/US94/08450, which is a continuation-in-part of U.S. Ser. No. 08/099,242, filed 28 Jul. 1993, which is now abandoned.

This invention was made with U.S. government support under grants CA 01676 and CA 58292 awarded by the National Cancer Institute. The U.S. government has certain rights in the invention.

FIELD OF THE INVENTION

This invention relates to genetic engineering and particularly to hematopoietic cell lines bearing altered retinoic acid receptors.

BACKGROUND OF THE INVENTION

Abbreviations used herein include: APL, acute promyelocytic leukemia; ATRA, all-trans retinoic acid; BFU-E, burst-forming unit-erythroid; CAT, chloramphenicol acetyltransferase; CFU-E, colony-forming unit-erythroid; CFU-GM, colony-forming unit-granulocyte/macrophage; Epo, erythropoietin; GM-CSF, granulocyte-macrophage colony stimulating factor; IL-3, interleukin-3; IL-6, interleukin-6; IL-7, interleukin-7; IL-11, interleukin-11; HS, horse serum; IgE R, immunoglobulin E receptor; RA, retinoic acid; RARα, retinoic acid receptor-α; RARs, retinoic acid receptors; RXR, retinoid X receptor; SCF, stem cell factor.

Retinoic acid (RA), the natural acidic derivative of vitamin A (retinol), is a critical molecule regulating growth and differentiation of a wide variety of cells. RA is thought to be centrally involved in epithelial differentiation (37; see the appended citations), plays a critical role as a tissue-specific morphogen during embryogenesis (50) and as a suppressor of malignant transformation of epithelial cells both in vitro (39) and in vivo (29). These diverse and complex biologic effects of RA are mediated through a number of closely related nuclear RA receptors (RARs) that are members of the steroid/thyroid hormone receptor superfamily and possess discrete DNA-binding and RA (ligand) binding domains (22).

The expression of RARs is widespread with RAR mRNA noted in most fetal and adult tissue (57). Unlike the steroid hormone receptors, the RA receptors as well as thyroid hormone receptors appear to be associated with chromatin and may be constitutively bound to cis-acting regulatory sequences in the absence of ligand (10, 35). Thus these receptors may have different regulatory roles in the absence and presence of ligand.

Several lines of indirect evidence suggest that RA and RA receptors may be involved in regulating the development of hematopoietic progenitors. For example, RA receptor mRNA (predominantly RARα) is widely expressed in different hematopoietic cell types (18, 23, 34). Treatment of a human myeloid leukemia cell line HL-60 with all-trans retinoic acid (ATRA) induces these cells to undergo terminal neutrophilic differentiation, and this induction is directly mediated through RARα (3, 8). In addition, human acute promyelocytic leukemia (APL) exhibits a specific 15:17 chromosome translocation involving RARα which presumably results in the disruption of a normal, albeit unknown, regulatory function of this particular RA receptor (1, 2, 20, 21, 32). Furthermore, ATRA induces the leukemia cells from APL patients to differentiate into mature neutrophils both in vitro and in vivo (4, 5, 30, 55). However, it is currently unknown if RA and RA receptors might also be involved in regulating normal hematopoietic differentiation.

Normal hematopoietic differentiation involves a single primitive stem cell that gives rise to all the other types of hematopoietic cells. The existence of a common pluripotential stem cell that is the progenitor of all lymphoid, myeloid, and erythroid cells was initially demonstrated by transplantation experiments using bone marrow cells carrying X-ray-induced chromosomal markers (55a). More recently, direct marking of bone marrow cells with retroviral vectors has further confirmed the existence of a common lympho-hematopoietic progenitor cell (36a). Through a combination of physical and immunological purification methods, the murine lympho-hematopoietic progenitor cells have been purified to near homogeneity (47a). Their frequency is estimated to be only 0.01–0.005% of all nucleated cells in the bone marrow. The scarcity of the lympho-hematopoietic stem cells and the difficulty in their purification and maintenance have hampered efforts to purify appreciable numbers of these cells. If such cells were available as continuous cell lines, they could be used to dissect the molecular mechanisms controlling lymphoid and hematopoietic development and for developing diagnostic tests and for screening potentially useful therapeutic compounds. A continuous cell line capable of both lymphoid and myeloerythroid differentiation in vitro would greatly facilitate such endeavors. Also, such cells are potentially of great therapeutic value in reconstituting the blood and immune systems of patients whose own stem cells are deficient, e.g., patients that have received radiation therapy or chemotherapy.

It is currently unclear whether RA and RARs play any roles in the differentiation of normal lympho-hematopoietic progenitors. A difficulty intrinsic to any study of the possible roles of RA in normal hematopoietic differentiation is the fact that most cell lines or primary bone marrow cells suitable for such experiments require in the culture medium serum that contains substantial amount of RA (approximately $10^{-9}$ to $10^{-8}$M) (13). Although methods exist to remove RA from serum, such procedures unavoidably remove other serum constituents which may be important in the growth or differentiation of neutrophils. An alternative approach to study the role of RA in hematopoiesis is to use mutated RAR constructs with dominant negative activity to suppress the function of endogenous RARs in hematopoietic progenitors. "Dominant negative" genes encode abnormal proteins that repress the function of their normal counterparts in a dominant manner (26). A prototype example is the v-erbA oncogene which represses the transcription-regulating function of normal thyroid hormone receptors (encoded by c-erbA), and this contributes to the transformation of erythroblasts (10, 59). A small deletion in the C-terminus of v-erbA appears to be responsible for most of the dominant negative activity of this oncogene in transient expression assays (10, 46, 59). Thus, one way to examine the role of RARs in hematopoiesis is to utilize "dominant negative" receptor constructs that would suppress normal RAR function in hematopoietic precursors and then determine if the expression of these constructs would alter the growth and differentiation of these blood cell progenitors. However, dominant negative constructs are only rarely useful in studying the cell biology of a gene because many complications arise from the simultaneous expression of the normal gene products and the dominant negative construct in the cell. For instance, in the case of a hypothetical receptor the effect of a dominant negative construct on a physiological process in a cell may depend upon at least the following: 1) the levels of expression of the dominant negative construct and the natural gene product in the cell; 2) the level of ligand:receptor complex required to induce the physiological process in the cell; 3) the mechanisms that regulate expression of the natural gene product (e.g., feedback regulation by the ligand:receptor complex or coordinate regulation with some other gene in the cell); and 4) the post-transcriptional and post-translational processing of the natural receptor and the dominant negative suppressor. The inventors believe that the present disclosure represents the first successful use of a dominant negative construct to inhibit a physiological effect in any stem cell, particularly an effect required for differentiation, and more particularly for differentiation of a hematopoietic stem cell. The disclosure illustrates that RARs influence hamatopoietic lineage development at the lympho-hematopoietic progenitor stage as well as playing a previously unknown role in controlling the terminal differentiation of neutrophilic promyelocytes (52a).

SUMMARY OF THE INVENTION

The retinoic acid receptor (RARα) is expressed in virtually all hematopoietic lineages, but the role of this transcription factor in regulating the growth and differentiation of hematopoietic progenitors is unknown. A mutant RARα was constructed that exhibits both dominant negative activity against the normal RARα in transient expression assays and inhibits retinoic acid-induced neutrophilic differentiation of the HL-60 human promyelocytic leukemia cell line.

This dominant negative RARα construct was introduced into normal mouse bone marrow cells by retroviral vector-mediated transduction to produce continuous SCF-dependent lympho-hematopoietic progenitor cell lines (EML cells). EML cells can be induced with IL-7 and bone marrow stromal cells to express characteristics of pre-pro-B lymphocytes. When induced with Epo, EML cells gave rise to BFU-Es, and when treated with SCF, IL-3, and high concentrations of RA, gave rise to CFU-GMs. These CFU-GMs formed colonies of neutrophils, macrophages, and promyelocytes in the presence of GM-CSF. Stimulation of EML cells with IL-3 caused the appearance of mast cells. With simultaneous stimulation with SCF, IL-3, Epo, IL-6, and IL-11, EML cells gave rise to occasional megakaryocytes. Taken together, these data indicate that the SCF-dependent EML cell line contains progenitors capable of differentiation along B-lymphocyte, erythtocyte, neutrophil, macrophage, mast cell, and megakaryocyte lineages. Thus, EML cells are the only known SCF-dependent cell line with both lymphoid and myelo-erythroid potentials.

When the dominant negative RARα construct was introduced into the multipotent interleukin-3 (IL-3) dependent FDCP mix A4 murine hematopoietic cell line, there was a rapid switch from spontaneous neutrophil/monocyte differentiation to basophil/mast cell development in the presence of IL-3 (52a). Thus, in this multipotent hemopoietic cell line the normal RARα transcription factor and/or related molecules appear to promote the differentiation of neutrophils and monocytes but suppress the development of basophils/mast cells. Suppression of the endogenous RARs in FDCP mix A4 cells with a dominant negative RARα mutation results in a reversion of this differentiation pattern. The switch appears to act at the level of commitment of the hematopoietic stem cell to a lineage.

The role of retinoic acid receptors in the terminal differentiation of neutrophil progenitors also was investigated using the FDCP mix A4 cell line as well as normal mouse bone marrow cells (52a). Treatment of the IL-3-dependent FDCP mix A4 cells with murine granulocyte-macrophage colony stimulating factor (GM-CSF) induced the cells to differentiate into neutrophils and macrophages. When the endogenous retinoic acid receptor activity in FDCP mix A4 cells was suppressed by a dominant negative retinoic acid receptor construct, the GM-CSF-induced neutrophil differentiation was blocked at the promyelocyte stage. The blocked neutrophilic promyelocytes proliferated continuously (over 9 months) as a GM-CSF-dependent cell line but could be induced to terminally differentiate into neutrophils with supra physiological concentrations of RA ($10^{-6}$ to $10^{-5}$M). The ability of the dominant negative retinoic acid receptor to block neutrophil differentiation at the promyeloycte stage was also demonstrated in normal, primary mouse bone marrow cells. The results indicate that retinoic acid receptors in conjunction with hematopoietic growth factors play a crucial role in the terminal differentiation of normal neutrophil precursors.

DESCRIPTION OF THE DRAWINGS

FIGS. 1A–1D show structures of RARα403 and the retroviral vector LRARα403SN. FIG. 1A shows a schematic representation of human RARα cDNA. The bar represents the open reading frame which encodes the normal human RARα (462 amino acids). Solid bar represents the DNA-binding domain of RARα. RA represents the hormone-binding domain. FIG. 1B depicts the structure of the truncated receptor RARα403 cDNA. Nucleotides 1311 to 1596 of human RARα cDNA were deleted by digestion with SmaI and a stop codon was inserted at amino acid position 404 using an NheI linker. The truncated receptor consists of 403 amino acids and is termed herein RARα403. FIG. 1C schematically depicts the retroviral vector LXSN. LTR: Molony murine leukemia virus long terminal repeat. Arrows: transcription initiation site. SV: SV40 promoter. Neo: neomycin phosphotransferase gene. pA: polyadenylation site. FIG. 1D depicts the structure of the retroviral vector LRARα403SN. RARα403 was inserted into the EcoRI-BamHI cloning sites of LXSN. The vector was used both as an expression vector in transient expression assays and for producing retroviral particles.

FIG. 2A graphically depicts the levels of CAT activity in RARα- or RARα403-transduced NIH3T3 tk⁻ cells. Transactivation activities of RARα and RARα403 were studied in the absence and presence of 1 μM RA. An expression plasmid pTRE-CAT was used as the reporter. RARα represents the expression plasmid pEMSV-RARα while RAR α403 refers to pLRARα403SN (FIG. 1D). The volume of lysate used in CAT assay was normalized for transfection efficiency determined by expression of the cotransfected growth hormone reporter pCMV-GH. The DNA ratio of pEMSV-RARα to pLRARα403SN varied from 1:1 to 1:6. pLXSN was used to equalize the total amount (23.5 μg per 100-mm dish) of DNA and LTRs transfected. Each + represents 2.5 μg of plasmid DNA. Higher amounts (5 μg) of transfected pLRARα403SN resulted in suppression of over 60% of endogenous RAR activity (not shown). FIG. 2B depicts, in a manner similar to FIG. 2A, the results obtained using pRRE-CAT as the reporter construct, instead of pTRE-CAT. Each + represents 1 μg of plasmid DNA. The total amount of DNA was 16 μg per 100-mm dish.

FIG. 3 graphically depicts how the dominant negative RARα403 construct blunts neutrophil differentiation in HL-60 cells. HL-60/LXSN D.1 and D.2 are two randomly selected HL-60 clones infected with the control vector LXSN. HL-60/LRARα403SN D.2 and D.5 are two HL-60 clones infected with LRARα403SN that express high levels of the full-length 4.7 kb retroviral vector mRNA containing RARα403 sequence. Cells were induced with the indicated concentrations of RA for 5 days. Differential counts were then performed on Wright-Giemsa stained cytospin preparations and represent the means of triplicate experiments.

FIG. 4A depicts the level of expression of LRARα403SN. The full-length message of LRARα403SN is 4.7 kb. The RARα probe also detects the 3.6 and 2.6 kb endogenous mouse RARα mRNA. The ratio of RARα403 to endogenous RARα message in cells infected with LRARα403SN is greater than 10:1. FIG. 4B depicts the level of expression of GATA- 1. The 1.8 kb GATA-1 mRNA is indicated.

FIG. 5A shows uninfected FDCP mix A4 cells. Most cells are undifferentiated blasts. Arrow points to a mature neutrophil. Arrowheads point to differentiating cells. FIG. 5B shows FDCP mix A4 infected with control vector LXSN. Arrow points to a neutrophil. FIG. 5C shows FDCP mix A4 infected with LRARα403SN. Most cells (arrows) are differentiated and contain numerous basophilic granules and oval nuclei. FIG. 5D shows a higher magnification of FIG. 5B. FIG. 5E shows a higher magnification of FIG. 5C. FIG. 5F is a photomicrograph of a toluidine blue stain of FDCP mix A4 cells infected with LRARα403SN. The granules in many cells (arrows) stain metachromatically with toluidine blue, indicating that these cells are of the basophil/mast cell lineage.

FIG. 8A schematically depicts α functioning normally with the IL-3 dependent FDCP mix A4 cells exhibiting prominent self renewal and a predominance of spontaneous differentiation along the neutrophil and monocyte lineages (solid arrows); and, in this case spontaneous differentiation to basophils/mast cell lineage is suppressed (dotted arrows). FIG. 8B schematically depicts the effects of the dominant negative LRARα403SN in FDCP mix A4 cells where the normal LRARα403SN function is suppressed, and the cells exhibit prominent spontaneous differentiation into basophils/mast cells, with differentiation to neutrophils and monocytes being suppressed. The LRARα403SN infected cells remain IL-3 dependent, but self renewal is markedly diminished.

FIGS. 16B–D (Prior Art) shows the nucleotide and amino acid sequence of RARα clone λK1R as described (25).

FIG. 17 tabulates the effects of retinoic acid on the production of CFU-GM, BFU-E and the self-renewal in EML.

FIG. 18(A) shows a Southern blot illustrating that several clones of EML cells harbor the neo gene and that all contain a single, identical integration site. "EML bulk" denotes DNA from bulk cells harboring RARα403 that have not been subcloned in methylcellulose. "EML C1" DNA is from a line of cells subcloned from the bulk culture, and "EML C1.4" DNA is derived from cells subcloned from EML C1 cells. FIG. 18(B) depicts a Northern blot showing that EML cells express high levels of the retroviral mRNA that encodes the transduced RARα gene. FIG. 18(C) shows a Southern blot illustrating five different integration sites for RARα403 in EML-type cells. "New bulk" represents DNA from a bulk culture of non-subcloned EML cells; four different integration sites are apparent in these cells (lane 2). A fifth and distinct integration site is apparent in lane-1, which contains DNA from the subcloned EML C1 cells. Since the bulk cells and the EML C1 cells of FIG. 18C shared the same lympho-hematopoietic stem cell properties yet displayed different integration sites for RARα403, this experiment illustrates that a common retroviral integration site is not required for the immortalization of lympho-hematopoietic progenitors.

FIG. 19(A) negative control; Anti-Sca-1, which FIG. 19(B) is specific for stem cells/primitive progenitors (47a); FIG. 19(C) Anti-B220, which is specific for the B lymphocyte lineage (5a); FIG. 19(E) Anti-Mac, which is specific for macrophage/neutrophil lineages; FIG. 19(F) Monoclonal antibody "7/4," which is specific for the neutrophil lineage (28); and FIG. 19(D) Monoclonal antibody "ter 119," which recognizes erythroid precursors and probably some nonerythroid blasts (30a). FIG. 19 illustrates that 50% of EML C1 cells are positive for Sca-1, about 53% express B220, roughly 51% express ter 119, and very few express "7/4" or Mac-1.

FIG. 21 ((B), lanes 5 and 6, illustrate that D–J rearrangements are present in EML cells only after they have been induced with bone marrow stromal cells (W20 cells) and IL-7, thus suggesting that the B220-positive EML cells present before induction are at the pre-pro-B stage.

FIG. 22 illustrates the production of erythroid progenitors in EML cells four days after Epo was added to the cultures.

FIG. 6(F) shows EML-derived CFU-GMs that had been cultured in media containing GM-CSF, illustrating their proliferation and differentiation along the neutrophil and macrophage lineages.

DETAILED DESCRIPTION OF THE INVENTION

Figure 2A:
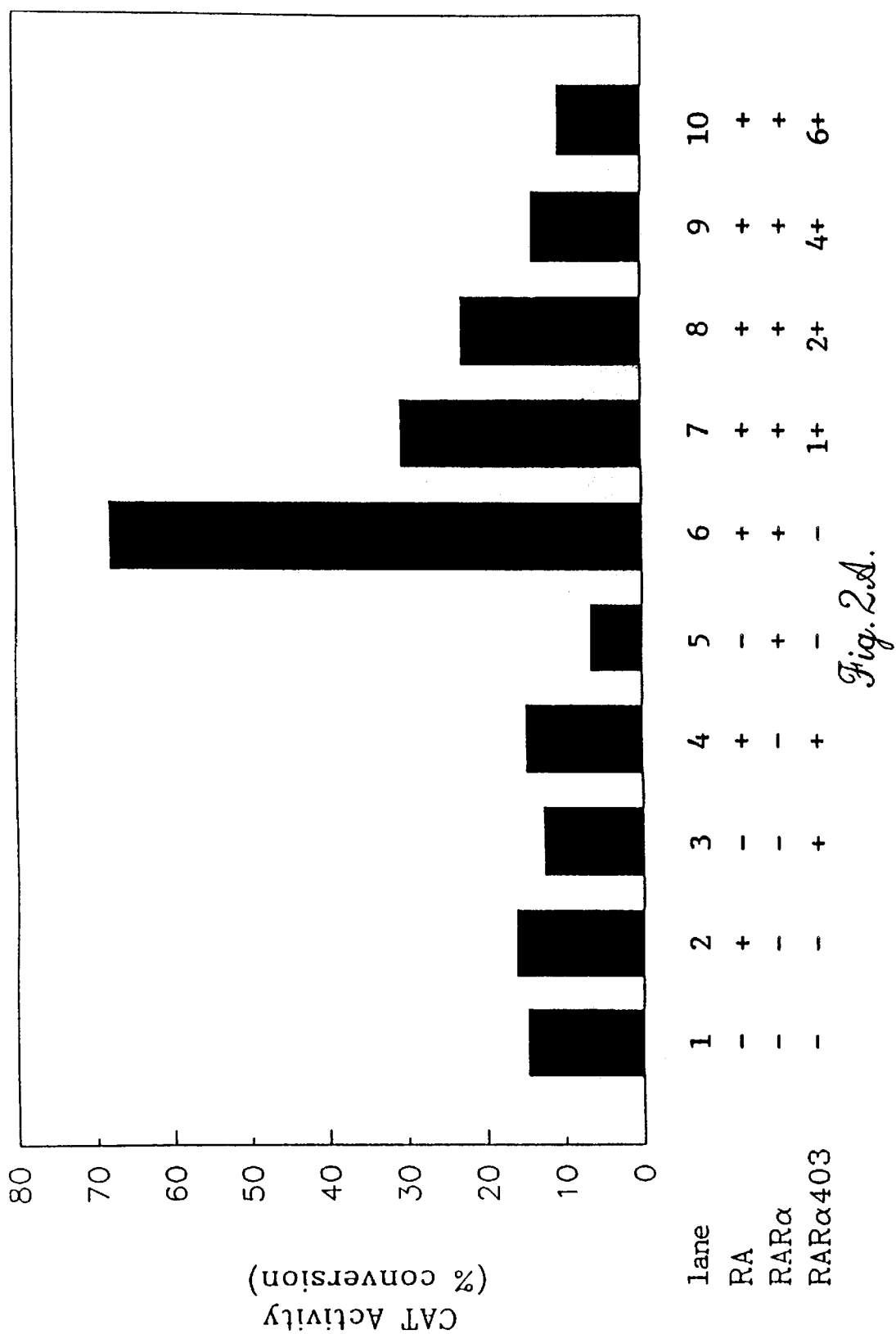
FIGS. 2A–2B graphically depicts that the truncated RARα403 exhibits dominant negative activity against endogenous RARs on expression of a downstream CAT gene as measured by CAT activity in transient expression assays.

In their study of retinoic acid receptor function in hematopoietic differentiation, the inventors constructed a mutant RARα that exhibited dominant negative activity in both mouse NIH3T3 fibroblasts, and in the HL-60 human promyelocytic leukemia cell line. The dominant negative construct, when introduced into the multipotent IL-3 dependent FDCP mix A4 murine hematopoietic cell line in the presence of IL-3, induced an unexpected and marked switch from spontaneous neutrophil/monocyte differentiation into the development of basophils and mast cells. These observations suggest a previously unsuspected role for retinoic acid receptors in the development of myeloid progenitors into mast cells and basophils. Therapeutic regulation of mast cell and basophil development is an important consideration in treatment of patients with mast cell proliferative diseases, asthma, and other acute and chronic allergic diseases due to Type I (or immediate) hypersensitivity reactions.

Studies of the effects of the dominant negative construct on primary cultures of $BDF_1$ bone marrow cells revealed another surprising result: When a retroviral vector was used to transduce the dominant negative RARα403 construct into bone marrow cells, a small proportion of the cells became immortalized as pluripotential lympho-hematipoietic stem cells resembling the common progenitor that gives rise to all lympoid and hematopoietic cells. The immortalized stem cells were capable of giving rise to hematopoietic progenitors of the erythroid, myeloid, and lymphocytic lineages.

In the myeloid lineages derived from RARα403 transduction into bone marrow cells, the terminal differentiation of neutrophils was blocked at the promyelocyte stage, resulting in cells that could proliferate continuously as a cell line. Furthermore, this block to terminal differentiation could be overcome by using high concentrations of retinoic acid (i.e., concentrations in the range of about $10^{-6}$ to about $10^{-5}$M). In four separate transduction experiments using murine bone marrow, four continuous cultures of neutrophilic promyelocytic cell lines were established, and in all cases the cells were blocked at the same point in the terminal differentiation pathway of neutrophils. The blocked promyelocytes resemble in phenotype human acute promyelocytic leukemia (APL) cells and may serve as a model for studying the pathogenesis of this type of leukemia.

The term "hematopoietic" refers to cells found in the blood, bone marrow, spleen, lymph, or other lympho-hematopoietic compartments of the body. In particular, this term refers to cells of the lymphoid, erythroid, and myeloid lineages in all stages of their differentiation, and includes the common lympho-hematopoietic stem cell that gives rise to all three of these lineages.

The term "blast" refers to hematopoietic cells that are committed to one of the three cell lineages (lympoid, erythroid, or myeloid), but that are in early stages of differentiation. When stimulated with appropriate growth factors, blasts divide to produce a large number of cells that are more differentiated than the blast stage of differentiation. Examples are lymphoblasts, erythroblasts, and myeloblasts. Cells that are more differentiated than blasts but not yet fully differentiated are appended with the prefix "pro." Examples are pro-lymphocytes, pro-erythrocytes, and promyelocytes.

The term "hematopoietic stem cell" is used to mean any hematopoietic cell that is not terminally differentiated and that is still capable of self-renewal or that is capable of cell divisions resulting in daughter cells that are more differentiated than the parent cell. In accord with this definition, promyelocytes as well as pluripotential stem cells are considered to be "stem cells."

The term "lympho-hematopoietic stem cell" refers to those pluripotential hematopoietic stem cells that are capable of differentiating into myeloid cells (i.e., neutrophils, monocytes, eosinophils, basophils/mast cells), lymphoid cells (e.g., B lymphocytes), erythroid cells, and megakaryocytes. Lympho-hematopoietic stem cells express Sca-1, a marker specific for stem cells or primitive progenitors (47a). These cells are dependent for growth upon stem cell factor (SCF), also known as "c-kit ligand" (61a).

The term "erythroid progenitor" is used herein to describe cells that are capable of differentiating into erythroblasts and erythrocytes. The monoclonal antibody "ter 119" recognizes erythroid precursors and probably some nonerythroid blasts (30a). Erythroid progenitors cannot differentiate into lymphoid or myeloid cells, i.e., they are committed to the erythroid pathway of differentiation.

The term "stromal cell" refers to a type of adherent cell that normally is present in bone marrow and when cultured undergoes adipogenesis upon confluency. Stromal cells play a role in inducing the differentiation of lympoid progenitors (32a).

The term "lympoid progenitor" is used herein to mean the cell lineages, e.g., in the bone marrow, that can differentiate into early B cells when exposed to IL-7 in the presence of bone marrow stromal cells. The antibody anti-B220 (clone RA3-6B2) is specific for the B lymphocyte lineage. Lympoid progenitor cells are not capable of giving rise to myeloid or erythroid cells.

The term "myeloid lineage" is used herein to mean the cell lineage in the bone marrow that includes polymorphonuclear neutrophils, eosinophils, basophils, and mast cells, as well as the monocyte/macrophage lineage. Myeloid cells are not capable of differentiating into lymphoid cells (e.g., lymphocytes) or erythroid cells (e.g., erythrocytes).

The term "promyelocytic" refers in general to cells that are immature, partially differentiated precursors of neutrophils, basophils, and eosinophils. For the purposes of this invention, promyelocytes will be considered as a variety of hematopoietic stein cell. Promyelocytes committed to each of these three lineages are characterized by a distinct morphology and cytochemical staining reactions such as the presence of primary granules and positive chloroacetate esterase staining that exemplifies the neutrophilic promyelocytic progenitors discussed in the Examples.

The term "neutrophil progenitor" is used herein to refer to cells that are capable of differentiating only into neutrophils, and not into monocytes, mast cells, basophils, eosinophils, platelets, or erythroid cells. A representative neutrophil progenitor cell is a neutrophilic promyelocytic cell of the MPRO cell line.

The terms "basophil/mast cell" and "basophil/mast cell precursor" are used interchangeably herein to refer to the progenitor cell that can give rise to either of the two types of mast cell, namely, the common tissue mast cell which is found in loose well-vascularized connective tissue, and the blood mast cell also known as the basophil. Representative examples for distinguishing between basophils/mast cells and other stem cells include the presence of cell surface IgE receptors, synthesis and/or secretion of histamine, lack of cell surface monocyte/macrophage-specific antigens (e.g., MAC-1), and lack of neutrophIL-specific antigens (e.g., 7/4) as exemplified below (see Example 3 and Table 1).

The term "mast cell" describes a tissue bound differentiated cell with a round or oval nucleus, basophilic and usually metachromatic cytoplasmic granules containing acid mucopolysaccharide, other cytoplasmic granules containing histamine, and cell surface IgE receptors.

The term "basophil" describes a blood borne differentiated cell with a more polymorphic shape than the mast cell, but containing basophilic metachromatic cytoplasmic granules with acid mucopolysaccharride and cytoplasmic histamine granules, and cell surface IgE receptors that are similar to those found in the tissue mast cell.

The term "basophilic/mast cell" is used to refer to a cell having the phenotype of a basophil or a mast cell.

The term "dominant negative suppressor of RARs" is used herein to refer to a non-natural RAR such as an RAR encoded by a genetically altered RAR nucleotide sequence. The subject non-natural RARs are functionally and/or structurally related to RARs but differ from natural RARs by virtue of a common ability to suppress the activity of a natural RAR in a cell, and in a dominant negative manner. RARα403 is a representative example of a dominant negative suppressor of natural RARα in a cell. The inventors envisage that, in addition, retinoic acid receptors other than RARα (i.e., RXRs) may be useful in the methods of the invention and that these non-natural dominant-negative suppressors of RXRs will share the common ability to dominantly suppress the activity of a natural RAR in a cell.

The term "RXR" as used herein refers to a retinoid X receptor as described in Mangelsdorf et al. (1990) *Nature* 345:224–229, and Mangelsdorf et al. (1991) *Cell* 66:555–561 (37a, 37b). RXR is a recently recognized distinct nuclear retinoic acid receptor that is incapable of high affinity binding of retinoic acid but is capable of binding retinoic acid at low affinity (i.e., higher concentrations of retinoic acid such as $>10^{-6}M$). The RXR:retinoic acid complex is capable of activating target genes such as the cellular retinol binding protein type II by binding to response elements that are distinct from those that are regulated by RARs.

Figure 16A:
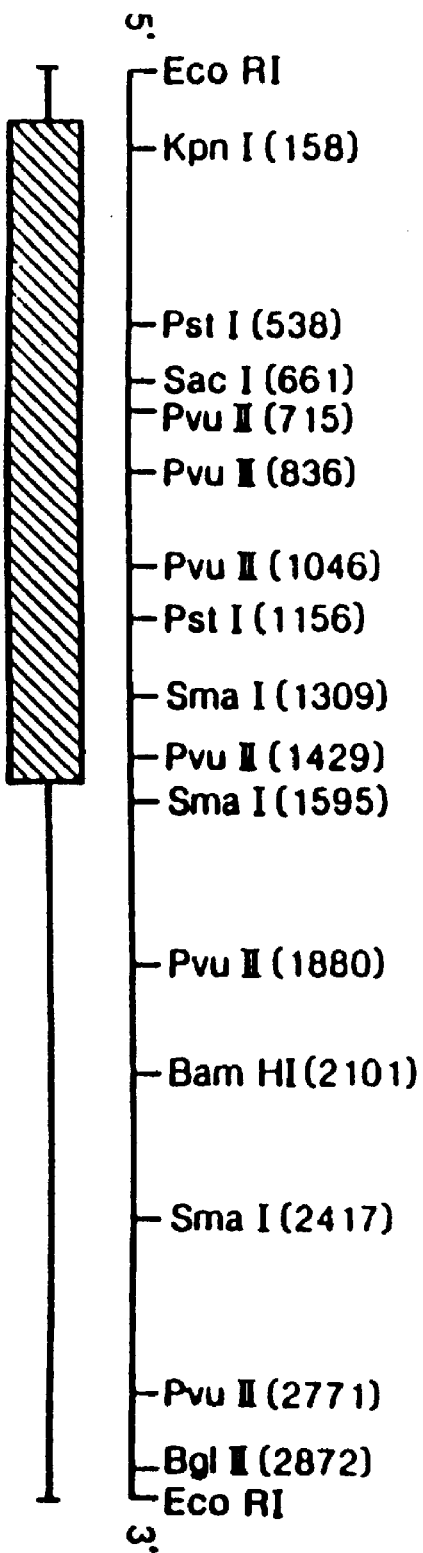
FIGS. 16A (Prior Art) shows the structure and restriction sites of λhK1R clone containing RARα (cross hatched bar) as described (25).
Figures 18A, 18B, 18C:
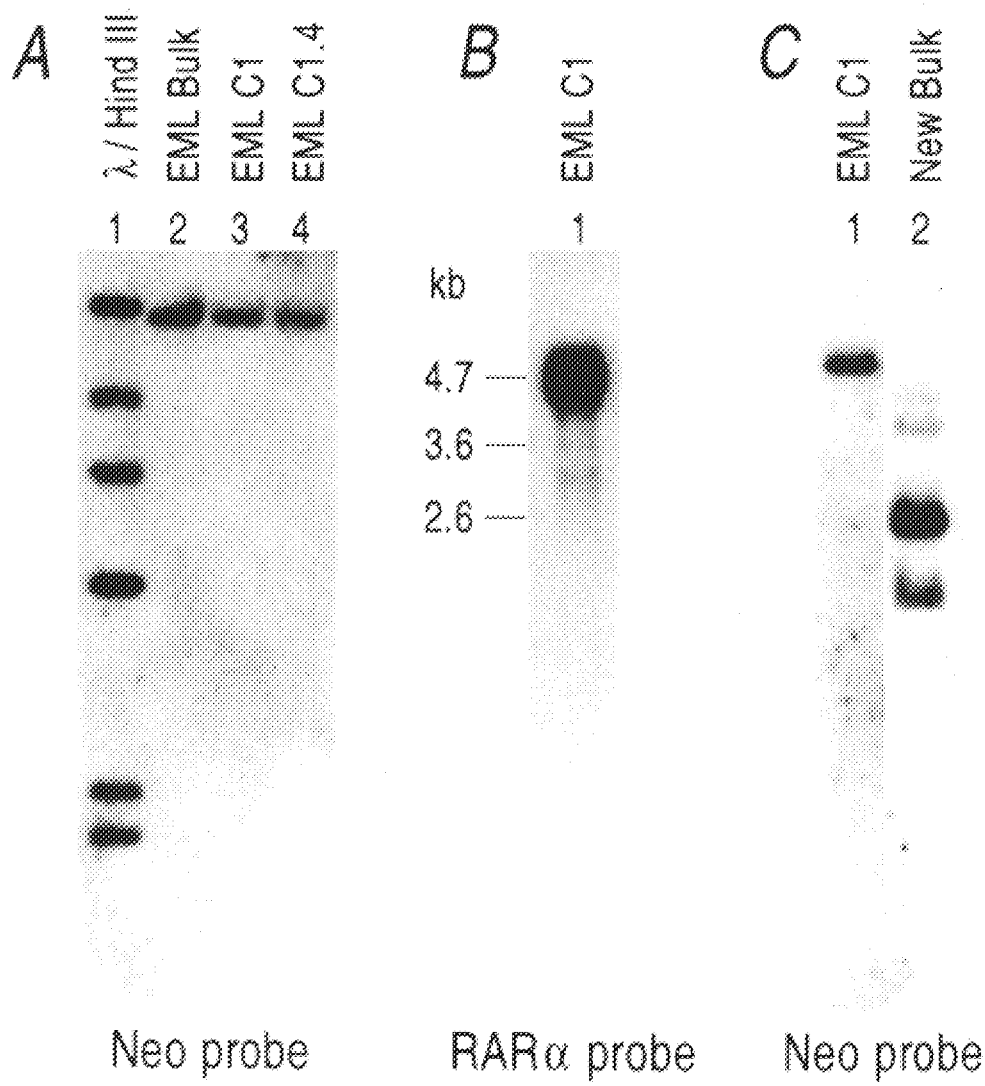
FIGS. 18(A)–18(C) demonstrate that bone marrow cells transduced with LRARα403SN contain and express construct sequences that were derived from the transduced construct.

The term "dominant negative suppressor" is used herein in the manner accepted in the art, and as described in (26). The subject "dominant negative suppressors of the RARs" are commonly recognized by their ability to suppress a retinol compound induced RAR-specific structural or functional event in a cell. Representative examples of genetically altered RAR nucleotide sequences include sequences that have been mutated, deleted, inverted, or otherwise modified to create a dominant negative suppressor construct include portions of the RARα RA binding region (e.g., nucleotides 692 to 1395 of RARα), a mutant RARα DNA binding region (e.g., nucleotides 364 to 564 of RARα), a mutant RARα N-terminal region (e.g., nucleotides 103 to 363 of RARα), a mutant RARα C-terminal region (nucleotides 1396 to 1488 of RARα), all as depicted in FIG. 16B. A representative example of a dominant negative suppressor of RARα nucleotide sequence that is suitable for introduction into a hematopoietic cell is provided by retroviral vector LRARα403 (see FIG. 1B).

The term "retinol compound" as used herein is intended to mean provitamin A, vitamin A and its derivatives, and metabolites including retinoids. Representative examples of important provitamin A carotenoids include: β-carotene; α-carotene; γ-carotene; cryptoxathin; echinenone; $2^1$-apo-β-carotenal ($C_{37}$); $8^1$-apo-β-carotenal ($C_{30}$); $10^1$-apo-β-carotenal ($C_{27}$); and $12^1$-apo-β-carotenal ($C_{25}$). Representative compounds in the vitamin A group include: all-trans-Retinol; all-trans-Retinaldehyde; ll-cis-Retinaldehyde; all-trans-Retinoic acid; all-trans-Dehydroretinol; all-trans-Dehydroretinaldehyde; ll-cis-Dehydroretinaldehyde; and all-trans-Dehydroretinoic acid. Representative retinoids include: Axerophthene; 13-cis-Retinoic acid (RA); Trimethymethoxyphenyl (TMMP) analog of RA; Retinal; β-all-trans-Retinoic acid (RA); 10-Fluora-TMMP analog of RA; Retinol; 7,8-Dehydro analog of RA; TMMP analog of ethyl retinoate; Retinyl methyl ether; 5,6-Epoxy analog of RA; TMMP analog N-ethyl-retinamide; Retinyl methyl thioether; 4-Oxo analog of RA; N-Methyl-dimethyldioxolan-retinamide; Retinyl n-butyl ether; Phenyl analog of RA; N-(O-Carboxyphenyl)-retinamide; Retinyl tert-butyl ether; Pyridyl analog of RA; N-(p-Carboxyphenyl)-retinamide; Retinyl acetate; Trimethylthiophene (TMT) analog of RA; N-Benzoyl-retinylamine; Retinyl palmitate; Dimethylacetyl cyclo-pentenyl (DACP) analog of RA; and Retinylidene ethylcanoacetate.

The term "Type I (also known as immediate) hypersensitivity reactions" is used to refer to immune reactions resulting from triggering of IgE that is bound to cellular receptors predominantly on the surface of mast cells, degranulation of the mast cells with release of mediators (e.g., histamine and serotonin), and with the potential involvement of basophils that may contain histamines. Representative examples of Type I hypersensitivity reactions include asthma, allergy, hay fever, allergic rhinitis, allergic contact dermatitis, urticaria, angioedema, allergic drug reactions, and reactions in the gastrointestinal tract to parasites such as helminths.

The term "mast cell proliferative disease" refers to diseases whose etiology lies in over production of mast cells. Representative examples include urticaria pigmentosa, mastocytoma, diffuse cutaneous mastocytosis, systemic mastocytosis, and mast cell leukemias.

The various cells of the blood and immune system originate from a single type of primitive self-renewing stem cell that is present in the body in very small numbers. As they divide, these primitive cells (the lympho-hematopoietic stem cells) generate other kinds of hematopoietic stem cells that have fewer options for differentiation than possessed by the parent stem cells. Through additional rounds of division and differentiation, each type of stem cell gives rise to even more differentiated varieties of stem cells that are committed to single hematopoietic lineages (e.g., neutrophilic progenitor cells). Eventually through this process the various types of stem cells produce the numerous kinds of fully differentiated cells that populate the bloodstream and lymphoid organs. Many if not all of the steps in this process are controlled by a variety of growth factors that provide the signals for differentiation. Examples of such growth factors are SCF, IL-3, IL-7, erythropoietin, GM-CSF, and so on. Retinoic acid and its derivatives play a role in the differentiation of some hematopoietic cells. When grown in culture, hematopoietic cells usually require that essential growth factors be present in the culture medium in order to sustain cell division and/or differentiation. In some cases where the precise growth factor requirements of a cell type have not been defined or are not easily available, serum or conditioned medium may be used as a source of growth factors. For example, WEHI conditioned medium may be used to induce differentiation of CFU-GM from cultured lympho-hematopoietic stem cells. As hematopoietic differentiation is not fully understood, large numbers of presently unknown growth factors undoubtedly await discovery.

The invention provides methods for the immortalization of lympho-hematopoietic stem cells. The immortalized progenitors, exemplified by the EML Cl continuous cell line (ATCC No. CRL 11691, deposited Jul. 25, 1994, 12301 Parklawn Drive, Rockville, Md., U.S.A., 20852), proliferate as stem cell factor-dependent EML cells which spontaneously generate pre-pro-B lymphocytes, erythroid and myeloid progenitors. Upon stimulation of EML cells with IL-7 and stromal cells, the pre-pro-B lymphocytes express RAG-1 and undergo D–J rearrangements of the immunoglobulin heavy chain genes. With Epo stimulation of immortal lympho-hematopoietic stem cells, the erythroid progenitors proliferate and differentiate into red blood cells. The present invention also provides methods for establishing continuous GM-CSF (or other hematopoietic growth factor) dependent neutrophil progenitor cell lines made up of myeloid cells that are able to differentiate upon induction with a retinol compound into neutrophils but not monocytes, eosinophils, mast cells, or basophils. Prior to introducing the immortalizing gene, recipient hematopoietic cells (e.g., bone marrow cells) may be treated with 5-fluorouracil to enrich for the normally quiescent lympho-hematopoietic stem cells. The subject methods share in common the step of introducing a dominant negative suppressor of RARs into a cell population containing hematopoietic stem cells, e.g., lympho-hematopoietic cells and promyelocytic cells. Sources of recipient hematopoietic cells populations suitable for establishing continuous hematopoietic cell lines include bone marrow cells, fetal spleen, fetal liver cells, bone marrow aspirates, peripheral blood mononuclear cell fractions from blood, spleen cells, and existing multipotent hematopoietic cell lines. In all cases the recipient hematopoietic cell populations must contain cells that are capable of differentiation into lymphoid, erythroid, or myeloid lineage cells. The dominant negative suppressor of RARs can be introduced into the recipient hematopoietic cells by any of a variety of commonly employed genetic techniques, e.g., by transfection of plasmid DNA or by transduction with retroviral vectors. The introduction of nucleotide sequences for the dominant negative suppressor of RARs and selectable marker is preferably accomplished in a simultaneous manner; for example, by simultaneously transfecting the RARs suppressor and the selectable marker into cells; or by using a retroviral vector containing in serial array an LTR (L), the dominant negative suppressor RARs nucleotide sequence (such as RARα403), and a selectable marker such as neo (N), hygro (HPT), or his (HIS), followed by a polyA tail. The selectable marker permits enrichment of the transfected or transduced cell cultures for cells that have properly taken up and incorporated the nucleotide sequences encoding the suppressor of RARs and the selectable marker. Those skilled in the art will recognize that a variety of methods may be used for such enrichment, including selecting for drug sensitivity (e.g., using G418 to select for neo, or Hygromycin to select for hpt) and screening for antigen expression (e.g., using fluorescence activated cell sorting (FACS) and a nucleotide sequence encoding an antigenic marker). When the object of an experiment is to immortalize the lympho-hematopoietic stem cells, transduction with RARα403 need not be accompanied by selection because lympho-hematopoietic stem cells that have integrated the transduced gene acquire a growth advantage that makes selection unnecessary.

The method for creating a continuous SCF-dependent lympho-hematopoietic progenitor cell line comprises infecting bone marrow or other suitable cells with the retroviral vector LRARα403SN and subsequently culturing the cells in a medium comprising SCF. A representative example of cell lines created by this method is the EML Cl cell line derived from bone marrow of $BDF_1$ mice. Cell lines such as EML C1 can be reproducibly produced by infecting $BDF_1$ mouse bone marrow cells with retroviral producer cells in a serum-supplemented culture medium capable of supporting cell growth for a time sufficient to allow retroviral infection of the bone marrow cells, e.g., about two days. When infected cells are subcultured every 2–3 days for one to two months, EML-type cells become the dominant cell type. Subcloning of the cells can be carried out using standard methods, e.g., by using limiting dilution cloning in liquid or semisolid culture medium in 96-well culture plates or other standard methods of cell cloning. Selection with a drug such as G418 or screening (e.g., by FACS) can be applied, but is optional.

The invention provides methods for using the continuous lines of lympho-hematopoietic stem cells for producing cultures in which a substantial proportion, e.g., 10% or more, of the cells differentiate into erythroblasts and erythrocytes. To achieve this result, EML cells are cultured with sufficient amounts of SCF and Epo to induce formation of erythroid cells, e.g., 100–300 ng/ml and 4–12 ng/ml, respectively. To assay for BFU-E, these cells may be cultured in the presence of SCF plus Epo (5–15 units/ml) in a semi-solid medium such as 0.8% methylcellulose, soft agarose, or other equivalents known to those skilled in histological methods.

The invention moreover provides a means of stimulating division and differentiation of the B220-positive pre-pro-B cells present in EML cell cultures. For this induction, SCF must be removed from the medium, e.g., by washing the cells, and the cells co-cultivated in the presence of IL-7 (50–150 units/ml) with bone marrow-derived stromal cells. Stromal cell lines such as W20 (Tsai, 1986) or equivalent cell lines can be used for this purpose. Under these conditions, the B220-positive EML cells will proliferate and some of them will express the RAG-1 gene and initiate D–J rearrangements, two events that signify B-cell differentiation.

Methods are also provided for inducing CFU-GM from EML cells. To accomplish this, EML cells are cultured in the presence of SCF, then treated with RA at various concentrations (e.g., $10^{-5}$–$10^{-6}$) for about 2–5 days. For CFU-GM assay, the cells are then washed to remove RA and recultured with GM-CSF (5–15 ng/ml) in methylcellulose, soft agarose, or an equivalent cloning substrate.

The invention also provides methods for establishing neutrophilic cell lines from EML cells. Following induction with RA plus IL-3, the cells are washed to remove exogenous RA then cultured with about 5–15 ng/ml of GM-CSF and a level of retinoic acid of less than about $10^{-8}$M to about $10^{-9}$M. While most cells will die as a result of this treatment, CFU-GMs will proliferate and differentiate into promyelocytes, neutrophils, and macrophages. After about 2–3 weeks of culture, most of the growing cells will be GM-CSF-dependent cells. Individual CFU-GM colonies can be obtained from such cultures by cloning them in methylcellulose or an equivalent substrate supplemented with GM-CSF. Promyelocytic cell lines so established are designated EPRO (for EML-derived promyelocytes).

Figure 23A:
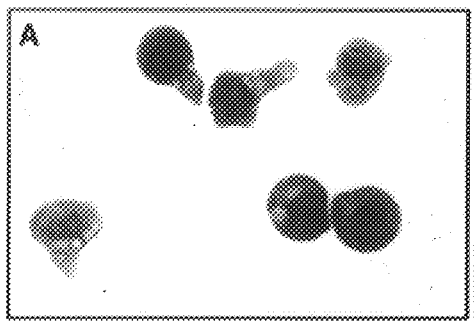
FIGS. 23(A–H) photographically depicts EML cells in various stages of differentiation.
FIG. 23(B) illustrates an aggregate of hemoglobinized erythroblasts that appeared 3–5 days after Epo was added to a liquid culture of EML.
FIG. 23(C) illustrates mast cells seen in a culture of EML that had been stimulated with IL-3.
FIG. 23(D) shows megakaryocytes in a culture of EML cells stimulated with SCF, IL-3, Epo, IL-6, and IL-11.
FIG. 23(E) illustrates B220-positive proliferating cells that have remained attached to the stromal cells added for induction of differentiation.
FIG. 23(G) depicts GM-CSF-dependent cells blocked at the promyelocyte stage, and which have been designated as "EPRO" for EML-derived promyelocytes.
FIG. 23(H) shows EPRO cells that have been induced to differentiate synchronously into mature neutrophils by being treated with a supraphysiological concentration of RA ($0.5$–$1.0\times10^{-5}$M).
Figure 23B:
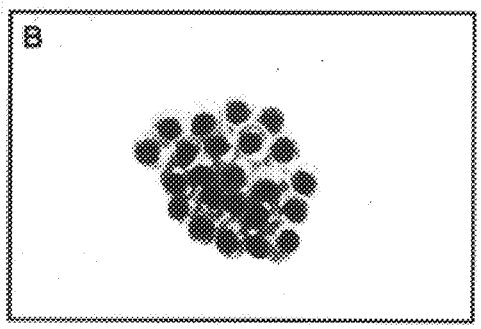
Figure 23C:
Figure 23D:
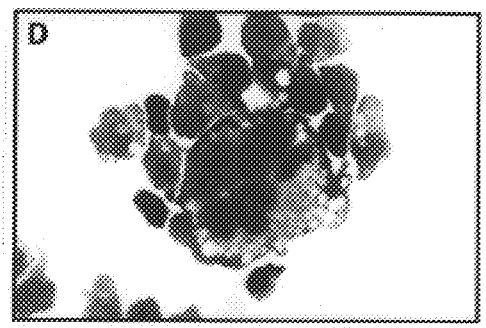
Figure 23E:
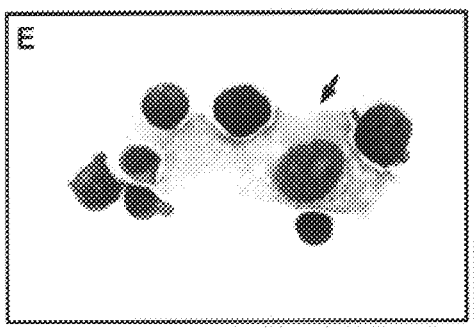
Figure 23F:
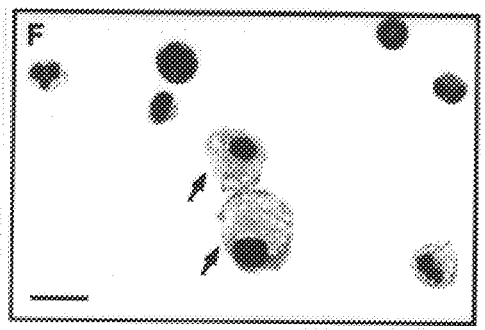
Figure 23G:
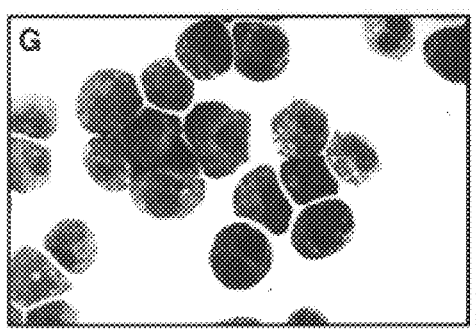
Figure 23H:
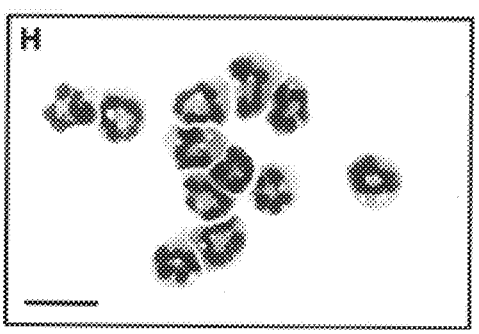
Figures 24A, 24B, 24C, 24D:
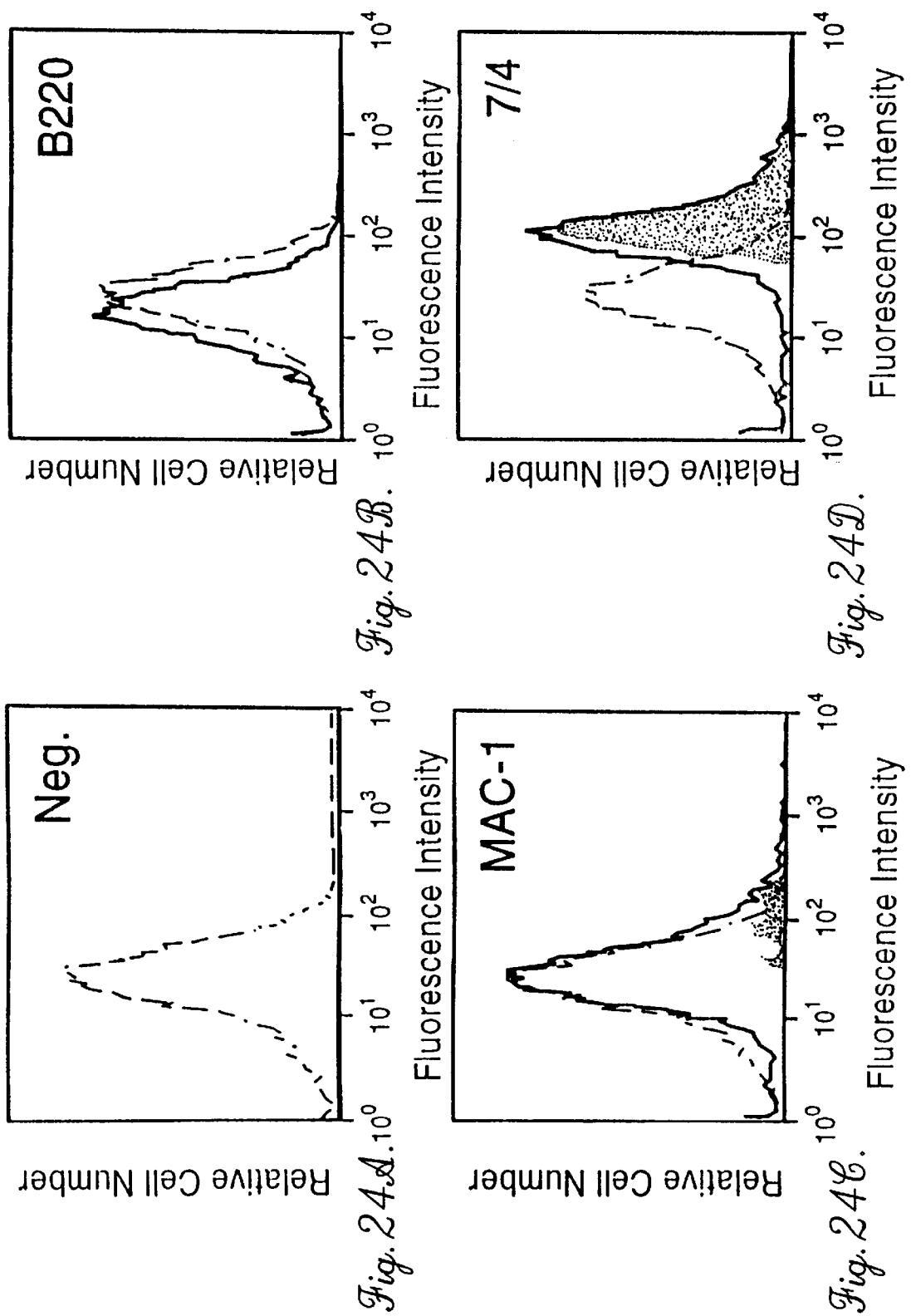
FIGS. 24(A–D) shows the results of a flow cytometry analysis of cell surface markers of a representative EPRO cell line (C1). The monoclonal antibodies used for the flow cytometry are defined above in the description of FIG. 19.
FIG. 24(E) is a Southern blot showing that EPRO C1 cells have the same proviral integration site as EML C1 and EML C1-derived B-cell precursors supported by the W20 stromal cell line and IL-7.
Figure 25:
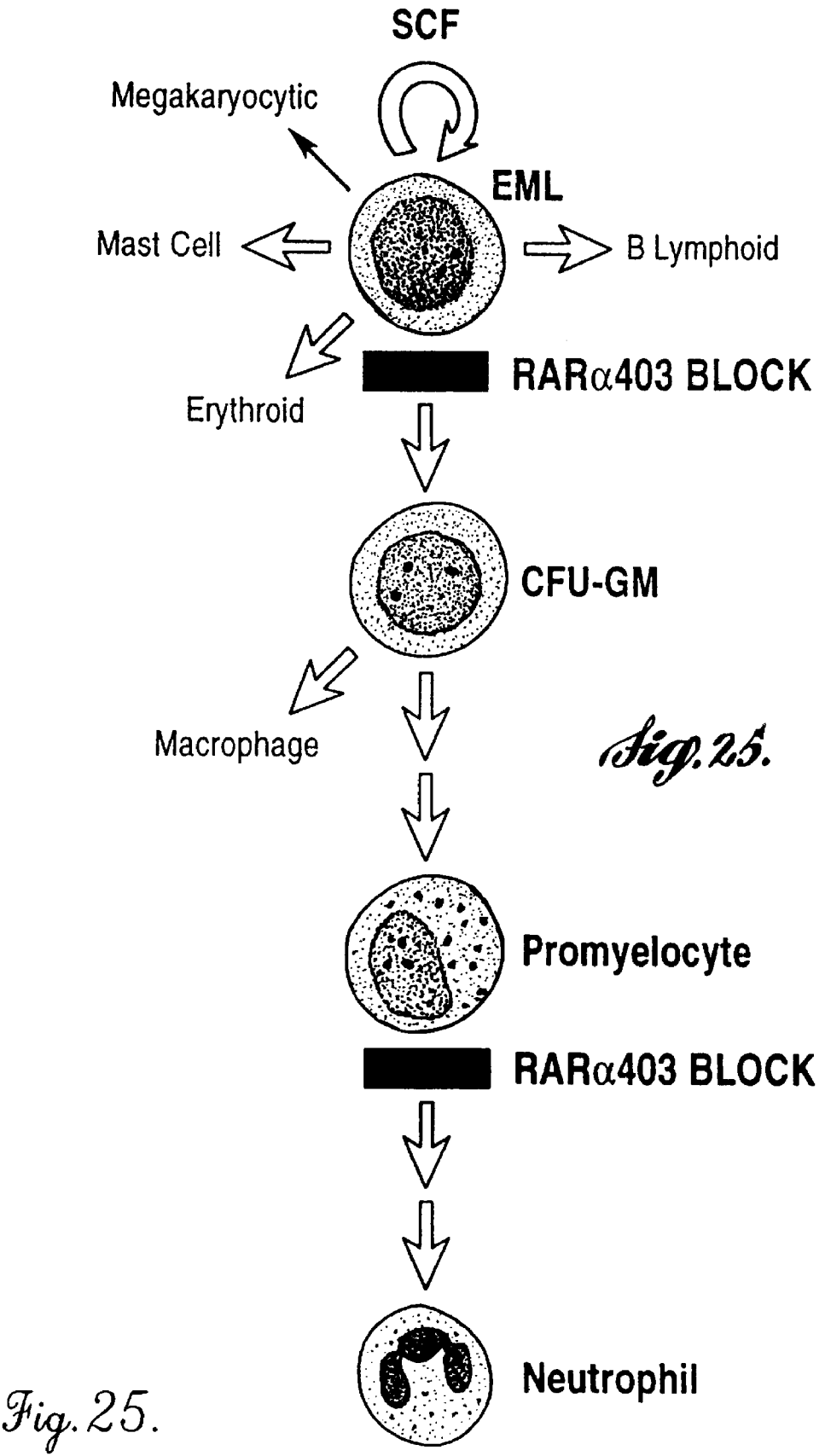
FIG. 25 diagramatically summarizes the effects of the dominant negative RARα403 gene on myeloid lineage development in EML cells.

EML cells also can be induced with the present methods to yield mast cells and megakaryocytes. When EML cells are stimulated with IL-3 in liquid culture with or without liquid culture, mast cells will appear (FIG. 23(C)). Upon simultaneous stimulation of EML cells with SCF, IL-3, Epo, IL-6, and IL-11, occasional megakaryocytes are detected (FIG. 23(D)).

The subject method for establishing a continuous GM-CSF dependent neutrophil progenitor cell line directly from bone marrow, e.g., MPRO cells, involves culturing the genetically altered promyelocytic cells, i.e., from the genetic transfer step, for a sufficient period of time to allow growth, and in a culture medium containing a GM-CSF and an agent allowing for selective growth of the genetically altered promyelocytic cells (e.g., G418 in the case of neo). The selection (e.g., with G418) or screening (e.g., by FACS) is optional. The neutrophil progenitor cells produced by this method have the common property of being inducible by retinol compounds to differentiate into only neutrophils, but not into monocytes, basophils, or mast cells. Induction to differentiate into neutrophils is accomplished by adding a retinol compound to the culture medium in an amount and for a time sufficient to induce the differentiation. Thereafter, a continuous GM-CSF dependent neutrophilic promyelocyte cell line can be established by culturing the cells in the presence of GM-CSF for a period of time sufficient to allow all terminally differentiated cells to die out; three weeks is usually sufficient. For example, when retinoic acid is used, about $10^{-5}$M to about $10^{-6}$M concentrations are sufficient to induce MPRO cells to differentiate into neutrophils within 72 hours in culture. Those skilled in the art will recognize that a variety of retinol compounds may be used, and that the amounts and times may vary slightly depending upon the properties of the compound and the cell line.

The invention also provides a method for establishing a continuous IL-3 (or other hematopoietic growth factor) dependent mast cell and basophil progenitor cell line made up of myeloid cells that are capable of differentiating preferentially into mast cells and basophils. A representative example is the IL-3-dependent LRARα403-transduced FDCP nix A4 cells, which are derived from IL-3-dependent FDCP mix A4 cells which are multipotent cells derived from mouse bone marrow cells. The subject method involves genetically altering the FDCP mix A4 cells by introducing nucleotide sequences encoding a dominant negative suppressor of RARs and also a selectable marker. Secondary cell cultures of the genetically altered FDCP mix A4 cells are IL-3 dependent and are maintained in medium containing IL-3. The subject method produces cell cultures that are initially about 50% mast cells and basophils, and as the cultures are maintained in IL-3 for several weeks that percentage drops and becomes stable at about 30% to about 40% mast cells and basophils. The remainder of the cells in the cultures are (at all times) less than about 2% neutrophils and monocytoid cells and about 58% to about 68% undifferentiated cells with no recognizable microscopic features. We observed that removal of IL-3 from the culture medium and addition of GM-CSF forced the percentage of neutrophils to somewhat higher levels.

The subject cultures can of course be enriched to obtain substantially pure cultures. For EML cells, FACS sorting or other routine methods can be used to obtain populations of greater than about 80% to about 95% of the pluripotential lympho-hematopoietic stem cells (Sca-1-expressing cells), erythroid progenitors (ter 119-expressing cells), pre-pro-B cells (B220-expressing cells), or macrophage/neutrophil lineage cells (7/4- or Mac-1-expressing cells). Subject cultures moreover can be similarly enriched to yield greater than about 80% to about 95% mast cells and basophils by FACS sorting, cloning, and other routine methods. Thereafter, a continuous IL-3 dependent basophil/mast cell line can be established by culturing the cells in the presence of IL-3. Representative basophil/mast cell lines produced by the subject method have been maintained in the continuous presence of IL-3 for a period of nine months.

The subject EML cell lines provide a valuable resource for biomedical purposes. These are the only known SCF-dependent cell lines with both lymphoid and myelo-erythroid potentials. These cells could play a life-saving role in patients whose hematopoietic cells have been ravaged by disease or have been depleted by cancer therapies. Reconstitution of cancer patients with cells of the present invention might enable the beneficial use of otherwise fatal doses of chemotherapies. When maintained in SCF, EML cells provide a model in vitro system for studying stem cell development. Moreover, the cells can be used for developing diagnostic assays for screening potential therapeutic agents for their effectiveness in killing or inducing differentiation in this cell type. EML cells furthermore can serve as a source of cells in the erythroid, myeloid, and B-cell lineages which in turn can be used for development of diagnostics and therapeutics. Uses of these cells include: a) use in molecular assays for identifying specific transcription factors and genes involved in terminal differentiation of the various cell types in the several lineages derivable from the cells; b) use as a source of novel or known growth factors and their receptors; c) use as target cells in assays for growth factors that specifically interact with the cell lineages present; d) use for identifying any biologically active molecules that may interact with or specifically affect the cell lineages present in EML cell lines; e) use in producing gene products that can be effectively expressed only in cells belonging to erythroid, myeloid, or B-cell lineages; f) use in developing monoclonal antibodies specific for stem cell surface antigens; g) identification of new adhesion molecules that mediate the binding of bone marrow stem cells to stromal cells (such adhesion molecules may subsequently be used to purify stem cells); h) molecular cloning of stem cell receptors for adhesion molecules described in (f); h) production of new hematopoietic stem cell- or progenitor cell-specific monoclonal antibodies; i) reconstitution of lympoid and myelo-erythroid lineages in patients whose stem cells have been damaged due to chemotherapy or radiation therapy.

The subject neutrophilic promyelocytic cell lines (e.g., MPRO, EPRO, and GMB) find a variety of uses. For instance, the neutrophilic promyelocyte cell lines may serve as useful models in studying the pathogenesis of human acute promyelocytic leukemia (APL), and in screening assays to identify candidate cytotoxic anti-cancer therapeutic agents, as well as therapeutic agents that induce cytodifferentiation in APL cells. Other uses include: a) use of the subject cells in molecular assays for identifying specific transcription factors and genes involved in terminal differentiation of neutrophils; b) use of the cells as sources of novel growth factors (cytokines) and their receptors; c) use of the cells as target cells in screening assays for identifying novel growth factors produced by other cells (e.g., bone marrow stromal cells) and/or for determining the combinations of known growth factors that may be optimal for terminal differentiation of neutrophils; d) use of the cells for identifying bactericidal peptides, enzymes, procoagulants and anticoagulants (as well as other biologically active molecules); and e) use of the cells in producing gene products that can be effectively expressed only in neutrophilic promyelocytes.

The mast cell and basophil precursor cell lines produced by the subject methods provide cells useful in screening assays for identifying candidate therapeutic agents for treating immune immediate hypersensitivity reactions (e.g., allergy, asthma, basophil hypersensitivity reaction). Other uses currently envisaged for the subject mast cell and basophil precursor cell lines include: a) use of the cells in molecular assays for identifying specific transcription factors and genes involved in terminal differentiation of mast cells and basophils; b) use of the cells as sources of novel growth factors and receptors and other biologically active molecules such as anticoagulants and vasoactive peptides; and c) use of the cells as target cells in screening assays for identifying novel growth factors produced by other cells (e.g., bone marrow stromal cells) and/or for determining the combinations of known growth factors that may be optimal for terminal differentiation of mast cells and basophils.

A representative example of a screening assay using the subject neutrophilic progenitor cell line to select a candidate therapeutic agent active against APL involves the following steps: a) grow the cells in a murine GM-CSF-containing medium; b) add a candidate compound to the cell culture at various concentrations; c) include a solvent vehicle control; d) change the medium and add fresh aliquots of the candidate compound as needed; e) prepare a cytospin preparation and stain with Wright-Giemsa stain; f) do a differential count to determine the percentage of differentiated neutrophils; and g) construct a dose-response curve of the candidate compound and make comparisons to known therapeutic compounds.

A representative example of a screening assay using the subject mast cell and basophil progenitor cell line to select a candidate therapeutic agent active against these cell types involves the following steps: a) culture the cells in a medium containing murine IL-3; b) add a candidate compound at various concentrations; c) include a solvent vehicle control; d) change medium and add additional fresh aliquots of the candidate compound as needed; e) do a differential count to determine the percentages of differentiated mast cells/basophils; and f) construct a dose-response curve of the candidate compound, and make comparisons as above.

The invention also provides genetic screening assays for identifying a patient with defects in the RARα gene. The assays involve identification of mutant RARα genes that are capable of acting as dominant negative suppressors of an RARα gene in the patient. A representative assay involves the steps of: collecting a sample of cells from a patient; isolating nucleic acid from these test cells; comparing an RA region or a DNA binding region nucleotide sequence of the isolated test nucleic acid with the RA region or the DNA binding region nucleotide sequence of a normal control RARα nucleic acid; and determining, if a difference exists between the test and the control nucleic acids, that the test nucleic acid sample from the patient may contain an RARα gene defect that could act as a dominant negative suppressor of an RARα gene in the patient. Confirmation that the test DNA contains a dominant negative suppressor RARα gene defect can be conveniently determined using methods as described in the Examples below.

EXAMPLE 1

A truncated RARα construct exhibits dominant negative activity.

As detailed in Experimental Procedures section (following Examples 1–6, below), an RARα cDNA was prepared that contained a truncation of the sequences coding for the C-terminal 59 amino acids as well as a portion of the 3' untranslated region. This truncated cDNA (designated RARα403) encodes a peptide of 403 amino acids containing the N-terminus, the DNA-binding domain, and part nucleotide sequence evidence of the hormone-binding domain of RARα (FIGS. 1A and 1B). The RARα403 was inserted into the retroviral vector LXSN (FIG. 1C) to generate the recombinant vector designated LRARα403SN (FIG. 1D).

To determine whether the truncated RARα403 construct exhibits dominant negative activity with respect to the normal RARα, we performed transactivation assays in mouse NIH3T3 tk- cells. When an expression vector harboring the normal RARα gene (pEMSV-RARα) was co-transfected with a chloramphenicol acetyl transferase (CAT) reporter construct pTRE-CAT containing a synthetic thyroid hormone/retinoic acid responsive element (TRE) (54), there was RA-induced transactivation of the CAT reporter gene (FIG. 2A, lanes 5 and 6). In contrast, when both pEMSV-RARα and the mutant LRARα403SN construct were co-transfected into the same target cells, there was a dose-dependent suppression of this RARα-mediated transactivation (FIG. 2A, lanes 6–10).

Figure 2B:
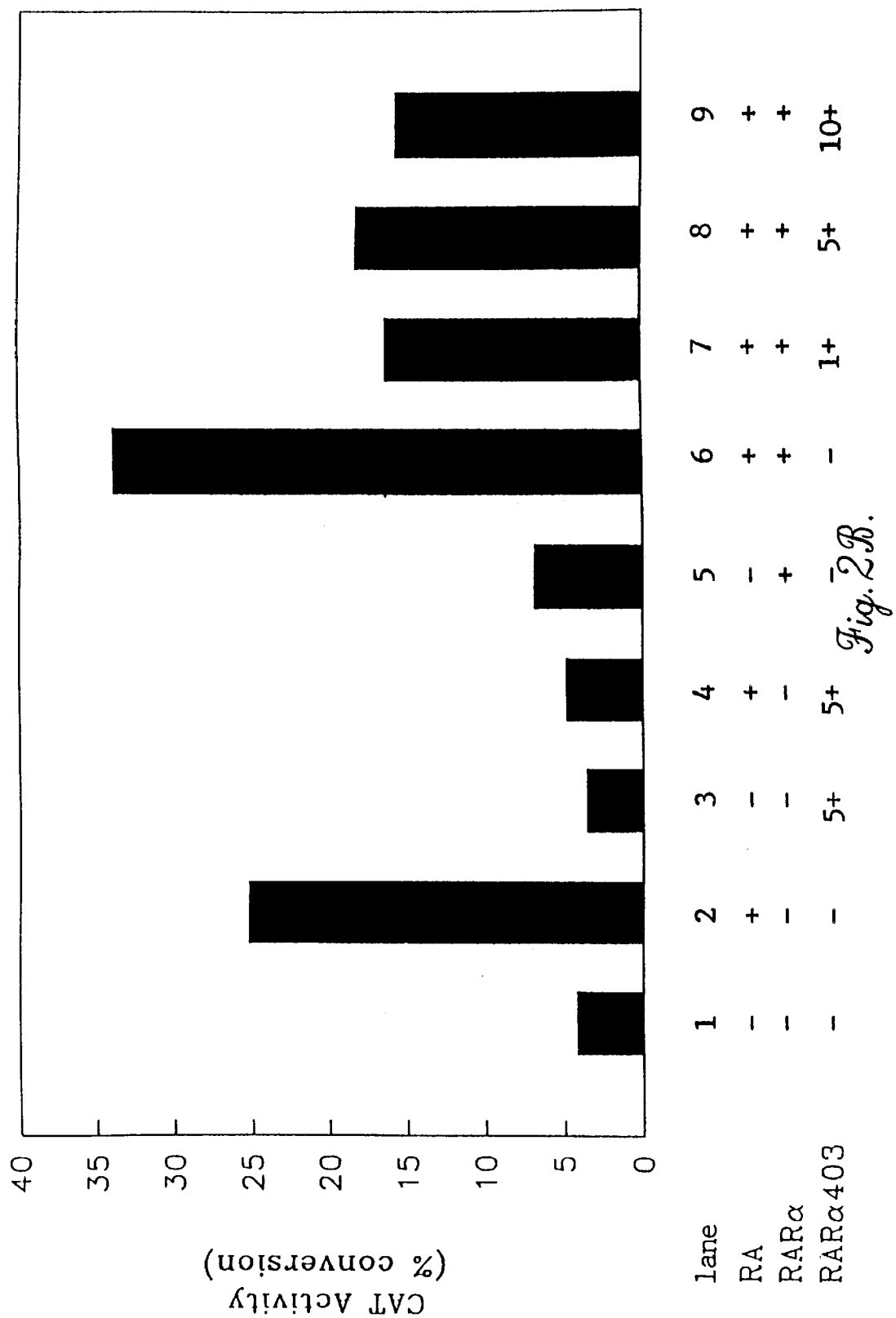

An RARα/RARα403 DNA ratio of 1:6 suppressed most of the activity of the normal RARα. When this experiment was performed using a different reporter, i.e., pRRE-CAT which harbors the natural retinoic acid response element (RRE) of RARα (20), there was prominent suppression of the endogenous RAR activities (FIG. 2B, lanes 3–4) and partial suppression of exogenous RARα activity (FIG. 2B, lanes 6–9). These results indicate that the RARα403 construct exhibits dominant negative activity with respect to the normal RARα in mouse fibroblasts.

To determine whether this same RARα403 construct also exhibits dominant negative activity in hematopoietic cells, we performed transient expression assays in the mouse hematopoietic cell line FDCP mix A4 (described below) by electroporation. Although the RARα403 construct suppressed some endogenous RARα activities in this cell line (data not shown), the extremely low efficiency of gene transfer achievable by electroporation in these target cells (estimated to be $\frac{1}{10,000}$ of that of NIH3T3) made them less than ideal for adequately assessing the suppressing potential of RARα403 by transient expression. To further examine the dominant negative function of RARα403 in hematopoietic cells, we utilized retrovirus-mediated gene transduction to introduce this mutant receptor into the HL-60 human promyelocytic leukemia cell line (6). RA induces neutrophilic differentiation of HL-60 cells (3) and this response is mediated directly through RARα (8). As detailed in the Experimental Procedures, we infected HL-60 cells with the amphotropic LRARα403SN retroviral vector (FIG. 1D) and utilized Northern blot analysis to identify retroviral vector-infected HL-60 clones that expressed the mutant RARα403 mRNA. As a control we also infected HL-60 with the LXSN retroviral vector which confers G418 resistance but lacks a cDNA insert (FIG. 1C). We then compared the differentiative response of these different retroviral vector-infected HL-60 clones to RA. The control LXSN-infected HL-60 clones (D.1 and D.2) exhibited a similar response to RA as previously detailed for the parental HL-60 cells (3), with 80–90% of the cultured cells undergoing morphologic differentiation to mature neutrophils after a 5-day exposure to $10^{-6}$M RA (FIG. 3). In contrast, the LRARα403SN-infected HL-60 clones (D.2 and D.5) exhibited marked blunting of this differentiative response to RA, with no more than 20–25% of the cells differentiating to neutrophils after exposure to concentrations of RA up to $10^{-5}$M (FIG. 3). These results indicate that the truncated RARα403 construct also exhibits dominant negative activity in the HL-60 hematopoietic cell line, and that its expression is not lethal in these particular neutrophil progenitors.

EXAMPLE 2

Characteristics of FDCP mix A4 cells.

Figure 4A:
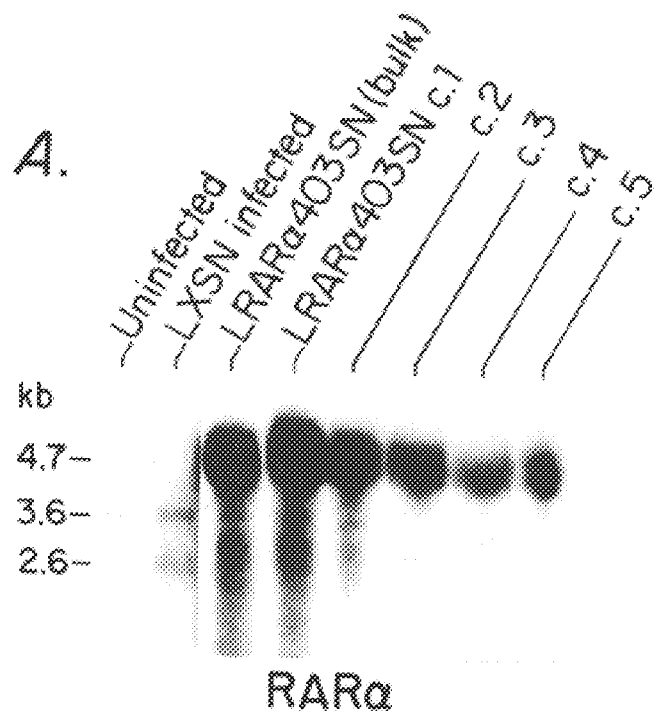
FIGS. 4A and 4B graphically shows high level expression of LRARα403SN and GATA-1 in infected FDCP mix A4 cells. RNAs were prepared from uninfected, control (LXSN) -infected and LRARα403 SN-infected FDCP mix A4 bulk cultures and from five clonal lines (labeled as LRARα403SN c.1–c.5) and subjected to Northern blot hybridization. Ten μg of total RNA was applied to each lane and hybridized to the indicated probes.

To examine the impact of the dominant negative RARα403 on the commitment and differentiation of multipotent hematopoietic progenitors, we utilized the FDCP mix A4 cell line. This interleukin-3 (IL-3) dependent cell line was established from a murine long-term bone marrow culture and behaves like normal hematopoietic stem cells in many respects: it is non-leukemogenic, responds to several hematopoietic growth factors in a physiologically relevant manner, and spontaneously generates progenitors committed to different hematopoietic lineages (31, 49). When cultured in a medium containing horse serum and WEHI 3B cell line conditioned medium (as a source of IL-3), the line maintained in our laboratory consists mainly of undifferentiated blasts (FIG. 5A) but spontaneously differentiates into neutrophils and monocyte/macrophages (about 10–30% combined) and to a much lesser extent into mast cells/ basophils (1–2%). Northern blot analysis indicates that these cells express the endogenous 3.6 and 2.6 kb RARα mRNA transcripts (FIG. 4A, lane 1). Thus this multipotent hematopoietic cell line appears to be well suited for investigating the impact of the dominant negative RARα403 on hematopoietic differentiation.

Figure 4B:
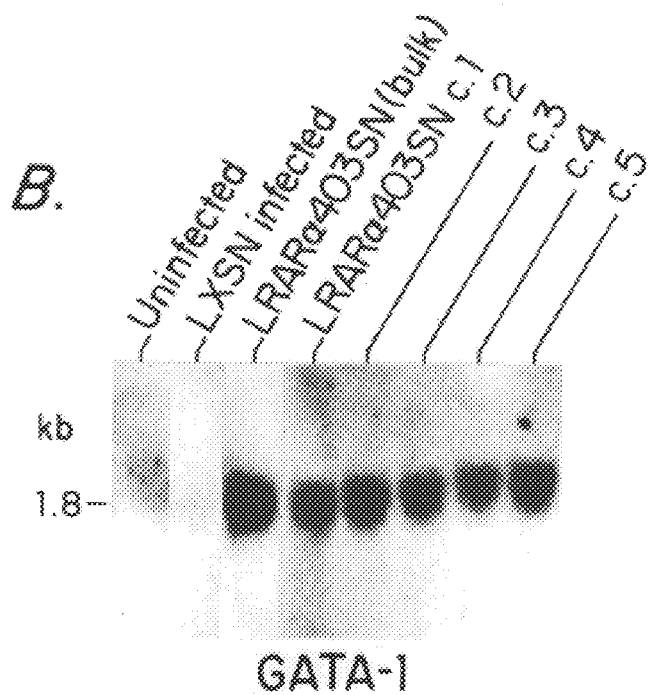

FIGS. 4A and 4B show graphically the high level RNA expression of RARα403SN and GATA-1 observed in LRARα403SN-infected FDCP mix A4 cells. The level of full-length messenger RNA (i.e., 4.7 kb) from LRARα403Sn is shown in FIG. 4A. (The RARα probe also detects the endogenous mouse RARα a mRNA at 3.6 kb and 2.6 kb.) In FIG. 4B, expression of GATA-1 mRNA (i.e., 1.8 kb) is shown.

Figure 5A:
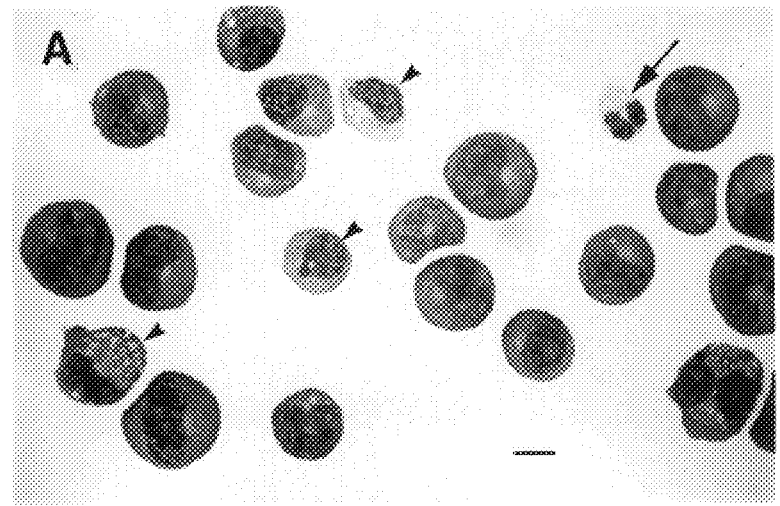
FIGS. 5A–5F present photomicrographs showing the morphology of uninfected and infected FDCP mix A4 cells. Wright-Giemsa Stain. Bars=10 μm. All except FIGS. 5D and 5E were photographed at the same magnification.
Figure 5B:
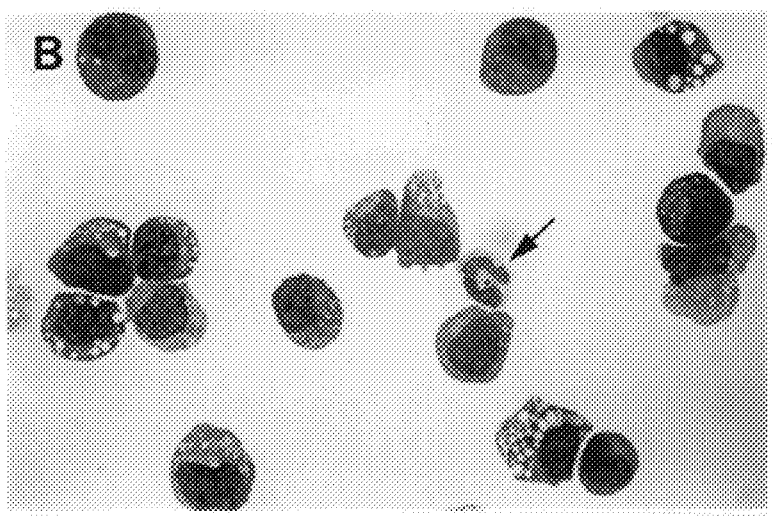
Figure 5C:
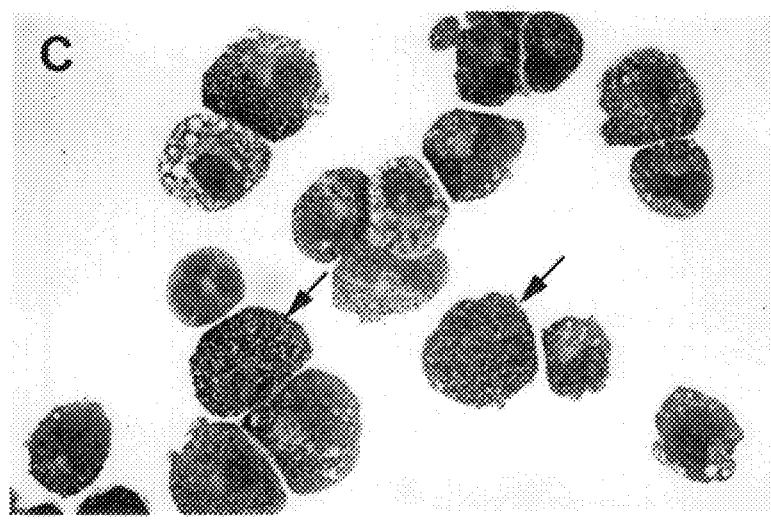
Figure 5D:
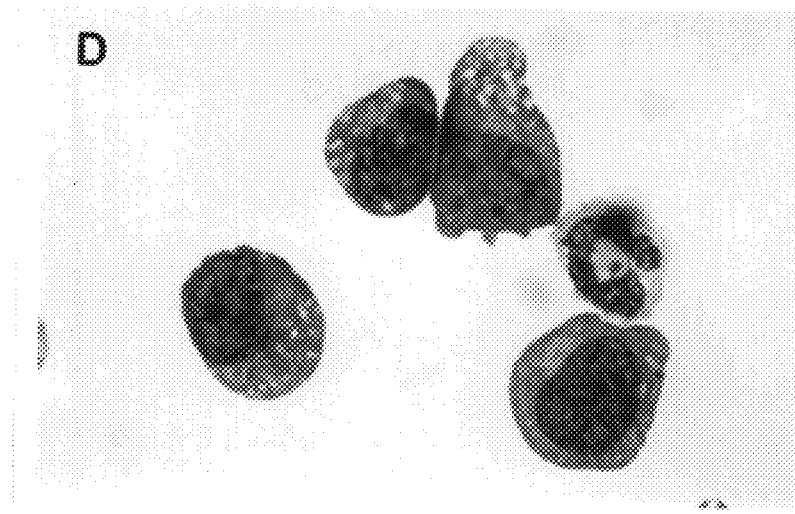

FIGS. 5A–5F show the microscopic morphology of LRARα403SN uninfected (FIGS. 5A and 5F) and infected (FIGS. 5C and 5E) FDCP mix A4 cells. Control cells infected with the LXSN vector are shown in FIGS. 5B and 5D.

EXAMPLE 3

Expression of RARα403 in FDCP mix A4 cells triggers the development of terminally differentiating basophils/mast cells.

Figure 5E:
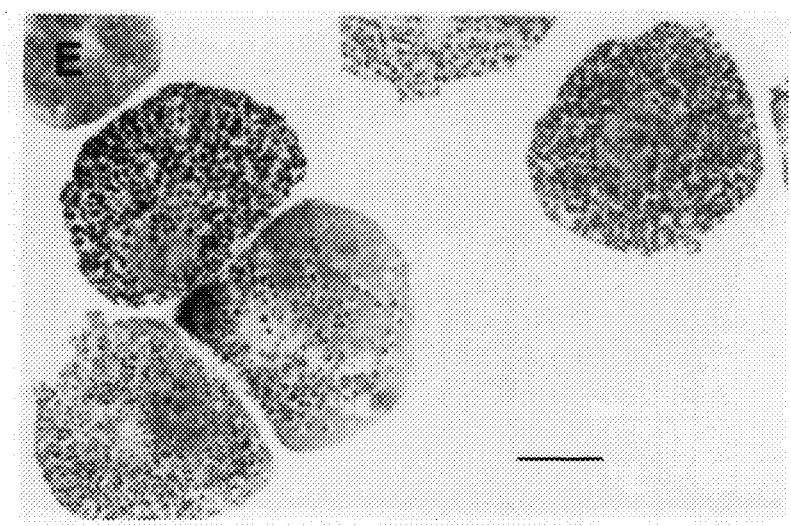
Figure 5F:
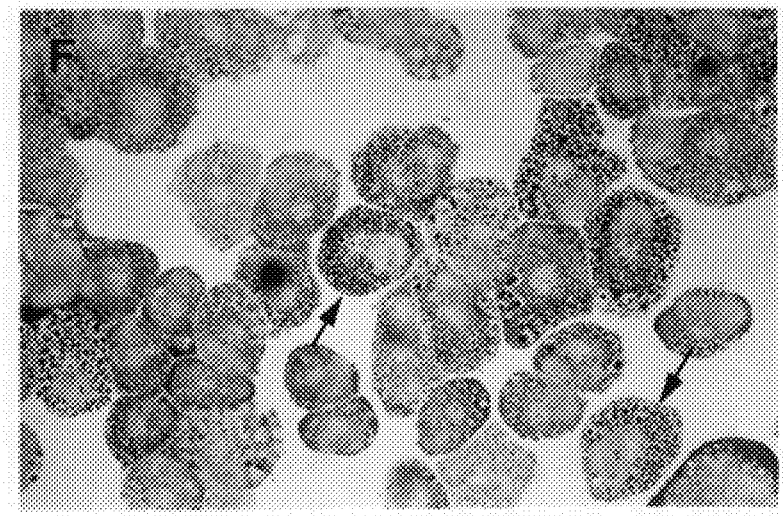

FDCP mix A4 cells were infected with the amphotropic dominant negative LRARα403 3SN retroviral vector as well as the control vectors (LXSN and LRARαSN; the latter harbors the cDNA of normal human RARα), and the infected cells were selected in a medium containing G418 and IL-3. Examination of Wright-Giemsa stained cytospin preparations of FDCP mix A4 cells infected with the control retroviral vectors (LXSN and LRARαSN) revealed the predominant neutrophilic/monocytic differentiation characteristic of the uninfected parental FDCP mix A4 cells (FIGS. 5A, B, and D). In contrast, a very large number of differentiated cells with numerous, intensely basophilic granules appeared in the culture infected with the LRARα403SN retroviral vector within 10 days after the infection (FIG. 5C and 5E). These latter cells expressed high levels of the 4.7 kb retroviral mRNA harboring the dominant negative RARα403 insert (FIG. 4A, lane 3). The granules of these cells stained metachromatically with toluidine blue (FIG. 5F) and are negative for non-specific esterase (a monocyte marker) and alkaline phosphatase (a neutrophil marker). These morphological and cytochemical characteristics suggests that these basophilic granular cells are basophils/mast cells.

To further confirm the basophil/mast cell lineage of the basophilic granular cells in the LRARα403SN-infected FDCP mix A4 cells, we utilized flow cytometry to examine the expression of cell surface immunoglobulin E receptor (IgE R), another basophil/mast cell-specific marker (41, 51). A high percentage (38.4%) of cells expressing surface IgE R was noted in the LRARα403SN-infected cells, while only 0.4% of LXSN-infected cells were positive for IgE R (Table 1). The phenotypes of LRARα403SN and the control (LXSN and LRARαSN)-infected cultures were determined using monoclonal antibodies specific for mouse neutrophils (antibody 7/4; 28) and macrophages (MAC-1 antibody). Consistent with the morphological observations, the LXSN- or LRARαSN-infected FDCP mix A4 cells contained 10–30% 7/4-positive cells, while the LRARα403SN-infected cultures exhibited significantly lower percentages (0–3.5%) of neutrophil antigen-positive cells (Table 1).

TABLE 1

Cell surface antigen expression and histamine production by LXSN- and LRAR-α403SN-infected FDCP mix A4 cells.

| | Expression[a] | | | Histamine[b] | |
|---|---|---|---|---|---|
| Cell line | 7/4 (+) (%) | MAC-1 (+) (%) | IgE R (+) (%) | intra-cellular (pg/cell) | in superna-tant (M) |
| Experiment 1: | | | | | |
| LXSN infected | 28.6 | 8.3 | ND | ND | ND |
| LRARα403SN infected | 1.4 | 1.0 | ND | ND | ND |
| Experiment 2: | | | | | |
| uninfected | 11.1 | 2.0 | ND | 0.14 | 1.6 × 10$^{-6}$ |
| LXSN infected | 14.5 | 2.8 | 0.4 | 0.25 | 2.3 × 10$^{-6}$ |
| LRARαSN infected | 11.4 | 1.0 | ND[c] | ND | ND |
| LRARα403SN infected | 3.6 | 1.0 | 38.4 | 2.17 | 3.0 × 10$^{-4}$ |

[a]Cell-surface antigen expression was analyzed using monoclonal antibodies specific for mouse neutrophils (7/4), monocytes/macrophages (MAC-1), or IgE receptor.
[b]Histamine content was determined by radioimmunoassay. For quantification of intracellular histamine, cells were lysed in distilled water. Negative controls included NIH-3T3 fibroblast, which showed no measurable intracellular histamine, and complete culture medium, which contained <10$^{-9}$ M histamine.
[c]Examination of Wright-stained cytospin preparations revealed very few basophils/mast cells. The LRARαSN-infected culture was indistinguishable from uninfected or LXSN-infected FDCP mix A4 cells by morphology.

Histamine is a lineage-specific marker for basophils/mast cells (12, 44).

Therefore, we measured both the histamine content within these infected cells and the concentration of histamine in the culture supernate (Table 1). We observed that the histamine content of the LRARα403SN-infected cells (2.17 pg/cell, assuming every cell contained equal amounts of histamine to allow comparison) was approximately 10-fold greater than the histamine content of the control LXSN-infected cells (0.25 pg/cell), and was similar to the histamine content of normal basophils/mast cells. Moreover, the histamine concentration in the supernate of the LRARα403SN-infected cultures (3×10$^{-4}$M) was approximately 130-fold increased over the histamine concentration in the control infected cells (2.3×10$^{-6}$M) (Table 1).

Figure 6:
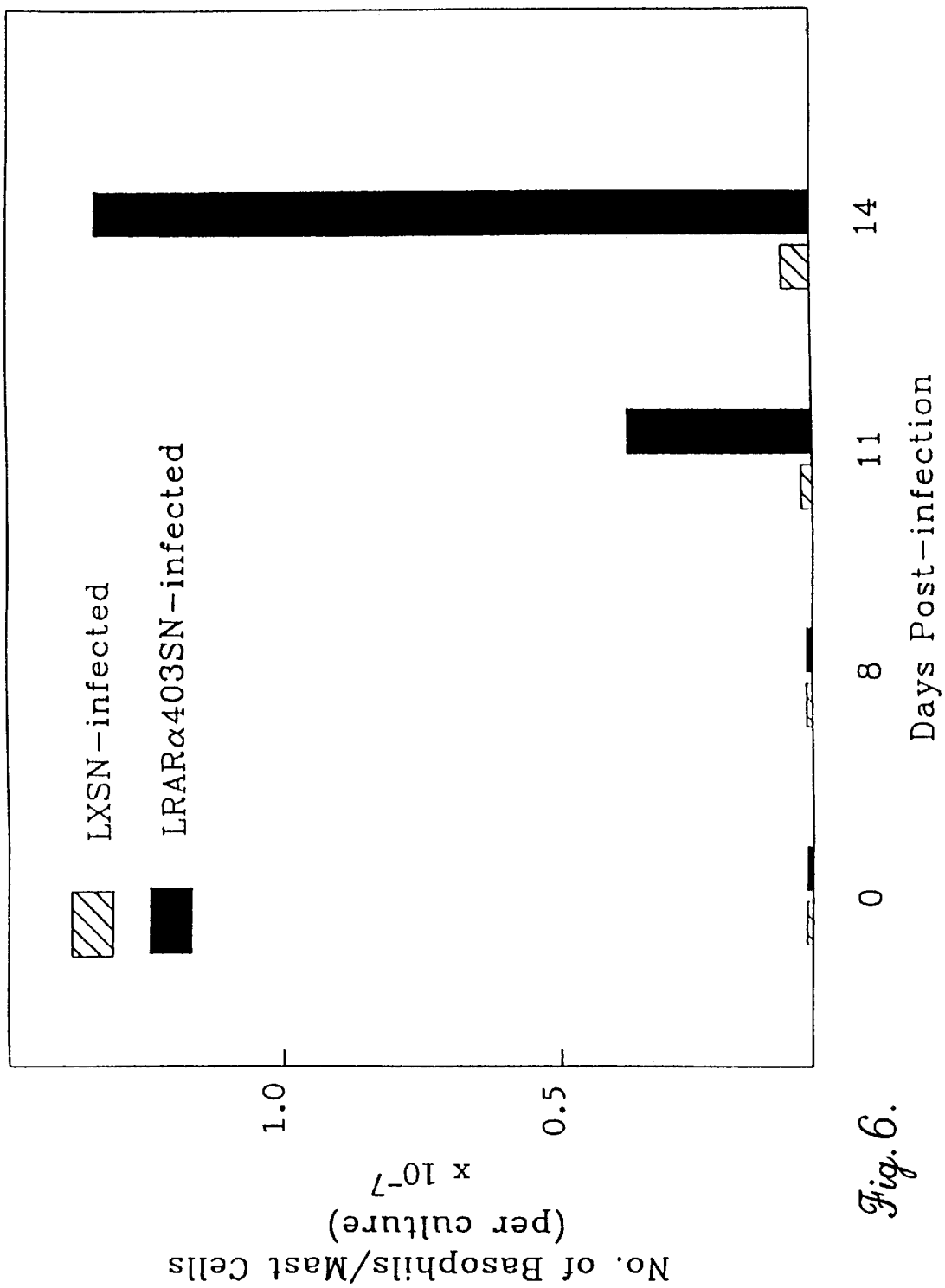
FIG. 6 shows in a graphical manner the net production of basophils/mast cells in infected FDCP mix A4 cell cultures. FDCP mix A4 cells ($1.4 \times 10^6$ cells) were infected with LXSN (hatched bars) or LRARα403 3SN (solid bars) vectors using the supernatant infection method and selected with G418 from days 2 through 8. Similar percentages (10%–15%) of cells infected with either retroviral vector were G418-resistant. These G418-resistant cells were subsequently maintained in culture medium supplemented with WEHI-3B conditioned medium (as a source of IL-3) and subcultured every three days. Production of basophils/mast cells was calculated from the total number of cells and the differential counts on Wright-stained cytospin preparations on each feeding. The total numbers of cells (corrected for subculturing ratios) for LXSN-infected cultures were: $1.3 \times 10^6$ (day 8), $10.1 \times 10^6$ (day 11), $93.8 \times 10^6$ (day 14). Corresponding numbers for LRARα403SN-infected cultures were: $1.3 \times 10^6$ (day 8), $5.5 \times 10^6$ (day 11), $16.8 \times 10^6$ (day 14). All numbers represent mean of duplicates.

The production of basophils/mast cells from FDCP mix A4 cells was quantified following retroviral infection and G418 selection. As shown in FIG. 6, the production of basophils/mast cells in LRARα403 3SN-infected cultures was 20- to 70-fold higher than in LXSN-infected cultures in the first two weeks after the infection.

These observations indicate that retrovirus-mediated gene transfer and expression of the dominant negative RARα403 construct in FDCP mix A4 cells resulted in a switch from spontaneous neutrophil/monocyte differentiation to the development of basophils/mast cells. This same phenotype of markedly increased basophil/mast cell and decreased neutrophil/monocyte development has also been observed in the LRARα403SN-infected FDCP mix A4 cells after they have been cultured continuously in passage for more than 9 months.

EXAMPLE 4

FDCP mix A4 cells infected with LRARα403SN exhibit diminished self-renewal.

Figure 7:
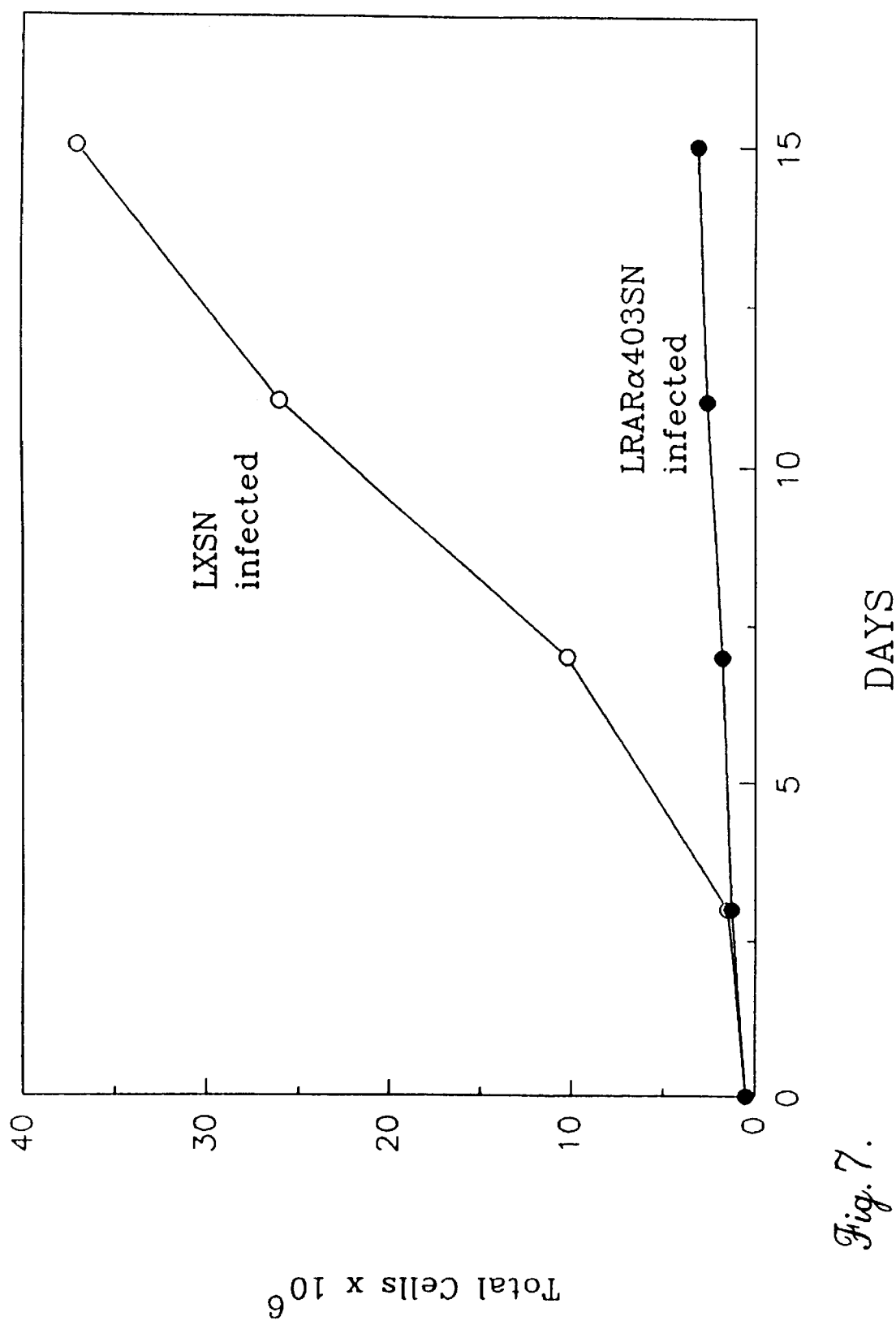
FIG. 7 shows growth curves of FDCP mix A4 cells infected with LRARα403SN (solid circles) or LXSN (open circles). Cultures were initiated with $2 \times 10^5$ low-passage (passage 7) cells of bulk cultures of FDCP mix A4 cells infected with the indicated retroviral vectors and subcultured every 3–4 days. Each data point represents the mean of duplicates.

The LRARα403SN-infected FDCP mix A4 cells exhibited a marked decrease in growth rate (population doubling time of approximately 120 hours) compared with the control LXSN-infected cultures (population doubling time of approximately 30 hours) (FIG. 7). The prolongation of population doubling time of LRARα403SN-infected FDCP mix A4 cells occurred around passages 2–5 and coincided with the appearance of a large number of basophils/mast cells and a decreased number of undifferentiated blasts. These observations suggest that the decreased growth rate of LRARα403SN-infected FDCP mix A4 cells might be in part due to diminished self-renewal of undifferentiated blasts. Therefore, we measured the frequency of cells capable of forming macroscopic colonies in agar cultures in the presence of IL-3. (The macroscopic colonies are defined as colonies with a diameter greater than 0.5 mm after a 14-day incubation and are formed by cells with a greater self-renewal capacity.) The frequency of macroscopic colony-forming cells of FDCP mix A4 cells infected with LRARα403SN was 0.028%, which was 18-fold lower than that of LXSN-infected cells (0.5%). Furthermore, even the macroscopic colony-forming cells in the LRARα403SN-infected cultures demonstrated a relatively lower self-renewal capacity compared with those in the LXSN-infected cultures, since 80% of the individual macroscopic colonies of the latter, when transferred to liquid suspension cultures, were capable of long-term continuous proliferation in IL-3-containing media while only 20% of the macroscopic colonies of LRARα403SN-infected FDCP mix A4 cells demonstrated this proliferative capacity.

Examination of cytospin preparations of individual macroscopic colonies showed that all such colonies of LRARα403SN-infected FDCP mix A4 cells contained high percentages (mean 47.9%) of basophils/mast cells and lower percentages of neutrophils, monocytoid cells, and undifferentiated blasts when compared with LXSN-infected cells (Table 2). Thus the phenotypic change we observed in the bulk culture of LRARα403SN-infected FDCP mix A4 cells was recapitulated by all clonogenic cells.

TABLE 2

Differential counts of macroscopic colonies in agar culture of LXSN- and LRARα403SN infected FDCP mix A4 cells.[a]

| Colony number | Basophil/mast cell (%) | Neutrophil (%) | Monocytoid (%) | Undifferentiated (%) |
|---|---|---|---|---|
| LXSN— infected cells | | | | |
| 1 | 1 | 13 | 52 | 34 |
| 2 | 2 | 2 | 18 | 78 |
| 3 | 1 | 7 | 23 | 69 |
| 4 | 0 | 13 | 24 | 63 |
| 5 | 1 | 5 | 31 | 63 |
| 6 | 0 | 6 | 5 | 89 |
| 7 | 3 | 16 | 31 | 50 |
| 8 | 3 | 7 | 43 | 47 |
| 9 | 0 | 2 | 2 | 96 |
| 10 | 0 | 7 | 23 | 70 |
| Mean | 1.1 | 7.8 | 25.2 | 65.9 |
| LRARα403SN-infected cells | | | | |
| 1 | 59 | 0 | 8 | 33 |
| 2 | 51 | 0 | 8 | 41 |
| 3 | 26 | 0 | 7 | 67 |
| 4 | 52 | 3 | 17 | 28 |
| 5 | 50 | 3 | 15 | 32 |
| 6 | 59 | 2 | 17 | 22 |
| 7 | 25 | 3 | 30 | 42 |
| 8 | 66 | 0 | 11 | 23 |
| 9 | 60 | 2 | 14 | 24 |
| 10 | 31 | 0 | 37 | 32 |
| Mean | 47.9 | 1.3 | 16.4 | 34.4 |

[a]Colony assays were performed as described. Individual macroscopic colonies (>0.5 mm diam.) were identified with a dissecting microscope, and cytospin preparations were made of individual colonies and stained with Wright-Giemsa stain. Differeinial counts were performed on 100 cells each.

EXAMPLE 5

All clonal lines of LRARα403SN-infected FDCP mix A4 cells exhibit predominant basophil/mast cell differentiation.

The above-described experiments were performed on "bulk" cultures of G418-resistant retroviral vector infected FDCP mix A4 cells. We also utilized soft agar cloning and limiting dilution to establish five continuously passaged clonal lines of the LRARα403SN-infected cells. All these clones (c.1–c.5) expressed the appropriate 4.7 kb retroviral mRNA (FIG. 4A). It was noted that the phenotype of these subclones was virtually identical to the "bulk" infected cells. That is, all five subclones exhibited slower IL-3 dependent growth, and Wright-Giemsa stained cytospin preparations revealed high percentages of basophils/mast cells and lower percentages of neutrophils and undifferentiated blasts in these subclones when compared with clones of LXSN-infected FDCP mix A4 cells. This phenotype is further substantiated by flow cytometry using monoclonal antibodies 7/4, MAC-1, and IgE (Table 3).

TABLE 3

Cell-surface antigen expression by clonal lines of
FDCP mix A4 cells infected with
LXSN and LRARα403SN retroviral vectors.[a]

| Clone | IgE R (+) (%) | 7/4 (+) (%) | MAC-1 (+) (%) |
|---|---|---|---|
| LXSN-infected cells | | | |
| c. 1 | 0.0 | 17.4 | 7.4 |
| c. 2 | 6.2 | 23.1 | 9.1 |
| c. 3 | 3.9 | 21.2 | 29.0 |
| c. 4 | 4.0 | 24.2 | 7.9 |
| c. 5 | 3.6 | 17.8 | 8.5 |
| Mean | 3.5 | 20.7 | 12.4 |
| LRARα403SN-infected cells | | | |
| c. 1 | 47.4 | 1.9 | 0.9 |
| c. 2 | 54.4 | 1.3 | 0.9 |
| c. 3 | 66.4 | 0 | 0 |
| c. 4 | 56.3 | 0 | 0 |
| c. 5 | 74.9 | 0 | 0 |
| Mean | 59.9 | 0.6 | 0.4 |

[a]Clonal lines were established by limiting dilution subcloning in 96-well plates or in soft agar. Flow cytometry was performed as described.

EXAMPLE 6

Enhanced GATA-1 expression in LRARα403SN-infected FDCP mix A4 cells.

GATA-1 is a Zn finger-containing transcription factor which is preferentially expressed in hematopoietic cells of the erythroid, megakaryocyte, and mast cell lineages, but not in neutrophilic or monocytic lineages (38, 53). Although GATA-1 was initially identified as a transcriptional regulator of globin gene expression, recent studies show that GATA-1 also binds to the promoter region of the gene of mast cell-specific carboxypeptidase A and activates its expression (61). Northern blot hybridization was used to compare GATA-1 mRNA levels in the LRARα403SN-infected FDCP mix A4 cells vs. the control (LXSN)-infected cells. Relatively low levels of GATA-1 mRNA were detected in the LXSN-infected FDCP mix A4 cells. In contrast, a marked increase in steady state GATA-1 mRNA was noted in the LRARα403SN-infected bulk cultures as well as the five individual infected subclones (FIG. 4B). This enhanced GATA-1 mRNA expression noted in the LRARα403SN-infected FDCP mix A4 cells further corroborates the other basophil/mast cell characteristics displayed by many of these cells.

DISCUSSION OF EXAMPLES 1–6

In the preceding study we have observed that introducing a mutant RARα exhibiting dominant negative activity into the IL-3 dependent, multipotent FDCP mix A4 murine hematopoietic cell line results in a dramatic change in the lineage development of these cells. Although the FDCP mix A4 cell line is by no means the equivalent of normal hematopoietic stem cells, it preserves many properties of multipotent hematopoietic progenitors and thus serves as a useful model for analyzing molecular events involved in myeloid differentiation. This cell line ordinarily commits spontaneously to neutrophilic and monocytic differentiation at moderate frequencies, but upon introduction of the dominant negative RARα403 construct there is a rapid switch to the development of terminally differentiated cells with basophilic cytoplasmic granules (FIGS. 5C and 5E). These differentiated cells exhibit many characteristics of basophils/ mast cells including metachromatic staining with toluidine blue (FIG. 5F), histamine production (Table 1), expression of cell surface IgE receptor (Table 1), and enhanced GATA-1 mRNA levels (FIG. 4B).

The development of basophils/mast cells in the LRARα403SN-infected cultures is attributable to the expression of the dominant negative RARα403 construct. None of the cultures infected with the control vectors (LXSN and LRARαSN) preferentially differentiated into basophils/mast cells. In contrast, all of the LRARα403SN-infected subclones that we have analyzed exhibit predominantly basophil/mast cell phenotype (Tables 2 and 3). Moreover, the characteristic basophil/mast cell morphological and histochemical changes occur rapidly (within 10 days) after infection with this dominant negative RARα403 retroviral construct. These observations exclude rare events such as retroviral vector-induced mutation as the cause of the prominent phenotypic changes in the cultures. In addition, we have observed that continuous passaging of control LXSN-infected FDCP mix A4 cells for 6 months does not result in the conversion to basophil/mast cell development, further excluding random mutation as the cause of the observed phenotypic changes.

Our observation that many clones of LRARα403SN-infected FDCP mix A4 cells continue to produce a small number of neutrophils and monocytes in addition to the large number of basophils/mast cells (Tables 2 and 3) indicates that the individual clonogenic cells are at least tripotent, i.e., capable of differentiating into a) basophils/mast cells, b) neutrophils, and c) monocytes. Therefore, the observed phenotypic change does not result from immortalization of any rare committed, unipotent basophil/mast cell progenitors. (In fact, the basophils/mast cells in LRARα403SN-infected cultures have a limited life span of 6–12 days and degenerate thereafter.) Rather, this phenotype is due to a shift by the multipotent FDCP mix A4 cells from the spontaneous production of primarily neutrophils and monocytes to the continuous, preferential production of basophils/mast cells. It should be emphasized that the net production (absolute number) of basophils/mast cells produced by LRARα403SN-infected FDCP mix A4 cells is increased by 20–70 fold within the first 2 weeks of infection (FIG. 6). This finding makes it unlikely that the altered FDCP mix A4 phenotype is due to selective elimination of neutrophils and monocytes in the culture resulting in the progressive accumulation of basophils/mast cells. In this latter scenario, the percentage of basophils/mast cells would increase in the infected cultures, but the absolute number would not.

Figure 8A:
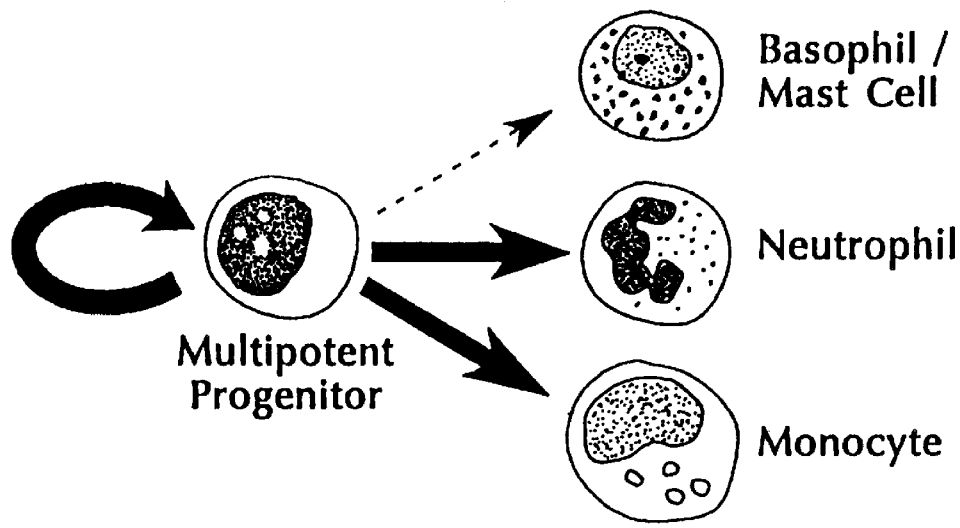
FIGS. 8A and 8B schematically summarize the effects of the dominant negative RARα403 on the lineage development of FDCP mix A4 cells.
Figure 8B:
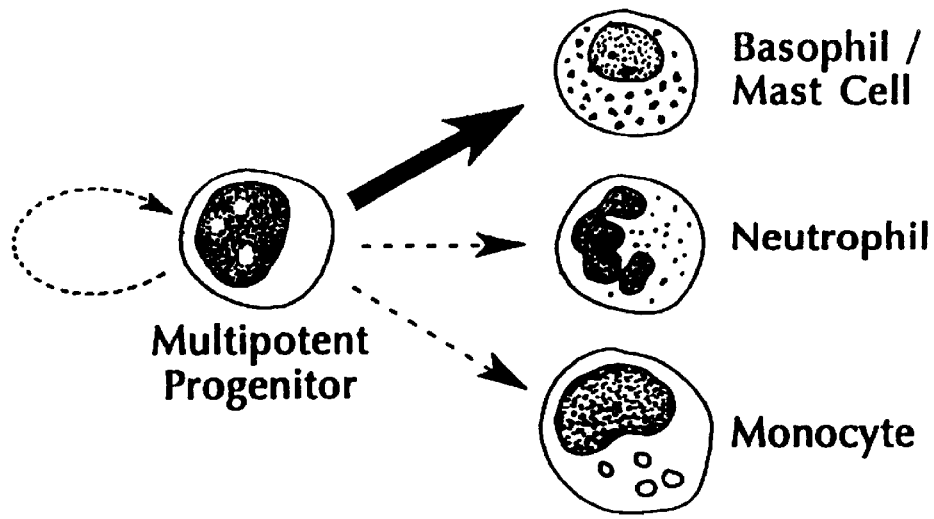

Concomitant with the switch from spontaneous neutrophil/monocyte differentiation to the development of basophils/mast cells, the LRARα403SN-infected cells exhibit lower percentages of morphologically undifferentiated blasts (Table 2), display an 18-fold reduction in the frequency of macroscopic colony-forming cells, and show a markedly reduced growth rate (FIG. 7). These three parameters suggest that the self-renewal of LRARα403 3SN-infected cells has decreased, either due to the prolongation of the cell cycle of undifferentiated blast cells or due to the increased recruitment of these cells into the terminal differentiation pathway, or both. The effects of the dominant negative RARα403 on the development of different myeloid lineages and the self renewal of FDCP mix A4 cells are schematically summarized in FIG. 8.

The observation that introducing a dominant negative RARα construct into the FDCP mix A4 cells results in a dramatic change from spontaneous neutrophil and monocyte differentiation to basophil/mast cell development indicates that the normal RARα plays important roles in regulating the development of myeloid progenitors. It appears that normal RARα promotes the development of neutrophils and monocytes but represses the development of basophils/mast cells. One possible model is that the normal RARα blocks the development of basophils/mast cells by uninfected FDCP mix A4 cells. Removal of this blockade by the dominant negative RARα403 allows the development along the basophil/mast cell lineage under the strong influence of IL-3 used to maintain the culture. (IL-3 is a potent inducer of basophil/mast cell differentiation by normal hematopoietic stem cells.) In this model, the normal RARα does not necessarily play the role of a "master switch" that commits cells to different specific hematopoietic lineages. More likely this transcription factor plays some important role(s) in the complex cascade of molecular events leading to or subsequent to the lineage commitment process. It is important to note that this apparent hematopoietic regulatory activity of RARα occurs in the relatively low concentrations of RA that are endogenous to serum (less than $10^{-8}$M; 9, 13). (There is 20% horse serum in the complete culture media, above.) This suggests that RARα exerts its hematopoietic regulatory activity in FDCP mix A4 cells either in the absence of ligand or in relatively low concentrations of ligand. In contrast, significantly higher concentrations of RA ($10^{-7}$M to $10^{-5}$M) are required to induce the differentiation of promyelocytic leukemia cells (3, 5) or to activate genes at the 5' end of the HOX2 cluster in human embryonal cells (47).

Although it is clear from the co-transfection studies in NIH3T3 fibroblasts (FIG. 2) that the RARα403 construct exhibits dominant negative activity against the normal RARα, the full spectrum of its biological activity is yet to be defined. The prototype dominant negative nuclear receptor is the v-erbA oncogene, which exhibits deletions in the C-terminal ligand binding domain compared with its homologue c-erbA, the thyroid hormone receptor. These C-terminal deletions abolish $T_3$ binding to the v-erbA protein, and as a result v-erbA protein may interfere with normal thyroid hormone function by forming heterodimers with c-erbA that cannot be activated by $T_3$ (10, 14). Our RARα403 construct involves a 59-amino acid truncation in the C-terminal RA binding domain which most likely also interferes with ligand (RA) binding. Thus, RARα403 may interfere with normal RARα function by forming inactive heterodimers with RARα. Alternatively, the mutated RARα may compete for interactions with other transcription factors that may be essential for RARα activity. For example, members of the RXR family of RA receptors can dimerize with RARs, and these heterodimers display greater affinity for specific DNA target sequences than do RAR homodimers (33, 36, 56, 60). The RARα403 gene product potentially may form inactive heterodimers with RXRs, and this sequestration of RXRs may prevent the latter from potentiating the activity of other RA receptors. Of relevance is the finding that a truncated construct containing the first 404 amino acids of RARα (differing from our RARα403 construct by only a single amino acid) can dimerize with RXRs (56). Thus it is possible that the dominant negative RARα403 exerts its biologic effects not only by directly inhibiting the normal RARα but also by indirectly inhibiting a related receptor(s) whose full function depends on dimerization with RXRs.

The data reported above indicates that in the multipotent IL-3 dependent FDCP mix A4 murine hematopoietic cell line, RARα and/or related molecules positively influence the development of neutrophils and monocytes as well as the self renewal pathway but repress the development of basophils/mast cells. The alteration in the lineage development of the multipotent FDCP mix A4 hematopoietic cell line following the transduction of the dominant negative RARα construct indicates that RARα and/or closely related molecules play important roles in the development of neutrophils, monocytes, and basophils/mast cells.

EXPERIMENTAL PROCEDURES

EXAMPLES 1–6

Plasmid Constructions

The sequence of full-length cDNA of human RARα has been published (25) and is reproduced here as FIGS. 16B and 16C. The plasmid pGEM3Z-hRARα D5' harbors human RARα cDNA sequences from the initiator ATG to the BamHI site at position 2103. This plasmid was digested with SmaI which cut at position 1311 and 1597 of RARα cDNA (FIG. 1A). The larger fragment was isolated, ligated with an NheI linker (which inserted a stop codon) and recircularized. The new construct was designated pGEM3Z-RARα403 (FIG. 1B). An EcoRI site was present in the pGEM3Z polylinker immediately 5' to the initiator ATG of the RARα403 insert. The 1.8 kb EcoRI-BamHI fragment of pGEM3Z-RARα403 was then cloned into the EcoRI-BamHI site of the retroviral vector LXSN (FIG. 1C) (42), and the recombinant vector was designated pLRARα403SN (FIG. 1D). The plasmid pLRARαSN was constructed by subcloning a 2.8 kb EcoRI fragment of human RARα cDNA clone (42) into the EcoRI site of pLXSN as previously detailed (8). The expression plasmid pEMSV-RARα was constructed by cloning the 2.8 kb human RARα cDNA into the EcoRI site of the expression vector pEMSVscribe (11). Plasmids pTRE-CAT and pRRE-CAT consist of a single copy of either a synthetic palindromic TRE (5'-TCAGGTCATGACCTGA-3') (54) or the RRE identified in the RARα promoter (5'-GTAGGGTTCACCGAAAGTTCACTC-3') (19) inserted upstream of the tk promoter (−109 to +5) and CAT reporter gene and were obtained from Jeannette Bigler (Fred Hutchinson Cancer Research Center, Seattle, Wash.). Plasmid pCMV-GH was constructed by inserting a 1.1 kb PstI-XbaI fragment containing the cytomegalovirus immediate early gene promoter from pON249 (24) into the human growth hormone reporter construct pOGH (Nichols Institute) and was provided by Ed Agura (Fred Hutchinson Cancer Research Center).

Transient Expression Assays

NIH3T3 tk- cell were maintained in DMEM supplemented with 10% fetal calf serum (FCS) and plated 24 hours before transfection. The medium was replaced with fresh DMEM supplemented with 10% charcoal-resin stripped FCS 4 hours before transfection. Cells were transfected by calcium phosphate precipitate method with 2.5 µg of pEMSV-RARα, varied amounts of pLRARα403SN, 2.5 µg of pTRE-CAT, 1 µg of pCMV-GH as an internal control for transfection efficiency, and pLXSN to equalize the total amount (23.5 µg per 100-mm dish) of DNA and LTRs transfected. For transient expression assays using pRRE-CAT as the reporter, the following conditions were employed: 1 µg of pEMSV-RARα, varied amounts of pLRARα403SN, 4 µg of pRRE-CAT, 1 µg of pCMV-GH, and pLXSN to equalize the total amount (16 µg per 100-mm dish) of DNA and LTRs transfected. Sixteen hours after transfection, the cells were washed with PBS and refed with DMEM supplemented with 10% charcoal-resin stripped FCS and incubated for another 32 hours with or without $10^{-6}$M all-trans retinoic acid (ATRA). Electroporation of FDCP mix A4 cells was performed in 0.4-mm cuvettes using a Bio-Rad gene Pulser (Richmond, Calif.) with the following parameters: $2\times10^7$ cells, 25 µF/800 v, 75 µg ea. of pCMV-GH, pRRE$_4$-CAT (containing four copies of RRE instead of one), pEMSV-RARα and pLRARα403 3SN. Culture supernates were collected for determination of growth hormone concentration using a radioimmunoassay kit (Nichols Institute). Preparation of cell lysates and CAT assay were performed according to published methods (Sambrook et al., which is hereby incorporated by reference 45). The volume of cell lysate used in CAT assay was normalized for transfection efficiency as determined by the growth hormone reporter (pCMV-GH) internal control. Following thin layer chromatography on silica gel, the non-acetylated and acetylated $^{14}$C-labeled chloramphenicol was quantitated by a Phosphor Imager and ImageQuant software (Molecular Dynamics).

Retroviral Producer Cell Lines and Retroviral Infection

Amphotropic viral producer cell lines were established according to published procedures (42). Briefly, pLRARα403SN plasmid was transfected into the ecotropic viral packaging cell line PE501 and the transiently expressed viral particles were rescued to infect the amphotropic viral packaging cell line PA317 (43). Infected PA317 cells were selected in G418-containing medium, followed by subcloning. One clone, PA317/LRARα403SN c.10, expressing high levels of retroviral mRNA of the predicted size by Northern blot analysis and producing supernates with a titer of 4–6× $10^6$ colony forming units per ml as assayed on NIH3T3 tk- cells, was chosen as the producer of retroviral vector particles for this study. A cell line PA317/LRARαSN producing a retroviral vector (LRARαSN) harboring the cDNA of the normal human RARα was similarly established as previously described (8).

HL-60 and FDCP mix A4 cells were infected with retroviral vectors by either a 24-hr co-cultivation with irradiated (1200 rads) viral producers or infection with viral supernates in the presence of 4 µg/ml polybrene. Infected cells were then selected in complete culture medium containing 1 mg/ml (for HL-60) or 300 µg/ml (for FDCP mix A4) of G418 for 8–10 days. Clonal lines were generated by limiting dilution in 96-well plates or cloning in 0.3% agar.

Cell Cultures

HL-60 cells were maintained in RPMI 1640 supplemented with 5% FCS. FDCP mix A4 cells were maintained in Iscove's modified Dulbecco's medium (IMDM) supplemented with 20% (v/v) horse serum and 10% (v/v) WEHI 3B cell line conditioned medium (as a source of IL-3) and subcultured every 3 days. Colony assays of A4/LXSN and A4/LRARα403 3SN were done in IMDM supplemented with 25% horse serum, 10% WEHI 3B conditioned medium, and 0.3% agar. These agar cultures were incubated at 37° C. in 5% $O_2$, $CO_2$ and 90% $N_2$ for 14 days.

Northern Blots

Total RNAs were extracted with guanidine hydrochloride and subjected to Northern blotting in formaldehyde gels as previously described (7). Molecular probes used in Northern hybridization included the following: hRARα, the 1.3 kb EcoRI-SmaI fragment of the phK1 RARα cDNA clone (25); and the mouse GATA-1 cDNA probe (53) which was obtained from David Martin (Fred Hutchinson Cancer Research Center). All probes were labeled with $^{32}$P by nick translation prior to hybridization.

Cell Phenotyping

Cytospin preparations of cell suspensions were stained with 1% toluidine blue for 15 minutes and washed with tap water. For quantitation of intracellular histamine, $2\times10^5$ cells were washed with PBS and resuspended in 1 ml of distilled water and lysed by three cycles of freezing and thawing. Radioimmunoassay of histamine in cell lysates or culture supernates was performed according to manufacturer's instructions (Immunotech International).

For flow cytometry, cells were exposed to saturating concentrations of primary rat IgG2a monoclonal antibodies 7/4 (generously provided by S. Gordon, Oxford, UK) or MAC-1 (PharMigen) at 4° C. for 10 min., washed with PBS/1%FCS, then stained with an FITC-labeled goat anti-rat IgG (H+L) for 10 min. at 4° C. After final washing with PBS/1%FCS, fluorescence was measured with a Becton-Dickinson FACScan flow cytometer and analyzed by the Reproman software (Kirkegaard & Perry Labs, Md.). An irrelevant rat IgG2a monoclonal antibody (PharMigen) was used as the isotype control. For IgE R staining, cells were incubated with culture medium containing 15 µg/ml mouse IgE (PharMigen) at 37° C. overnight, washed three times with PBS/1%FCS, stained with FITC-goat anti-mouse IgE (Nordic Immunologicals) at 4° C. for 10 min., followed by washing with PBS/1%FCS.

EXAMPLE 7

Response of FDCP mix A4 cells to GM-CSF.

When maintained in a medium supplemented with 20% horse serum (HS) and IL-3, FDCP mix A4 cells differentiate spontaneously into neutrophils and macrophages at low-moderate frequencies (10–20%). Removal of IL-3 and stimulation with GM-CSF in HS-supplemented medium induces these cells to differentiate into mature neutrophils and macrophages in 4 to 10 days (Table 4) (27, 49).

TABLE 4

Serial differential counts of FDCP mix A4 cells infected with LXSN vs. LRAR-α403SN viruses and induced by GM-CSF plus trace IL-3[a].

| | LXSN-infected | | | | | LRAR-α403SN-infected | | | | |
|---|---|---|---|---|---|---|---|---|---|---|
| | Blast | Prom. + Myelo. + Meta. | Band + Seg. | Macro. | Mast | Blast | Prom. + Myelo. + Meta. | Band + Seg. | Macro. | Mast |
| Day 0 | 75 | 13 | 7 | 4 | 1 | 48 | 5 | 4 | 6 | 37 |
| Day 6 | 2 | 14.5 | 49 | 34.5 | 0 | 3 | 35.5 | 45 | 8.5 | 8 |
| Day 12 | 0 | 0.5 | 25 | 74.5 | 0 | 0 | 51.5 | 32 | 8 | 8.5 |
| Day 18 | 0 | 0 | 1 | 99 | 0 | 0 | 66.5 | 16.5 | 4.5 | 12.5 |
| Day 24 | 0 | 0 | 0 | 0 | 0 | 0 | 69.5 | 20 | 2 | 8.5 |

TABLE 4-continued

Serial differential counts of FDCP mix A4 cells infected with LXSN vs. LRAR-α403SN viruses and induced by GM-CSF plus trace IL-3[a].

| | LXSN-infected | | | | | LRAR-α403SN-infected | | | |
|---|---|---|---|---|---|---|---|---|---|
| | Blast | Prom. + Myelo. + Meta. | Band + Seg. | Macro. | Mast | Blast | Prom. + Myelo. + Meta. | Band + Seg. | Macro. | Mast |
| Day 30 | 0 | 0 | 0 | 0 | 0 | 0 | 78.5 | 15 | 3.5 | 3 |
| Day 150 | 0 | 0 | 0 | 0 | 0 | 0 | 96 | 4 | 0 | 0 |

[a]Experimental details are as described. The day 150 differential counts of LRAR-α403SN-infected culture are those of the GMB cell line; numbers represent mean percentages of duplicates; and Prom.: promyelocytes; Myelo.: myelocytes; Meta.: metamyelocytes; Band: band-form neutrophils; Seg.: segmented neutrophils; Macro.: macrophages; Mast: mast cells.

Figure 11A:
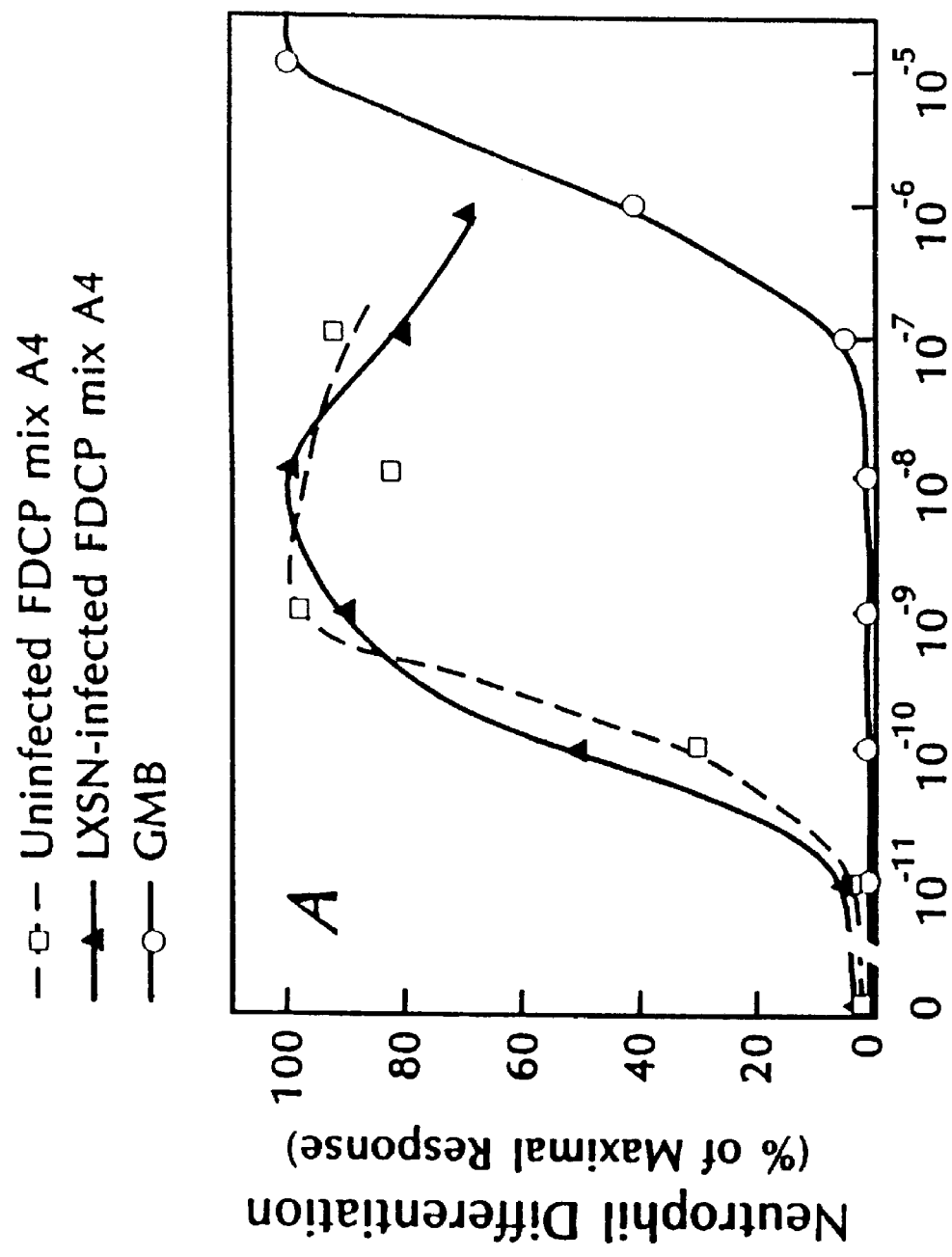
FIG. 11A graphically depicts the dose-response curve for RA-induced neutrophil differentiation in GMB cells (open circles) as compared to LXSN-infected FDCP mix A4 cells (closed triangles) and uninfected FDCP mix A4 cells (open squares). The GMB cells were treated with the indicated concentrations of RA for 72 hours. Differential counts were performed on Wright-stained cytospin preparations. Over 95% of GMB cells differentiated into neutrophils 72–96 hours after exposure to $10^{-5}$M RA. For comparison, the uninfected and LXSN (control)-infected FDCP mix A4 cells were cultured in IMDM supplemented with 10% fetal calf serum (FCS; Hyclone), 5.0 ng/ml of GM-CSF and the indicated concentrations of RA. (In these control experiments it was necessary to use selected batches of FCS in which GM-CSF-induced neutrophil differentiation was relatively low in order to demonstrate the effect of exogenous RA on the differentiation process. Presumably these particular FCS batches harbor relatively low concentrations of endogenous RA. All batches of HS seemed to have optimal concentrations of endogenous RA in our differentiation assays and addition of exogenous RA results in toxicity. The dose-response curve of GMB cells is the same regardless of the types of serum used due to the higher RA concentration required to differentiate.) The results were plotted as the mean of duplicate samples.

Interestingly, we have observed that this GM-CSF-induced neutrophil differentiation appears blunted when certain batches of fetal calf serum (FCS) are used in place of HS, but supplementation of such cultures with low concentrations of RA ($10^{-10}$ to $10^{-9}$M) restores this GM-CSF-induced neutrophil differentiation (see FIG. 11A). Thus this GM-CSF-induced neutrophil differentiation of FDCP mix A4 cells appears to require the low concentrations of RA that are ordinarily present in most sera (13).

EXAMPLE 8

Neutrophilic differentiation is interrupted in FDCP mix A4 cells expressing the dominant negative RARα403.

Figure 9:
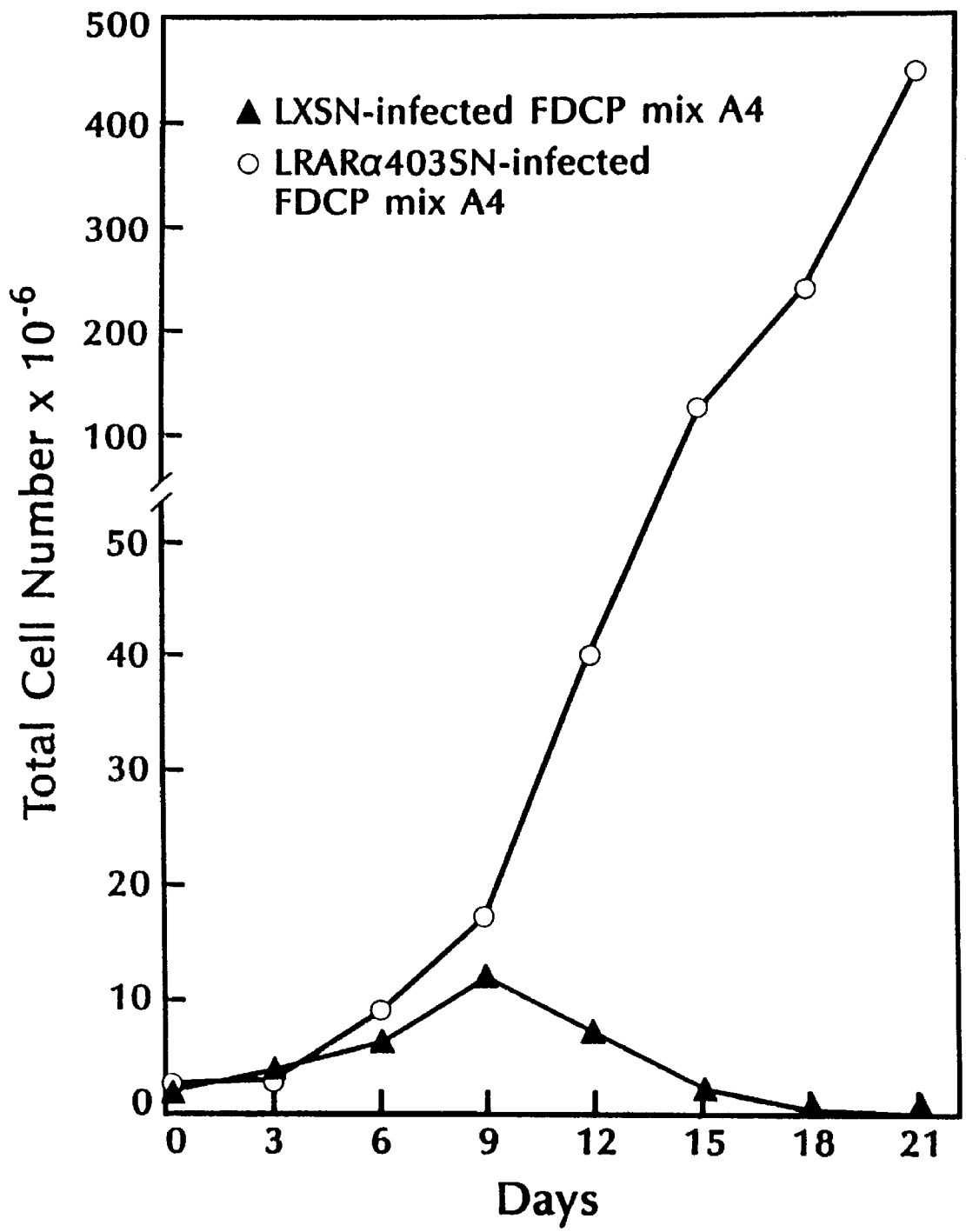
FIG. 9 compares graphically the growth of LXSN-infected (solid triangles) and LRARα403SN-infected (open circles) FDCP mix A4 cells stimulated with GM-CSF. Two million G418-resistant LXSN (control)- or LRARα403SN-infected FDCP mix A4 cells were washed with buffered saline to remove excess IL-3 and reseeded at $2 \times 10^5$ cells/ml in IMDM supplemented with 20% (v/v) HS, 5 ng/ml of GM-CSF (Immunex), and 0.2% (v/v) WEHI 3B conditioned medium. Cells were subcultured every three days. Cell numbers were corrected for subculturing ratios. Note the decline after day 9 and the eventual extinction after day 21 of LXSN (control)-infected cultures, while the LRARα403 3SN-infected cultures continue to expand in GM-CSF. Data points represent the mean of duplicates.

We infected the FDCP mix A4 cells with the LRARα403SN retroviral vector harboring the dominant negative RARα403 construct. In the presence of IL-3, the LRARα403SN-infected FDCP mix A4 cells remain multipotent but differentiate predominantly along the mast cell lineage (52). However, when these cells are transferred to media containing GM-CSF (5 ng/ml) and only trace (0.2% v/v) WEHI 3B conditioned medium, their behavior differs from the LXSN (control vector without insert)-infected cultures in two important ways: (i) only the former produce significant numbers of basophils/mast cells (Table 4), and (ii) while all the cells in LXSN-infected cultures differentiate and die after 2–3 weeks in GM-CSF, the LRARα403SN-infected FDCP mix A4 cultures continue to proliferate over an extended period (FIG. 9). Serial examination of the GM-CSF-induced, LRARα403SN-infected FDCP mix A4 cells reveals the presence of numerous clusters of immature cells first appearing around day 8–14, which are never noted in the GM-CSF-induced control infected cultures. These immature cells quickly become the predominant cell type in the culture and have proliferated continuously as a GM-CSF-dependent cell line for over 1 year to date (referred to as the GMB cell line below).

EXAMPLE 9

The GMB cells are neutrophilic promyelocytes.

Figures 10A, 10B:
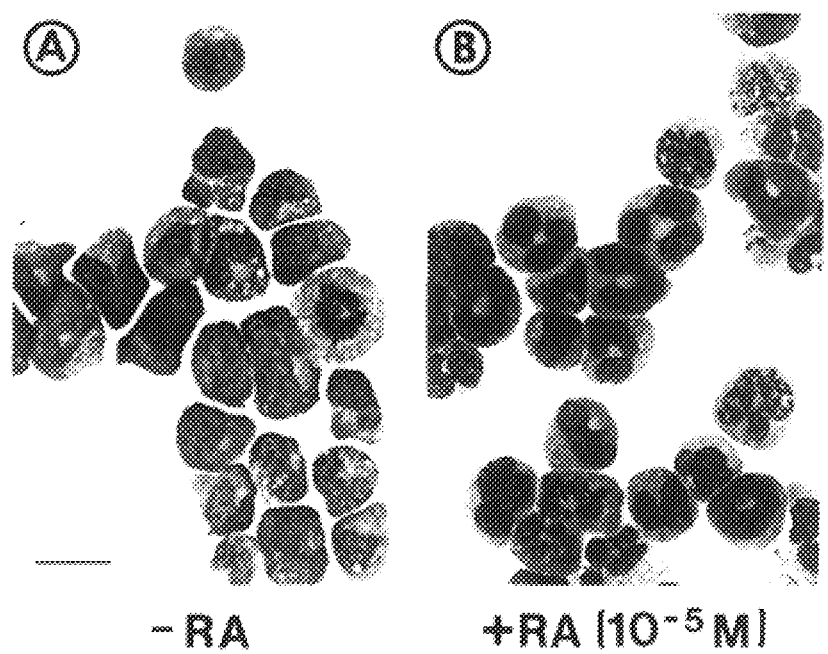
FIG. 10A presents a photomicrograph showing the morphology of uninduced GMB cells. A low percentages of mature neutrophils are normally present in GMB cultures.
FIG. 10B presents a photomicrograph of GMB cells maintained in growth medium containing GM-CSF (5 ng/ml) and treated with RA ($10^{-5}$M) for 80 hours. Bar=20 μm.

Morphologically, the GMB cells resemble promyelocytes or early myelocytes (FIG. 10A). Consistent with their morphology, these cells are strongly positive for the murine neutrophIL-specific "7/4" antigen (28) and positive for chloroacetate esterase (specific for neutrophils) (not shown). On Northern blots (not shown), these cells express high levels (at least 10-fold over endogenous RAR (X) of the 4.7 kilobase (kb) retroviral RNA containing the RARα403 message but do not express mRNA for c-fms (specific for monocytic lineage) or GATA-1 (hematopoietic expression restricted to erythroid, megakaryocytic, and mast cell lineages) (53). Furthermore, the GMB cells are negative for mast cell/basophil markers including surface IgE receptors and toluidine blue metachromatic staining. Taken together, these findings suggest that the GMB cells represent neutrophilic promyelocytes that fail to complete terminal differentiation. We have repeatedly established GMB-like cells from both low- and high-passage LRARα403SN-infected FDCP mix A4 cells under the conditions described above. In contrast, no such cell line can be isolated from the uninfected or control vector (LXSN or LRARαSN, the latter harboring the cDNA of normal human RARα)-infected FDCP mix A4 cell under the same conditions, thus demonstrating the requisite role of the dominant negative RARα403 in the genesis of GMB cells. cl EXAMPLE 10

Expression of the dominant negative RARα403 in GMB cells reduces their RA responsiveness.

Figure 11B:
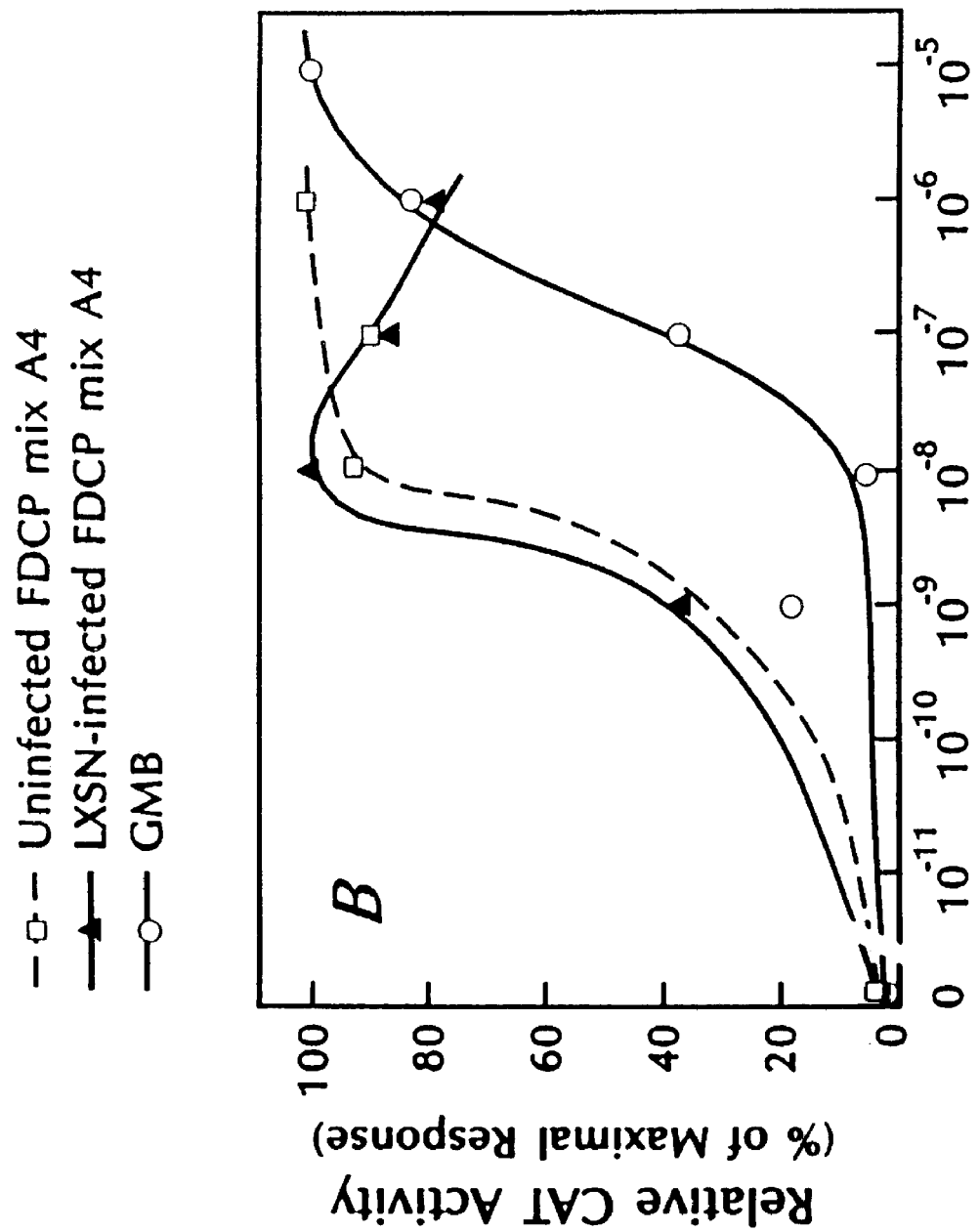
FIG. 11B graphically depicts the dose-response curve for RA-induced transactivation of pRRE$_4$-CAT. The volumes of cell lysate used in CAT assay were normalized for transfection efficiency as determined by growth hormone expression.

Perhaps the most compelling evidence that the GMB cells represent neutrophilic promyelocytes with blocked terminal differentiation is the finding that nearly all the GMB cells differentiate rapidly (72–96 hours) and synchronously into mature neutrophils without undue cytotoxicity when treated with supra-physiologic concentrations ($10^{-6}$M to $10^{-5}$M) of RA in the presence of GM-CSF (FIG. 10B). The half-optimal concentration of RA that induces this terminal neutrophil differentiation of GMB cells is about $10^{-6}$M and the optimal concentration is $10^{-5}$M (FIG. 11A). Interestingly, this dose-response curve of RA-induced differentiation of GMB cells is comparable to the dose-response curve of RA-induced transactivation of a CAT reporter construct harboring the RARα retinoic acid response elements (pRRE$_4$-CAT) (52) in transient expression assays in GMB cells (FIG. 11B). In contrast, the dose-response curves of the effect of RA on GM-CSF-induced neutrophil differentiation and of the transactivation of pRRE$_4$-CAT in uninfected or LXSN (control)-infected FDCP mix A4 cells reveal a half-optimal RA concentration of $10^{-10}$M to $10^{-9}$M and an optimal concentration of about $10^{-8}$M (FIGS. 11A and 11B), concentrations reported to be present in most sera (13). This shifting of the RA dose-response curve by 2–3 logs in GMB cells confirms that the RARα403 exerts dominant negative effects against the endogenous RARs in GMB cells.

FIG. 11A depicts graphically the dose-response curve for RA-induced neutrophil differentiation in GMB cells.

EXAMPLE 11

The dominant negative RARα403 blocks the differentiation of primary mouse neutrophil precursors at the promyelocyte stage.

Figure 12:
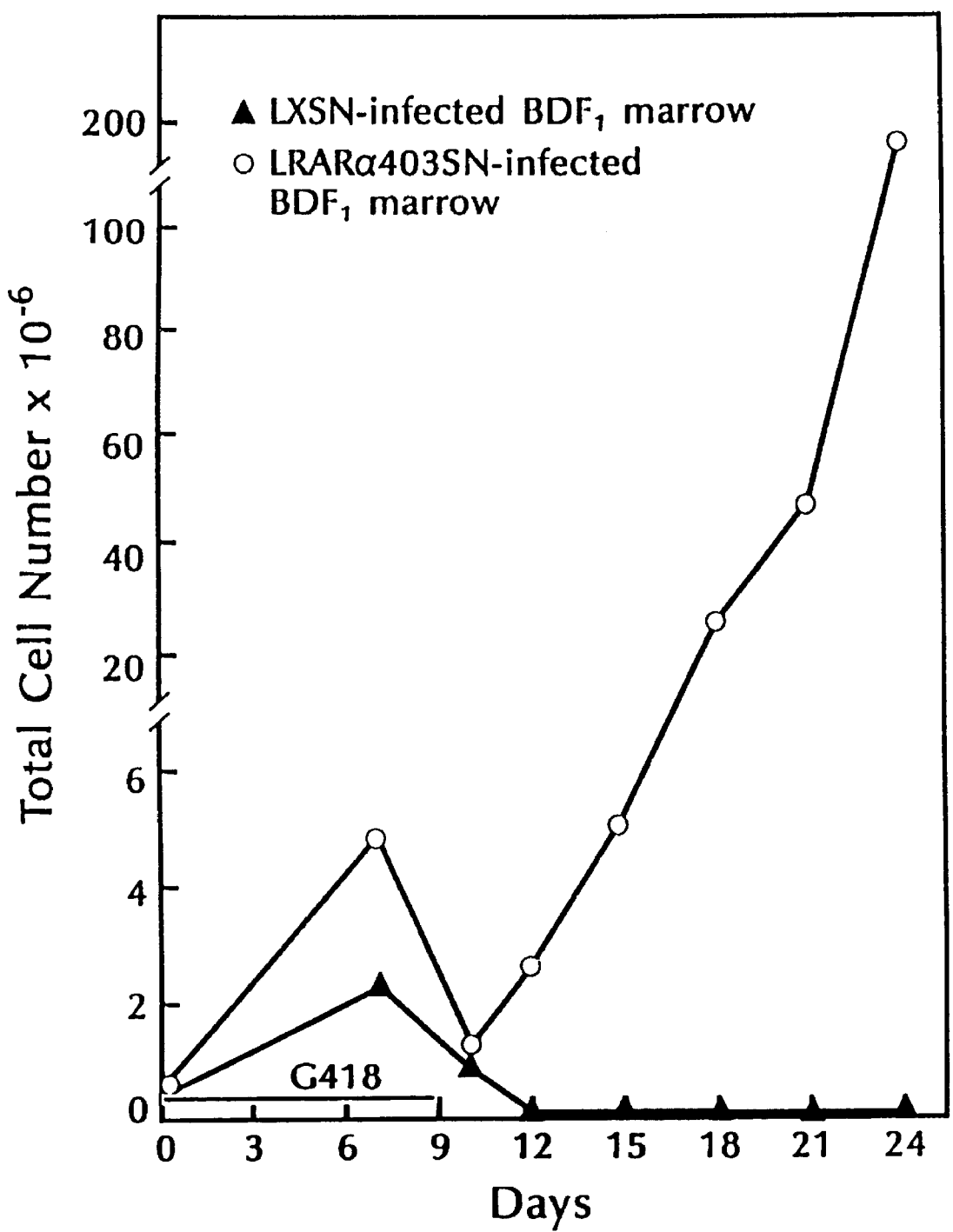
FIG. 12 graphically depicts the growth pattern of LXSN- (closed triangle; control) and LRARα403SN-infected (open circle) BDF$_1$ bone marrow cells. Half a million infected cells were cultured in IMDM supplemented with 20% (v/v) HS and 5 ng/ml GM-CSF. G418 (400 μg/ml) was present from day 0 through day 9 as indicated by the solid bar. Mean of duplicates.
Figures 13A, 13B:
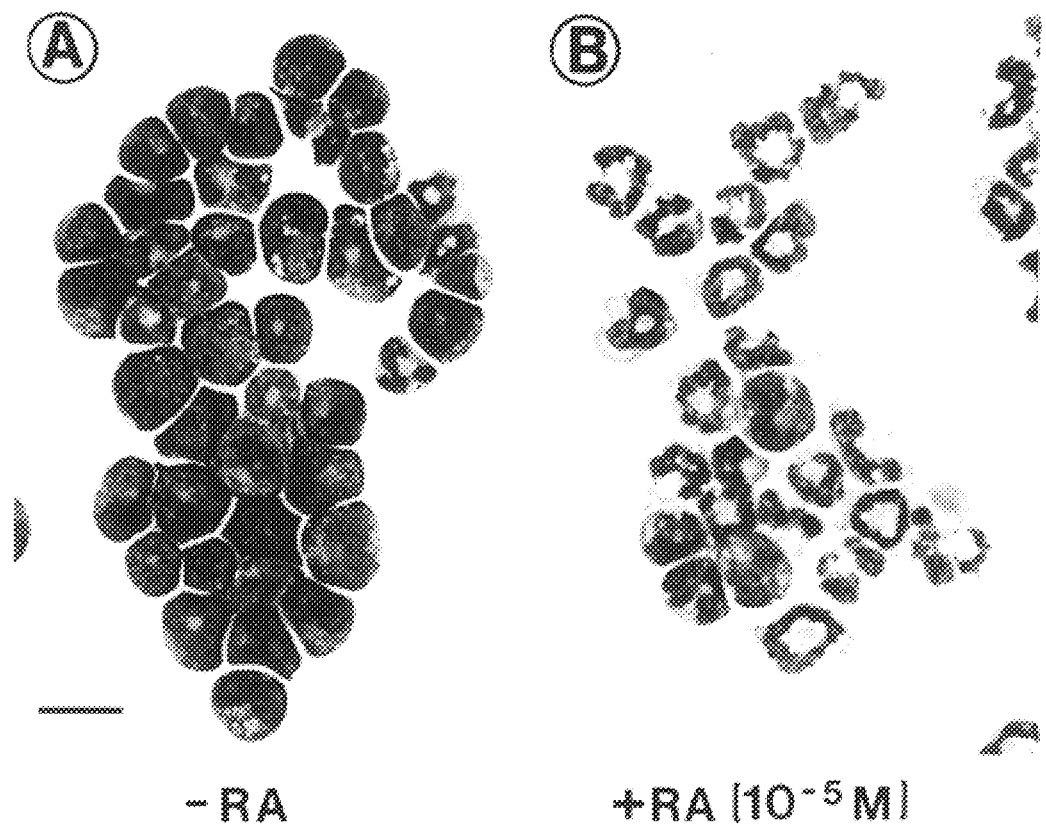
FIG. 13A presents a photomicrograph showing the morphology of uninduced MPRO cells derived from LRARα403SN-infected BDF$_1$ bone marrow. Note the presence of few mature neutrophils. The MPRO cells have a tendency to form aggregates.
FIG. 13B presents a photomicrograph showing MPRO cells treated with $10^{-5}$M RA for 4 days. Cells with doughnut-shaped nuclei and pale cytoplasm are differentiated neutrophils. Two metamyelocytes are seen in the center field. Bar=20 μm.
Figure 14A:
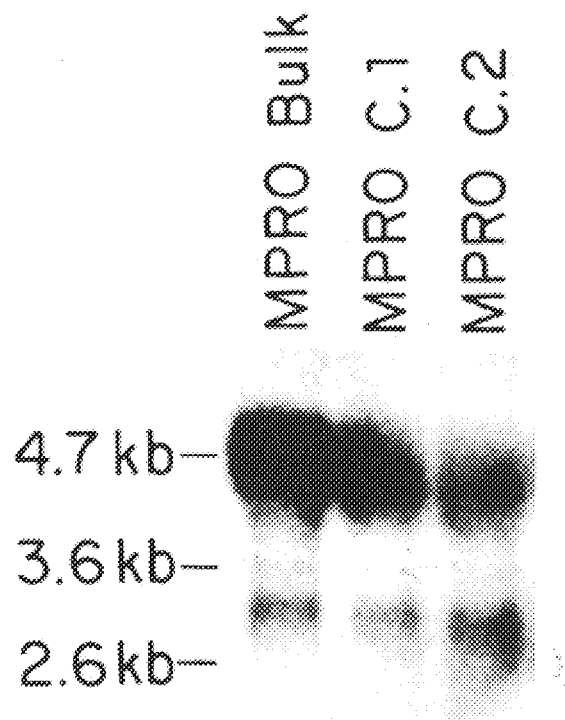
FIG. 14A shows Northern analysis of the expression of RARα403 in MPRO cells. Ten micrograms of RNA from bulk culture of MPRO cells as well as two clonal lines (c.1 and c.2) were applied to each lane and hybridized with a RARα probe. The 4.7-kb full-length viral RNA containing the RARα403 sequence and the 3.6- and 2.6-kb endogenous RARα are indicated.

To determine whether the dominant negative RARα403 can block the differentiation of normal mouse neutrophil precursors, we infected freshly harvested mouse bone marrow cells with the LRARα403SN or LXSN (control) retroviral vectors by a 3-day co-cultivation. The infected cells were subsequently selected in a medium containing G418 and GM-CSF. The LXSN (control)-infected mouse bone marrow cells proliferate and terminally differentiated into neutrophils, macrophages, and eosinophils with all cells dying after 10–14 days (FIG. 12). In contrast, numerous cells in the LRARα403SN-infected marrow culture continued to proliferate after 14 days and stayed immature in morphology. These proliferating cells exhibited promyelocyte characteristics (FIG. 13A) including the presence of numerous azurophilic primary granules, cell surface expression of mouse neutrophIL-specific antigen 7/4 (28), and positive staining for chloroacetate esterase. They have proliferated continuously as a GM-CSF-dependent cell line for over 9 months to date and are referred to as the "MPRO" (for mouse promyelocyte) cell line. Northern blot analysis indicates that the MPRO cells express high levels of retroviral mRNA harboring the truncated RARα403 sequence (FIG. 14A). The inventors were unable to isolate cell lines isolated from LXSN-infected cultures.

The MPRO cell line was deposited under accession number CRL 11422 on Jul. 27, 1993, at the American Type Culture Collection, 12301 Parklawn Drive, Rockville, Md. 20852.

EXAMPLE 12

Cells exhibit diminished RA responsiveness but differentiate into mature neutrophils with high concentrations of RA.

Figure 15:
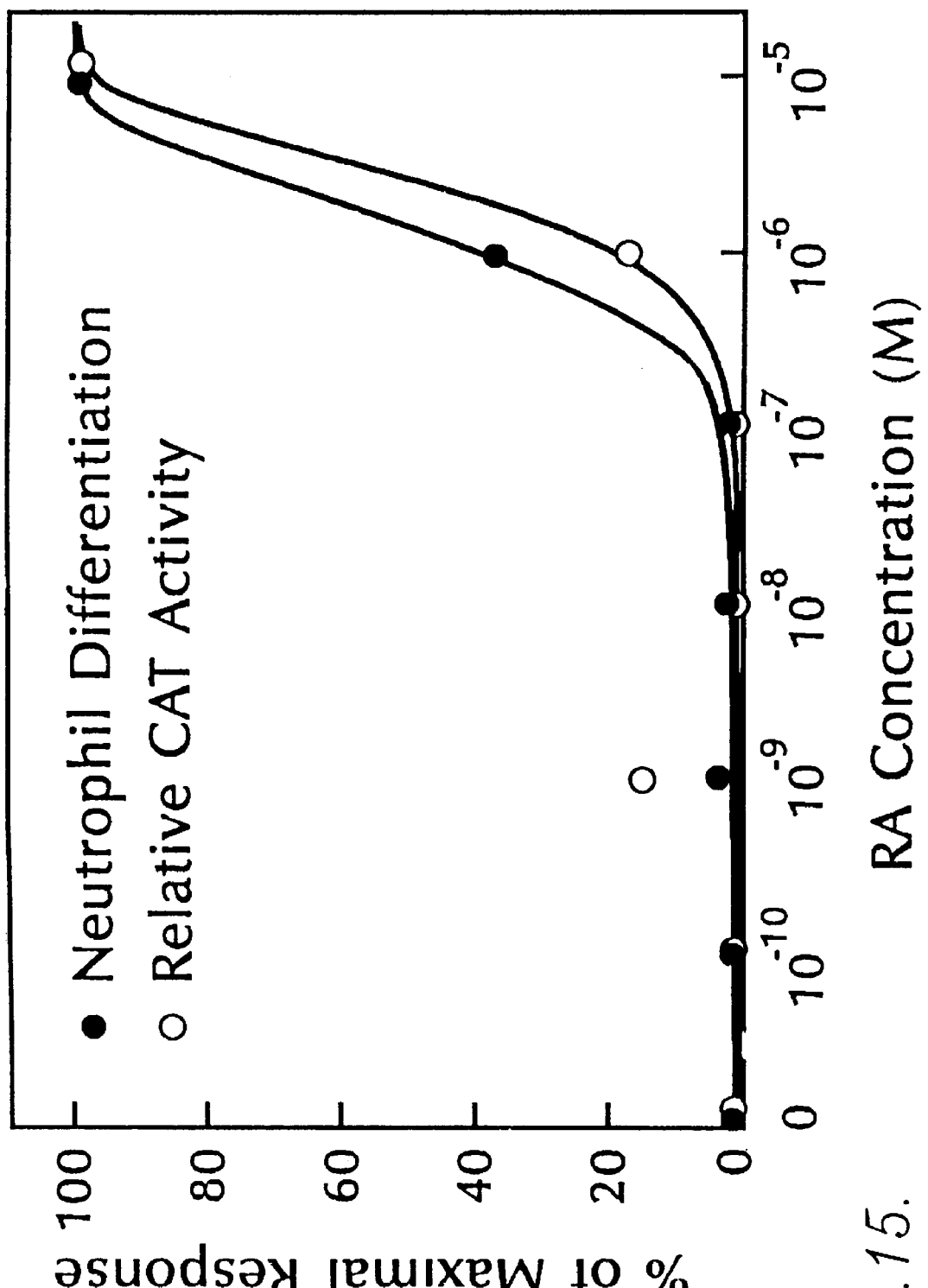
FIG. 15 graphically depicts the dose-response curves of RA-induced neutrophil differentiation (solid circles) and transactivation of pRRE$_4$-CAT (open circles) in MPRO cells. Mean of duplicates.

Like GMB cells, the MPRO cells have a greatly reduced RA responsiveness in transient expression assays using the pRRE$_4$-CAT reporter. The half-optimal concentration of RA is about $2 \times 10^{-6}$M and the optimal concentration is $10^{-5}$M (FIG. 15). Similar to the GMB cells derived from the FDCP mix A4 cell line, treatment of MPRO cells with high concentrations of RA ($10^{-5}$M) induces them to terminally differentiate into mature neutrophils (FIG. 13B). As with the GMB cells, the dose-response curve of RA-induced neutrophil differentiation of the MPRO cells is almost identical to that of the transactivation of pRRE$_4$-CAT in these target cells (FIG. 15).

EXAMPLE 13

Multiclonal origin of the MPRO cells.

Figure 14B:
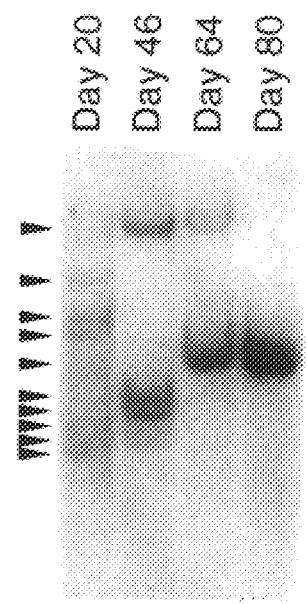
FIG. 14B shows Southern analysis of the LRARα403 3SN-infected BDF$_1$ bone marrow cells. Genomic DNAs were collected at indicated times after infection and GM-CSF stimulation (as described for FIG. 12), digested with EcoRI and subjected to Southern hybridization using a Neo probe. Multiple bands (at least 7) were visible on day 20 (by then all the growing cells are blocked promyelocytes) with at least 5 bands visible on day 46. One clone eventually dominated the culture by day 80. Arrowheads point to all visible bands.

The rapid emergence of large numbers of promyelocytes in LRARα403SN-infected, GM-CSF-stimulated primary mouse bone marrow cells by day 20 suggests a multiclonal origin of these MPRO cells. Indeed, when genomic DNA from the emerging promyelocytes is digested with EcoRI (which cuts only once within the provirus) and subjected to Southern blot analysis with a provirus-specific probe (Neo), multiple bands are noted at day 20 and 46 after infection, confirming the polyclonal origin of the MPRO promyelocytes (FIG. 14B). The multiclonal origin of these promyelocytes indicates that it is the transduction of the dominant negative RARα403 construct per se rather than a rare genetic event that accounts for the block in neutrophil differentiation.

DISCUSSION OF EXAMPLES 7–13

Research in the past 20 years has demonstrated the importance of hematopoietic growth factors on the survival, proliferation, and differentiation of hematopoietic progenitors (40). In this and a previous report (52), we provide strong evidence that members (RARs in this case) of the steroid/thyroid hormone receptor superfamily also play significant roles in the differentiation of normal neutrophils. We have demonstrated that introducing a dominant negative RARα403 construct into the IL-3-dependent, multipotent FDCP mix A4 cells resulted in a shift from spontaneous neutrophil/macrophage differentiation to the preferential development along the basophil/mast cell lineage in the presence of IL-3 (52). Thus it appears that in the multipotent FDCP mix A4 cells, the differentiation along the neutrophil lineage is permitted or even promoted by normal RARs while the development along the mast cell lineage is inhibited. Suppression of endogenous RAR activity with the dominant negative RARα403 reverses this pattern (52).

In the study described in Examples 7–12, we first induced the LRARα403SN-infected FDCP mix A4 cells with GM-CSF which greatly increased the frequency of the commitment/differentiation along the neutrophil lineage. Under such growth conditions, many differentiating cells are blocked at the promyelocyte stage (Table 1; FIGS. 9 and 10A). Since we have observed that GM-CSF-induced neutrophil differentiation of the uninfected FDCP mix A4 cells requires physiological concentrations ($10^{-9}$ to $10^{-8}$M) of RA (FIG. 11A), the differentiation block exhibited by the LRARα403SN-transduced cells is probably due to inability of these cells to respond to the physiological concentrations of RA present in the culture medium (which contains 20% HS). Nevertheless, this differentiation block can be overcome by supra-physiological concentrations ($10^{-6}$ to $10^{-5}$M) of RA which induces virtually all cells to differentiate to mature neutrophils (FIG. 10B). This contrasts with the inability of similar concentrations ($10^{-5}$M) of RA to induce LRARα403SN-transduced HL-60 to differentiate (52). This may be due to the fact that the HL-60 cell line was originally derived from leukemia cells and may harbor mutations that decrease their RA responsiveness. Indeed, relatively high concentrations ($10^{-7}$–$10^{-6}$M) of RA are required to induce untransduced HL-60 cells to differentiate.

The mechanism by which the RARα403 construct exerts its dominant negative activity remains to be elucidated. It has been observed that RARα must dimerize with RXRS in order to function optimally (56, 60), and that a truncated RARα (RARα404, which differs from RARα403 by one amino acid at the C-terminus) can dimerize with RXRα (56). Thus it is very likely that the overexpressed RARα403 dimerizes with available RXRs in LRARα403SN-infected cells and thereby prevents the formation of functional RAR-RXR dimers. The differentiation response of GMB cells to supra-physiological concentrations ($10^{-6}$–$10^{-5}$M) of RA may be mediated by residual intact RAR-RXR heterodimers or via alternative pathways that are less affected by RARα403 and have a higher RA requirement.

We also demonstrate that infection of primary, normal mouse bone marrow cells with the LRARα403SN retroviral vector carrying the dominant negative receptor construct leads to a differentiation block at the promyelocyte stage with establishment of GM-CSF-dependent promyelocyte cell lines. Several considerations support the notion that the expression of the dominant negative RARα403 by itself is sufficient for this differentiation block: a) the viral producer cell lines are free of helper viruses that may induce additional mutations; b) the rapid emergence (within 14 days) of GMB or MPRO cells argues against accumulated spontaneous mutations that may contribute to the differentiation block; and c) Southern blot analysis of the proviral integration sites indicates multiclonal nature of MPRO cells in the early stages of establishment (day 20–46; FIG. 14B), thus making it unlikely that a common proviral insertional mutation or a second genetic event plays a role in generating the blocked promyelocyte phenotype. The capacity of the dominant negative construct alone to inhibit GM-CSF-induced neutrophil differentiation of normal mouse bone marrow cells provides strong evidence that RAR activity is essential for normal neutrophil differentiation.

It is intriguing that the arrested promyelocyte phenotype that characterizes the GM-CSF-dependent GMB and MPRO cells (expressing the dominant negative RARα403 construct) is similar to the phenotype of human acute promyelocytic leukemia (APL) cells (which express the aberrant PML-RARα fusion gene). Both the infected mouse cell lines and human APL cells are blocked at the same developmental stage and both can be induced to terminally differentiate with supra-physiological concentrations of RA. Since the differentiation block in the GMB and MPRO cells is attributable to the dominant negative activity of the transduced RARα403 construct, this phenotypic similarity among GMB, MPRO, and APL cells suggests that the aberrant PML-RARα fusion protein (or the reciprocal translocation product RARα-PML) that characterizes most cases of human APL might also exert dominant negative activity in neutrophil precursors. However, data published to date indicate that PML-RARα does not consistently repress RAR activity in transactivation assays using various target cells (18, 32). It is possible that the dominant negative activity of PML-RARα (or the reciprocal translocation product RARα-PML) may be cell type-, developmental stage- and promoter-specific. If so, the system described here may be suitable for examining these possibilities.

EXPERIMENTAL PROCEDURES

EXAMPLES 7–13

Cell Lines

FDCP mix A4 cells (generously provided by Drs. Elaine Spooncer and Michael Dexter) (48) are maintained in Iscove's Modified Dulbecco's Medium (IMDM; Gibco) supplemented with 20% (v/v) horse serum (HS; Flow Laboratory) and 10% (v/v) WEHI 3B conditioned medium as a source of IL-3.

Mouse Bone Marrow

Six-week-old male $BDF_1$ mice (Jackson Laboratory) are injected intraperitoneally with 5-fluorouracil (5-FU) at 100 mg/kg body weight five days prior to bone marrow harvest. Light-density marrow cell fraction containing hematopoietic progenitors are collected by density centrifugation through Nycodenz (Specific gravity 1.080; Robbins Scientific).

Retroviral Vectors and Producer Cell Lines and Reporter Constructs

The construction of retroviral vectors LXSN, LRARαSN, LRARα403SN (all three contain the neomycin resistance gene) and the establishment of helper virus-free amphotropic retroviral producer cell lines PA317/LXSN, PA317/LRARαSN, and PA317/LRARα403 3SN are described above in Examples 1–6. $pRRE_4$-CAT is a reporter construct containing the retinoic acid response element (RRE) of RARα (17) and the chloramphenicol acetyltransferase (CAT) gene. pCMV-GH contains human growth hormone gene driven by the promoter of early immediate gene of cytomegalovirus (24) and is used to normalize transfection efficiency.

Retroviral Infection and G418 Selection

FDCP mix A4 cells are infected by a 24-hour co-cultivation with irradiated (1100 rad) retroviral producer cell lines in growth medium containing polybrene (4 μg/ml), followed by G418 selection (300 μg/ml) for 8–10 days. Post-5-FU, light-density $BDF_1$ marrow cells are infected by co-cultivation with unirradiated, subconfluent producer cells for 3 days in IMDM supplemented with 20% (v/v) HS, 4 μg/ml polybrene, 20% (v/v) WEHI 3B conditioned medium, 2.5 ng/ml GM-CSF (Immunex), 10 ng/ml human interleukin-1α, and 20 ng/ml human interleukin-6 (Amgen). At least 13% of LXSN-infected and 5% of LRARα403SN-infected marrow colony-forming cells are G418-resistant as determined by colony assays in soft agar.

Transient Expression Assay

Radioimmunoassay of human growth hormone and chloramphenicol acetyltransferase (CAT) assay are performed as detailed previously (52). For electroporation of FDCP mix A4 and GMB cells, the following parameters are used: $10^7$ cells, 60 μg each of pCMV-GH and $pRRE_4$-CAT, 800 volt/25 μF. For MPRO cells the following parameters are used: $10^7$ cells, 75 μg each of pCMV-GH and $pRRE_4$-CAT, 250 volt/960 μF. Conditioned medium and cell lysate are collected 40 hours later for growth hormone quantitation and CAT assay as previously described (52).

Southern and Northern Blots

Genomic DNA obtained at different times of the establishment of MPRO cells are digested with EcoRI, electrophoresed (30 μg per lane) and blotted onto nitrocellulose and hybridized with a radiolabelled Neo probe. For Northern analysis, 10 μg of total RNAs are electrophoresed, blotted and hybridized with a radiolabelled human RARα probe.

EXAMPLE 14

Kostmann syndrome is a lethal congenital neutropenic syndrome characterized by severe recurrent infections and death in early childhood. Examination of bone marrow in these patients shows many immature stages of neutrophils.

Two boys with Kostmann syndrome were studied. A high-density fraction of bone marrow cells was recovered by centrifugal elutriation and cultured in IMDM medium containing 20% horse serum and 10 ng/ul GM-CSF (i.e., conditions suitable for differentiation of precursors in normal marrow into neutrophils). Parallel cultures were established in the absence or presence of all-trans retinoic acid (ATRA). The cultures were monitored by microscopic examination and cytochemical methods as described in the Examples above. In the absence of ATRA there was little to no visible microscopic evidence for differentiation of the patient bone marrow cells into neutrophils. In the presence of 1 to 10 micromolar concentrations of ATRA (e.g., 10 ng/ml) significantly increased percentages of neutrophils were observed after 7 to 9 days of culture. No toxicity was observed in any cultures at 1 to 10 micromolar concentrations of ATRA.

These results suggest that patients with Kostmann syndrome may experience a block in terminal differentiation of neutrophils that is similar to that observed above in the MPRO cell line. Further, the results suggest that this block in terminal differentiation can be overcome through the therapeutic use of retinol compounds, and preferably by administration of a retinol compound in combination therapy with G-CSF or GM-CSF. It is likely that G-CSF in combination with ATRA may produce better clinical results than G-CSF above, and/or that the co-administration of ATRA may allow use of lower doses of G-CSF.

EXAMPLE 15

Establishment of a stem cell factor-dependent cell line (EML).

About $10^5$ bone marrow cells of male $BDF_1$ mice were infected with the retroviral vector LRARα403SN and subsequently cultured in Iscove's Modified Dulbecco's Medium (IMDM) supplemented with 20% (vol./vol.) horse serum, 20% WEHI 3B conditioned medium (vol./vol.; as a source of murine IL-3), murine GM-CSF (2.5 ng/ml; Immunex), human IL-1β (10 ng/ml; Amgen), human IL-6 (20 ng/ml; Amgen), and polybrene (4μg/ml), which enhances retroviral adhesion. In the initial isolation of EML cells, only $10^5$ bone marrow mononuclear cells were used in the co-culture infection; in later experiments, $10^6$ cells were used. Infected cells were subsequently cultured in IMDM supplemented with 20% horse serum, rat SCF (200 ng/ml; Amgen), 0.25% WEHI-3B-conditioned medium and human Epo (8 units/ml; Amgen). Cells were subcultured every 2–3 days. EML cells became the dominant cell type in one and a half to two months. Higher concentrations of WEHI conditioned medium promoted the growth of mast cells which seemed to retard the emergence of EML-like cells. Cell lines established from LRARα403SN or LRARα403SHD-infected cultures were maintained in IMDM supplemented with 20% horse serum and rat SCF (200 ng/ml; Amgen) alone. Subcloning of the cell line was carried out first by limiting dilution at 0.4 clonogenic cells per well in 96-well plates. Lines obtained by limiting dilution cloning were recloned (300 cells per 35-mm dish) in semisolid culture medium containing 0.8% methylcellulose plus SCF (200 ng/ml) once (EML C1) or twice (EML C1.1–1.4). Individual colonies were picked with the aid of an inverted microscope and expanded in IMDM/20% horse serum/SCF (200 ng/ml). The EML C1 cell line was deposited under accession number CRL 11691 on Jul. 25, 1994, at the American Type Culture Collection, 12301 Parklawn Drive, Rockville, Md., 20852.

EXAMPLE 16

Induction of B lymphoid, erythroid, and myeloid differentiation.

The stromal cell line W20 was established from the bone marrow of a W(+/+) mouse and then subcloned four times (Tsai, 1986). A clonal line W20 F1 was used in this experiment. These cells are adherent and have extensive, veil-like cytoplasm. Upon confluency, W20 cells undergo adipogenesis. W20 cells are maintained in Dulbecco's Modified Eagle's medium (DME) supplemented with 10% FCS. To induce B cell differentiation, $10^6$ EML cells that had been washed twice with phosphate buffered saline (PBS) to remove SCF were added to a subconfluent layer of W20 grown in a 6-well plate and fed with RPMI 1640 supplemented with 5% FCS, $5\times10^5$M 2-mercaptoethanol and human IL-7 (100 units/ml; Immunex) every 2–3 days. Total RNAs and genomic DNAs were prepared from the stromal cell EML cell co-cultures without separation of the two cell types.

For induction of erythroid differentiation in liquid culture, EML cells were cultured in IMDM supplemented with 20% horse serum, SCF (200 ng/ml) and Epo (8 units/ml). Benzidine (Sigma) staining was performed as described (Orkin et al., 1975). For BFU-E assay, EML cells were cultured in 0.8% methylcellulose culture medium supplemented with 20% horse serum, SCF (200 ng/ml) and Epo (8 units/ml).

For induction of CFU-GM, the EML cells were cultured in IMDM supplemented with 20% horse serum, rat SCF (200 ng/ml) plus 5% WEHI conditioned medium. Cultures were treated with all-trans RA at various concentrations for 72–96 hours. Cells were then washed three times with PBS to remove RA and recultured in IMDM/methylcellulose (0.8%) supplemented with 20% horse serum and murine GM-CSF (10 ng/ml) for CFU-GM assay, or SCF (200 ng/ml) for detecting self-renewing clonogenic cells, or SCF plus Epo (8 units/ml) for BFU-E assay.

EXAMPLE 17

Establishment of neutrophilic promyelocyte cell lines (EPRO) from EML.

EML cells induced with RA plus IL-3 were washed to remove RA and then cultured directly in liquid medium (IMDM/20% horse serum) plus GM-CSF (10 ng/ml). Most cells died upon shifting to GM-CSF, while CFU-GMs proliferated and differentiatied into neutrophils, promyelocytes and macrophages. After 2–3 weeks, most of the growing cells were promyelocytes which depended on GM-CSF (10 ng/ml) for survival and proliferation. Alternatively, individual CFU-GM colonies (described in EXAMPLE 16) were picked from the methylcellulose culture and expanded in liquid medium containing GM-CSF. Subcloning was done in methylcellulose supplemented with 20% horse serum and GM-CSF (10 ng/ml).

EXAMPLE 18

Southern and Northern analyses.

For Southern analyses of the number and sites of proviral integrants, genomic DNA samples were isolated from various cell lines and digested with EcoRI, electrophoresed (25 μg/lane), blotted onto nitrocellulose, and hybridized with $P_{32}$ nick-translated 0.9-kb neo probe. The correct size of the provirus within all cell lines was also verified by digestion with SmaI (which cut only within the long terminal repeats of the provirus) and analyzed by Southern analysis using neo as the probe. Northern blots of total RNAs from various cell lines and tissues were hybridized with the following nick-translated probes: a 0.3-kb SalI-KpnI fragment of $IgC\mu_3$ genomic DNA clone encoding the third exon of the mouse Ig H constant region gene and was provided by Gregory Warr; a 0.95-kb BglII fragment containing part of the coding region of a mouse RAG-1 genomic clone and was provided by Roger Perlmutter and Steve Anderson; a mouse $\beta_{major}$ globin cDNA probe obtained from Mark Groudine; and a 226-bp fragment of the $J_3$ segment of mouse IgH gene prepared as described in EXAMPLE 19. Procedures used for this example were standard methods (45).

EXAMPLE 19

PCR detection of D–J rearrangements.
The primers for PCR detection of D–J rearrangements were:
DHL: GMTTTTTGTSAAGGGATCTACTACTGTG;
J3: TTCTCACAAGAGTCCGATAGACCCTGG;
(5'-3'; M=A or C; S=C or G)

These primers, previously known in the art, flank the region of the immunoglobulin molecule that undergoes rearrangement (46a). Each 100-μl PCR reaction contained 0.2 μg of spleen genomic DNA or 2 μg of test template DNAs, 10 mM Tris (pH 8.3 at room temperature), 50 mM KCL, 1.5 mM $MgCl_2$, 0.01% gelatin, 100 ng of each primer, and 1 unit of Taq polymerase (Amplitaq; Cetus).

CITATIONS

1. Alcalay, M., D. Zangrilli, P. Pandolfi, L. Longo, A. Mencarelli, A. Giacomucci, M. Rocchi, A. Biondi, A. Rambaldi, F. Lo Coco, D. Diverio, E. Donti, F. Grignani, and P. Pelicci. 1991. Translocation breakpoint of acute promyelocytic leukemia lies within the retinoic acid receptor α locus. *Proc. Natl. Acad. Sci. USA* 88:1977–1981.
2. Borrow, J., A. D. Goddard, D. Sheer, and E. Solomon. 1990. Molecular analysis of acute promyelocytic leukemia breakpoints cluster region on chromosome 17. *Science* 249:1577–1580.
3. Breitman, T. R., S. E. Selonick, and S. J. Collins. 1980. Induction of differentiation of the human promyelocytic leukemia cell line (HL-60) by retinoic acid. *Proc. Natl. Acad. Sci. USA* 77:2936–2940.
4. Castaigne, S., C. Chornienne, M. T. Daniel, P. Ballerini, R. Berger, P. Fenaux, and L. Degos. 1990. All-trans retinoic acid as a differentiation therapy for acute promyelocytic leukemia. I. Clinical results. *Blood* 76:1704–1710.
5. Chomienne, C., P. Ballerini, N. Balitrand, M. Daniel, P. Fenaux, S. Castaigne, and L. Degos. 1990. All-trans retinoic acid in acute promyelocytic leukemias. II. In vitro studies: Structure-function relationship. *Blood* 76:1710–1717.
5a. Coffinan, R. L., and I. L. Weissman. 1981. B22: a B cell-specific member of the T200 glycoprotien family. *Nature* 289:681–683.
6. Collins, S. J., R. C. Gallo, and R. E. Gallagher. 1977. Continuous growth and differentiation of human myeloid leukaemic cells in suspension culture. *Nature* 270:347–349.
7. Collins, S., H. Coleman, and M. Groudine. 1987. Expression of bcr and bcr-abl fusion transcripts in normal and leukemic cells. *Mol. Cell. Biol.* 7:2870–2876.
8. Collins, S. J., K. Robertson, and L. Mueller. 1990. Retinoic acid-induced granulocytic differentiation of HL-60 myeloid leukemia cells is mediated directly through the retinoic acid receptor (RAR-α). *Mol. Cell. Biol.* 10:2154–2161.
9. Cullum, M., and M. Zile. 1986. Quantitation of biological retinoids by high-pressure liquid chromatography: primary internal standardization using tritiated retinoids. *Analytical Biochem.* 153:23–32.
10. Damm, K., C. C. Thompson, and R. M. Evans. 1989. Protein encoded by v-erbA functions as a thyroid-hormone receptor antagonist. *Nature* 339:593–597.
11. Davis, R., H. Weintraub, and A. Lassar. 1987. Expression of a single transfected cDNA converts fibroblasts to myoblasts. *Cell* 51:987–1000.
12. Denburg, J. A. 1992. Basophil and mast cell lineages in vitro and in vivo. *Blood* 79:846–860. (A review).
13. DeRuyter, M. G., W. Lambert, and P. DeLunheer. 1979. Retinoic acid: an endogenous compound of human blood. Unequivocal demonstration of endogenous retinoic acid in normal physiological conditions. *Analyt. Biochem.* 98:402–409.
14. Desbois, C., D. Aubert, C. Legrand, B. Pain, and J. Samarut. 1991. A novel mechanism of action for v-erbA: abrogation of the inactivation of transcription factor AP-1 by retinoic acid and thyroid hormone receptors. *Cell* 67:731–740.
15. de The, H., Marchio, A., Tiollais, P., & Dejean, A. (1989). *EMBO J.* 8:429433.
16. de The, H., Chommienne, C., Lanotte, M., Degos, L., & Dejean, A. (1990). *Nature* 347:558–561.
17. de The, H., Vivanco-Ruiz, M., Tiollais, P., Stunnenberg, H., & Dejean, A. (1990). *Nature* 343:177–180.
18. de The, H., A. Marchio, P. Tiollais, and A. Dejean. 1989. Differential expression and ligand regulation of the retinoic acid receptor α and á genes. *EMBO J.* 8:429–433.
19. de The, H., M. Vivanco-Ruiz, P. Tiollais, H. Stunnenberg and A. Dejean. 1990. Identification of a retinoic acid responsive element in the retinoic acid receptor α gene. *Nature* 343:177–180.
20. de The, H., C. Chomienne, M. Lanotte, L. Degos, and A. Dejean. 1990. The t(15;17) translocation of acute promyelocytic leukemia fuses the retinoic acid receptor α gene to a novel transcribed locus. *Nature* 347:558–561.
21. de The, H., C. Lavau, A. Marchio, C. Chomienne, L. Degos, and A. Dejean. 1991. The PML-RARα fusion mRNA generated by the t(15;17) translocation in acute promyelocytic leukemia encodes a functionally altered RAR. *Cell* 66:675–684.
22. Evans, R. 1988. The steroid and thyroid hormone receptor superfamily. *Science* 240:889–895.
23. Gallagher, R., F. Said, I. Pua, P. Papenhausen, E. Paietta, and P. Wiernik. 1989. Expression of retinoic acid receptor-α in human leukemia cells with variable responsiveness to retinoic acid. *Leukemia* 3:789–795.
24. Geballe, A., R. Spate and E. Mocarski. 1986. A cis-acting element within the 5' leader of a cytomegalovirus beta transcript determines kinetic class. *Cell* 46:865–876.
25. Giguere, V., E. Ong, P. Segui, and R. Evans. 1987. Identification of a receptor for the morphogen retinoic acid. *Nature* 330:624–629.
26. Herskowitz, I. 1987. Functional inactivation of genes by dominant negative mutations. *Nature* 329:219–222.
27. Heyworth, C. M., Dexter, T. M., Kan, O., & Whetton, A. D. (1990). *Growth Factors* 2:197–211.
28. Hirsch, S., and S. Gordon. 1983. Polymorphic expression of a neutrophil differentiation antigen revealed by monoclonal antibody 7/4. *Immunogenetics* 18:229–239.
29. Hong, W. K., S. M. Lippman, L. Itri, D. D. Karp, J. S. Lee, R. M. Byers, S. P. Schatz, A. M. Kramer, R. Lotan, L. J. Peters, I. W. Dimery, B. W. Brown, and H. Goepfert. 1990. Prevention of second primary tumors with isotretinoin in squamous cell carcinoma of the head and neck. *New Engl. J Med.* 323:795–801.
30. Huang, M.-E., Y.-C. Ye, S.-R. Chen, J.-R. Chai, J.-X. Lu, L. Zhoa, H.-T. Gu., and Z.-Y. Wang. 1988. Use of all-trans retinoic acid in the treatment of acute promyelocytic leukemia. *Blood* 72:567–572.
30a. Ikuta, K., Kina, T., MacNiel, I, Uchida, N., Peault, B., Chien, Y.-h., and I. L. Weissman. 1990. A developmental switch in thymic lymphocyte maturation potential occurs at the level of hamatopoietic stem cells. *Cell* 62:863–874.
31. Just, U., C. Stocking, E. Spooncer, T. M. Dexter, and W. Ostertag. 1991. Expression of the GM-CSF gene after retroviral transfer in hematopoietic stem cell line induces synchronous granulocyte-macrophage differentiation. *Cell* 64:1163–1173.
32. Kakizuka, A., W. Miller, K. Umesono, R. Warrell, S. Frankel, V. Murty, E. Dmitrovsky, and R. Evans. 1991. Chromosomal translocation t(15;17) in human acute promyelocytic leukemia fuses RARα with a novel putative transcription factor, PML. *Cell* 66:663–674.
32a. Kierney, P. C., and K. Dorshkind. 1987. B lymphocyte precursors and myeloid progenitors survive in diffusion chamber culture but B cell differentiation requires close association with stromal cells. *Blood* 70:1418–1424.
33. Kliewer, S., K. Umesono, D. J. Mangelsdorf, and R. M. Evans. 1992. Retinoid X receptor interacts with nuclear receptors in retinoic acid, thyroid hormone and vitamin D3 signaling. *Nature* 355:446–449.
34. Largman, C., K. Detmer, J. Corral, F. Hack, and H. Lawrence. 1989. Expression of retinoic acid receptor alpha mRNA in human leukemic cells. *Blood* 74:99–102.
35. Lavin, T. N., J. D. Baxter, and S. Horita. 1988. The thyroid hormone receptor binds to multiple domains of the rat growth hormone 5'-flanking sequence. *J. Biol. Chem.* 163:9418–9426.

36. Leid, M., P. Kastner, R. Lyons, H. Nakshatri, M. Saunders, T. Zacharewski, J. Y. Chen, A. Staub, and P. Chambon. 1992. Purification, cloning, and RXR identity of the HeLa cell factor with which RAR or TR heterodimerizes to bind target sequences efficiently. *Cell* 68:377–395.

36a. Lemischka, I. R., Raulet, D. H., and R. C. Mulligan. 1986. Developmental potential and behavior of hematopoietic stem cells. *Cell* 45:917–927.

37. Lotan, R. 1980. Effects of vitamin A and its analogs (retinoids) on normal and neoplastic cells. *Biochem. Biophys. Acta.* 605:33–91.

37a. Mangelsdorf et al. 1990. *Nature* 345:224–229.

37b. Mangelsdorf et al. 1991. *Cell* 66:555–561.

38. Martin, D. I. K., L. I. Zon, G. Mutter, and S. H. Orkin. 1990. Expression of an erythroid transcription factor in megakaryocytic and mast cell lineages. *Nature* 344:444–447.

39. Merriman, R. and J. Bertram. 1979. Reversible inhibition by retinoids of 3-methylcholanthrene-induced neoplastic transformation in C3H/10T clone 8 cells. *Cancer Res.* 39:1661–1666.

40. Metcalf, D. (1988). The Molecular Control of Blood Cells. (Harvard University Press, Cambridge, Ma.).

41. Metzger, H., G. Alcaraz, R. Hohman, J. Kinet, V. Pribula, and R. Ovarto. 1986. The receptor with high affinity for immunoglobulin IgE. *Annu. Rev. Immunol.* 4:419–470.

42. Miller, A. D. and G. J. Rosman. 1989. Improved retroviral vectors for gene transfer and expression. *Biotechniques* 7:980–990.

43. Miller, A. D. 1990. Retrovirus packaging cells. *Human Gene Therapy* 1:5–14.

44. Riley, J. F., and G. B. West. 1953. The presence of histamine in tissue mast cells. *J Physiol* 120:528–532.

45. Sambrook, J., E. Fritsch, T. Maniatis. 1989. Molecular Cloning: A Laboratory Manual. Cold Spring Harbor Laboratory Press.

46. Sap, J. A., A. Munoz, J. Schmitt, H. Stunnenberg, and B. Vennstrom. 1989. Repression of transcription mediated by a thyroid hormone response element by the v-erbA oncogene product. *Nature* 340:242–244.

46a. Schissel, M. S., Corcoran, L. M., and D. Baltimore. 1991. Virus-transformed pre-B cells show orderred activation but not inactivation of immunoglobulin gene rearrangement and transcription. *J Exp. Med.* 173:711–720.

47. Simeone, A., D. Acampora, L. Arcioni, P. Andrews, E. Boncinelli, and F. Mavilio. 1990. Sequential activation of HOX2 homeobox genes by retinoic acid in human embryonal carcinoma cells. *Nature* 346:763–766.

47a. Spangrude, G. J., Heimfeld, S., and I. L. Weissman. 1988. purification and characterization of mouse hematopoietic stem cells. *Science* 241:58–62.

48. Spooncer, E. C., Boettigen, D., & Dexter, T. M. (1984). *Nature* 310:228–230.

49. Spooncer, E., C. Heyworth, A. Dunn, and T. M. Dexter. 1986. Self-renewal and differentiation of interleukin-3-dependent multipotent stem cells are modulated by stromal cells and serum factors. *Differentiation* 31:111–118.

50. Thaller, C. and G. Eichele. 1987. Identification and spatial distribution of retinoids in the developing chick limb buds. *Nature* 327:625–628.

51. Thompson, H. L., D. D. Metcalfe, and J.-P. Kinet. 1990. Early expression of high affinity receptor for immunoglobulin E during differentiation of mouse mast cells and human basophils. *J Clin. Invest.* 85:1227–1233.

52. Tsai, S., Bartelmez, S., Heyman, R., Damm, K., Evans, R., & Collins, S. J. (1992). *Genes & Develop.* 6:2258–2269.

52a. Tsai, S., and S. J. Collins. 1993. A dominant negative retinoic acid receptor blocks neutrophil differentiation at the promyelocyte stage. *Proc. Natl. Acad. Sci. (U.S.A.)* 90:7153–7157.

53. Tsai, S.-F., D. Martin, L. Zon, A. D'Andrea, G. Wong, and S. Orkin. 1989. Cloning of cDNA for the major DNA-binding protein of the erythroid lineage through expression in mammalian cells. *Nature* 339:446–451.

54. Umesono, K., V. Giguere, C. Glass, M. Rosenfeld, and R. Evans. 1988. Retinoic acid and thyroid hormone induce gene expression through a common responsive element. *Nature* 336:262–265.

55. Warrell, R., S. Frankel, W. Miller, D. Scheinberg, L. Itri, W. Hittelman, R. Vyas, M. Andreef, A. Tafuri, A. Jakubowski, J. Gabrilove, M. Gordon, and E. Dmitrovsky. 1991. Differentiation therapy of acute promyelocytic leukemia with tretinoin (all trans retinoic acid). *New Engl. J. of Med.* 324:1385–1393.

55a. Wu, A. M., Till, J. E., Siminovitch, L., and E. A. McCulloch. 1968. Cytological evidence for a relationship between normal hematopoietic colony-forming cells and cells of lympoid system. *J. Exp. Med.* 127:455–464.

56. Yu, V. C., C. Delsert, B. Anderson, J. M. Holloway, O. V. Devary, A. M. Naar, S. Y. Kim, J.-M. Boutin, C. K. Glass, and M. G. Rosenfeld. 1992. RXRα: A coregulator that enhances binding of retinoic acid, thyroid hormone, and vitamin D receptors to their cognate response elements. *Cell,* 67:1251–1266.

57. Zelent, A., A. Krust, M. Petkovich, P. Kastner, and P. Chambon. 1989. Cloning of murine α and α retinoic acid receptors and a novel receptor predominantly expressed in skin. *Nature* 339:714–717.

58. Zenke, M., P. Kahn, C. Disela, B. Vennstrom, A. Leutz, K. Keegan, M. Hayman, H-R Choi, N. Yew, J. D. Engel, and H. Beug. 1988. v-erbA specifically suppresses transcription of the avian erythrocyte anion transporter (band 3) gene. *Cell* 52:107–119.

59. Zenke, M., A. Munoz, J. Sap, B. Vennstrom, and H. Beug. 1990. v-erbA oncogene activation entails the loss of hormone-dependent regulator activity of c-erbA. *Cell* 61:1035–1049.

60. Zhang, X.-k. B. Hoffmnan, P. B.-V. Tran, G. Graupner, and M. Pfahl. 1992. Retinoid X receptor is an auxiliary protein for thyroid hormone and retinoic acid receptors. *Nature,* 355:441–446

61. Zon, I. L., M. F. Gurish, R. Stevens, C. Mather, D. S. Reynolds, K. F. Austen, and S. H. Orkin. 1991. GATA-binding transcription factors in mast cells regulate the promoter of the mast cell carboxypeptidase A gene. *J. Biol. Chem.* 266:22948–22953.

61a. Zsebo, K. M., Wypych, J., McNeice, I. K., Lu, H. S., Smith, K. A., Karkare, S. B., Sachdev, R. K., Yuschenkoff, V. N., Birkett, N. C., Williams, L. R., Satyagal, V. N., Tung, W., Bosselman, R. A., Mendiaz, E. A., and K. E. Langley. 1990. Identification, purification, and biological characterization of hematopoietic stem cell factor from Buffalo rat liver-conditioned medium. *Cell* 63:195–201.

The embodiments of the invention in which an exclusive property or privilege is claimed are defined as follows:

1. A method for establishing an immortalized hematopoietic stem cell line comprising the steps:

(a) preparing a plurality of recombinant hematopoietic stem cells by introducing into a source of recipient primary hematopoietic cells nucleic acid encoding a dominant negative suppressor of a retinoic acid receptor-alpha; and (b) culturing said recombinant cells in a culture medium comprising a growth factor until stem cells have become the dominant cell type wherein said dominant cells are immortalized stem cells.

2. The method of claim 1, wherein the immortalized cell line comprises SCF-dependent lympho-hematopoietic progenitor cells capable of differentiating into erythroid, myeloid, and B-lymphocytic lineages.

3. The method of claim 1, wherein the immortalized cell line comprises a GM-CSF dependent neutrophilic progenitor cell line comprising a plurality of myeloid cells capable of differentiating into neutrophils but not into monocytes, mast cells, or basophils, and in which the culture medium contains a level of retinoic acid of less than about $10^{-8}$M to about $10^{-9}$M.

4. The method of claim 1, wherein at least one retroviral vector is used to introduce the nucleic acid encoding the dominant negative suppressor of the retinoic acid receptor-alpha into the recipient hematopoietic cells.

5. The method of claim 1 which further comprises introducing a selectable marker into the recipient hematopoietic cells.

6. The method of claim 1, wherein the dominant negative suppressor of the retinoic acid receptor-alpha is selected from among nucleic acids encoding a RARα retinoic acid binding region, a RARα DNA binding region, a RARα amino terminus, and a RARα carboxy terminus.

7. A lympho-hematopoietic stem cell line established by the method of claim 2.

8. The lympho-hematopoietic stem cell line EML C1 (ATCC No. CRL 11691).

9. A neutrophil progenitor cell line established by the method of claim 3.

10. The MPRO cell line ATCC No. CRL 11422.

11. A method for inducing the lympho-hematopoietic stem cell line of claim 7 to differentiate into B lymphoid cells, comprising co-culturing the cells with bone marrow stromal cells and IL-7.

12. The method of claim 1, wherein the recipient hematopoietic cells are bone marrow cells.

* * * * *

UNITED STATES PATENT AND TRADEMARK OFFICE
CERTIFICATE OF CORRECTION

PATENT NO. : 5,830,760　　　　　　　　　　Page 1 of 5
DATED : November 3, 1998
INVENTOR(S) : S. Tsai et al.

It is certified that error appears in the above-identified patent and that said Letters Patent is hereby corrected as shown below:

| COLUMN | LINE | |
|---|---|---|
| [56] 1, col. 1 | Refs. Cited (Other Publs., Item 2) | "270;" should read --270:-- |
| [56] 1, col. 1 | Refs. Cited (Other Publs., Item 7) | "promelocytic" should read --promyelocytic-- |
| [56] 1, col. 2 | Refs. Cited (Other Publs., Item 11) | "Kan ,and" should read --Kan, and-- |
| [56] 1, col. 2 | Refs. Cited (Other Publs., Item 17) | "DNA-b-inding" should break as follows --DNA-binding-- |
| [56] 1, col. 2 | Refs. Cited (Other Publs., Item 21) | "et al. ," should read --et al.,-- |
| 4 | 56 | "cotransfected" should read --co-transfected-- |
| 5 | 15 | "LRARα403 SN" should read --LRARα403SN-- |

UNITED STATES PATENT AND TRADEMARK OFFICE
CERTIFICATE OF CORRECTION

PATENT NO. : 5,830,760

DATED : November 3, 1998

INVENTOR(S) : S. Tsai et al.

Figure 19C:
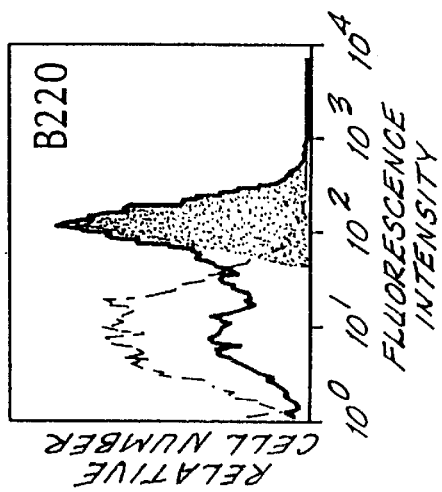
FIGS. 19A–F summarizes a flow cytometry cell surface antigen analysis of the C1 clone of EML cells using a panel of monoclonal antibodies.
Figure 19F:
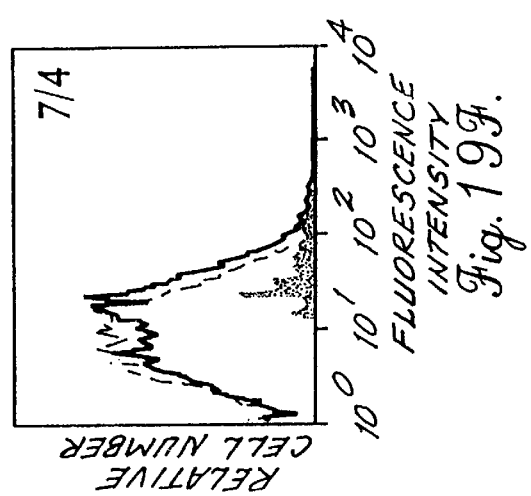
Figure 19B:
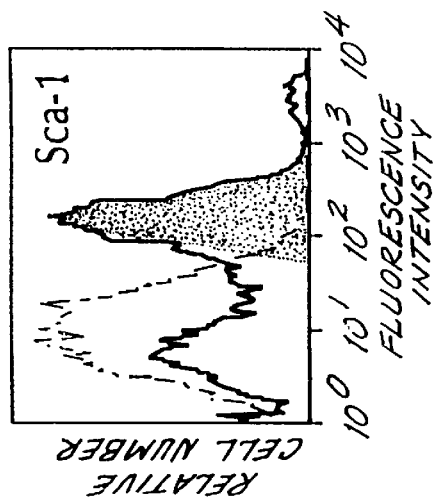
Figure 19E:
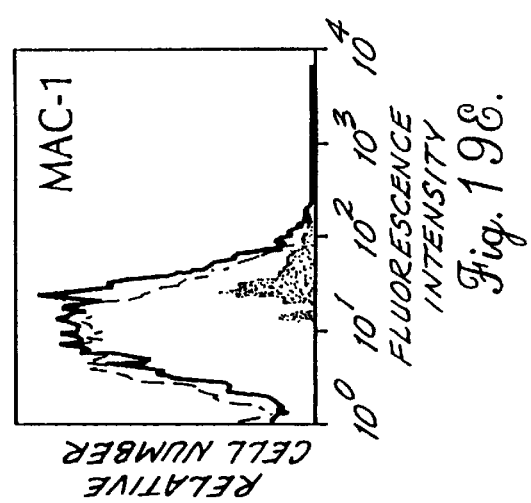
Figure 19A:
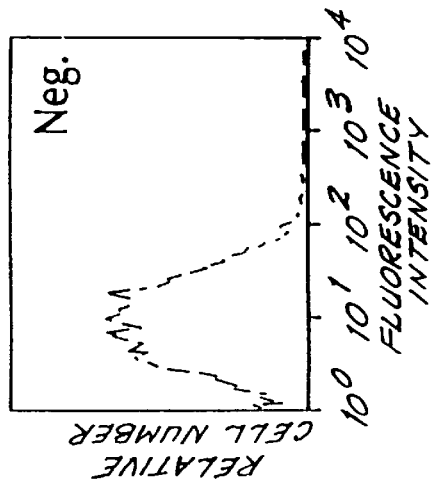
Figure 19D:
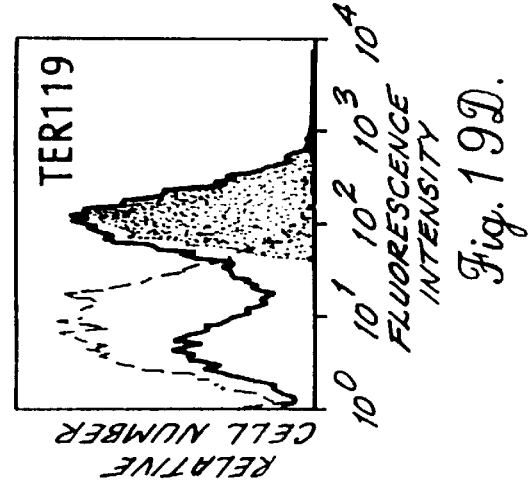
Figure 20A:
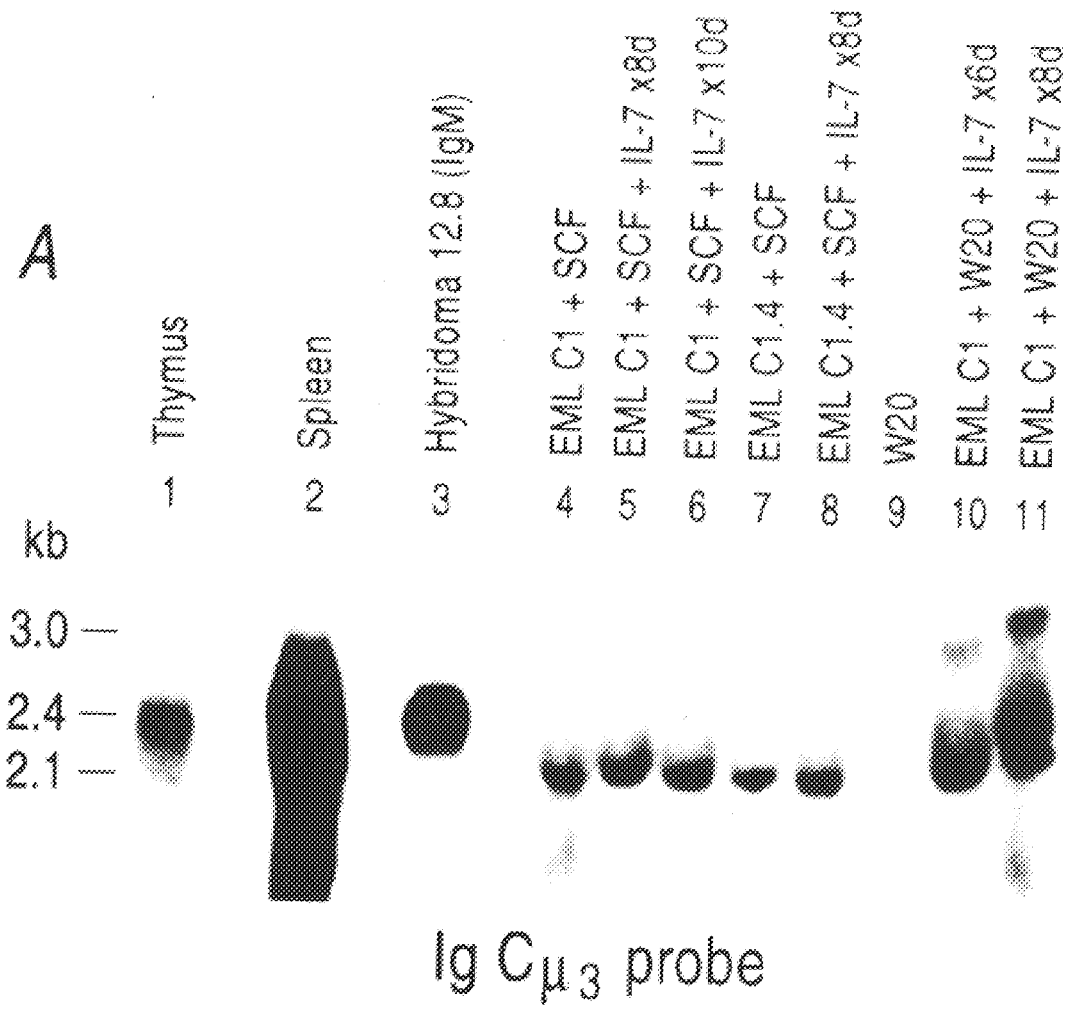
FIG. 20 depicts Northern blots analyzing the expression of immunoglobulin heavy chain genes in EML cells. When the EML cells were maintained in SCF alone, expression was detected of the 2.1- and 3.0-kb mRNAs corresponding to the MuO and Iμ transcripts of the unrearranged germline heavy chain genes (FIG. 20(A), lane 4).
FIG. 20(B), lanes 5 and 6 show that EML cells stimulated with SCF and IL-7 but not stromal cells reveal relatively small increases in recombination activating gene mRNA (RAG-1) expression, while lanes 10 and 11 illustrate that EML cells stimulated with stromal cells in addition to the SCF and IL-7 express higher levels of RAG-1.
Figure 20B:
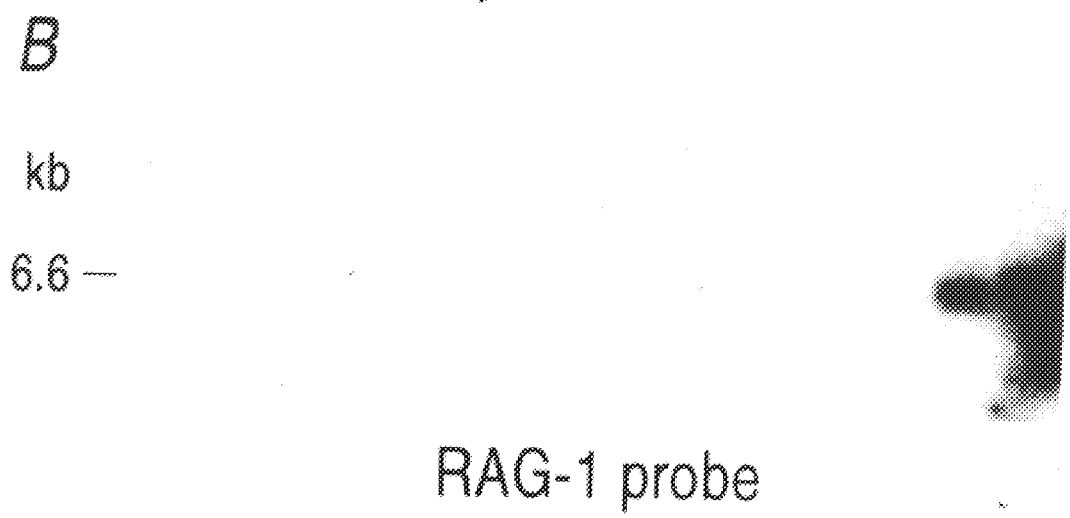
Figure 21A:
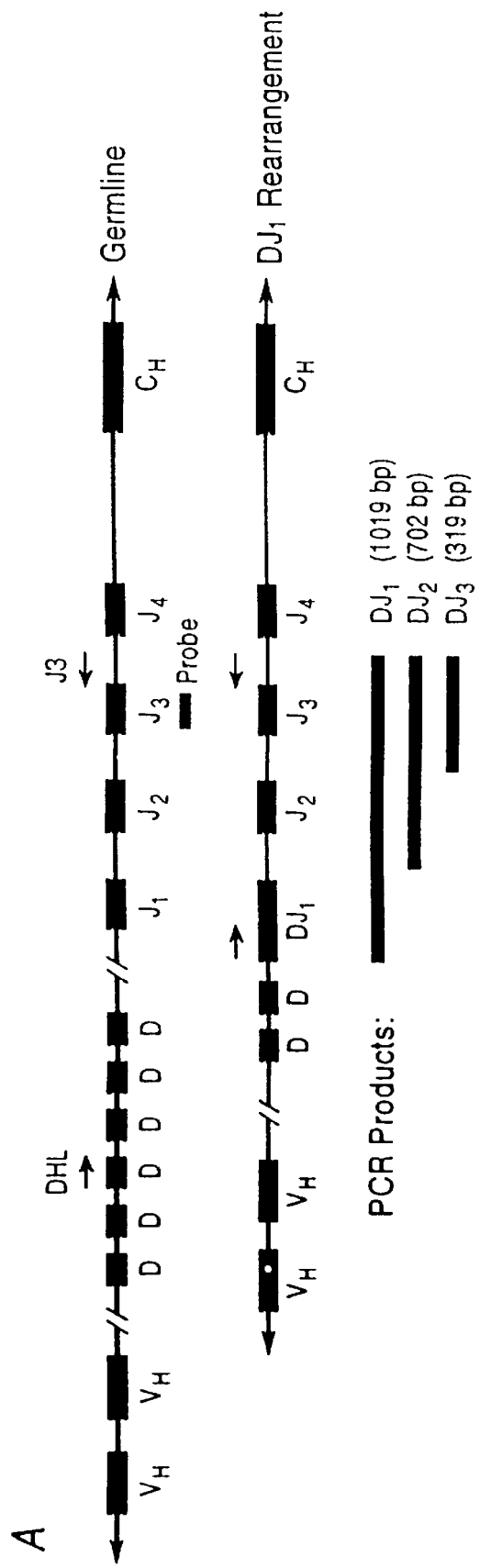
FIG. 21(A) illustrates the PCR products expected from nonrearranged and rearranged D–J regions.
Figure 21B:
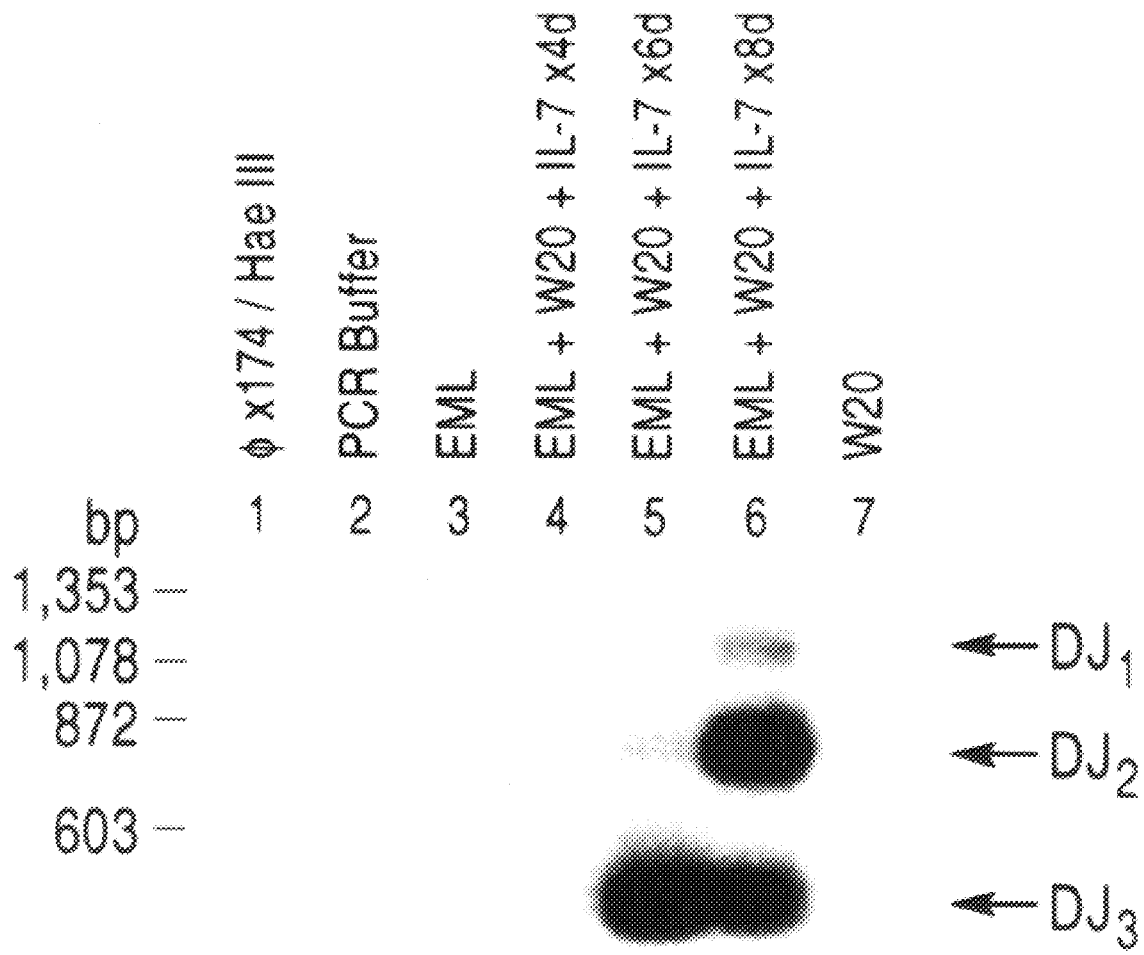
FIG. 21 illustrates the results of a PCR analysis conducted to determine whether or not D–J rearrangements had occurred in the B-cell progenitors present in SCR-maintained EML cells.
Figure 22A:
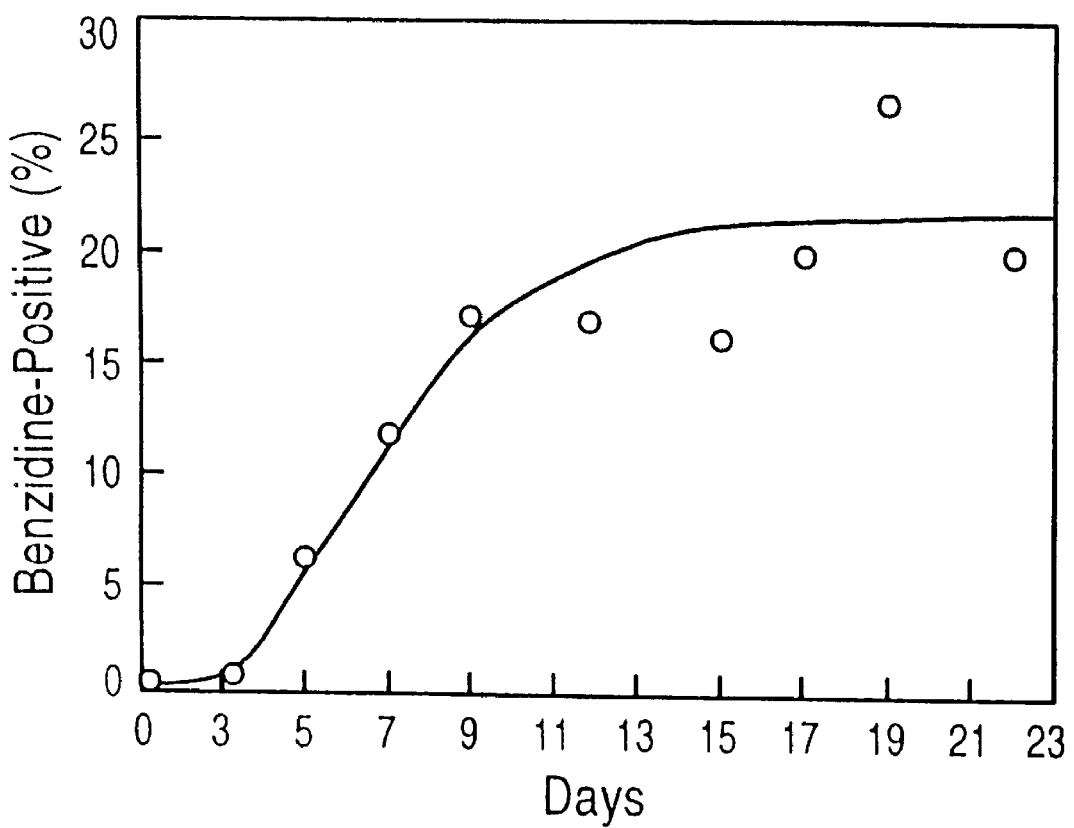
FIG. 22(A) graphically indicates that about 20% of the cells were positive when stained with benzidine, a dye that interacts with hemoglobin.
Figure 22B:
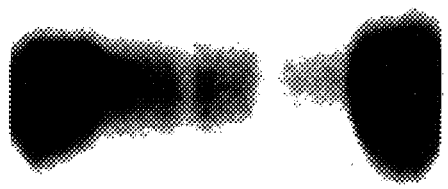
FIG. 22(B) illustrates similarly that these same EM:L cells expressed levels of globin mRNA comparable to that of murine erythroleukemia cells (MEL cells) that had been induced with hexamethylene bis-acetamide (HMBA) to produce hemoglobin.

It is certified that error appears in the above-identified patent and that said Letters Patent is hereby corrected as shown below:

| COLUMN | LINE | |
|---|---|---|
| 5 | 25 | "GATA -1" should read --GATA-1-- |
| 6 | 7 | "α" should read --RARα-- |
| 6 | 30 | "LRARα403 3SN" should read --LRARα403SN-- |
| 7 | 24 | "LRARα403 3SN" should read --LRARα403SN-- |
| 8 | 7 | "Anti-Sca-1, which FIG.19(B)" should read --FIG. 19(B) Anti-Sca-1, which-- |
| 8 | 35 | "FIG. 21 ((B)" should read --FIG. 21(B)-- |
| 8 | 46 | "EM:L" should read --EML-- |
| 10 | 54 | "stein" should read --stem-- |
| 12 | 15 | "Trim-ethymethoxyphenyl" should read --Tri-methymethoxyphenyl-- |
| 14 | 58 | "exog-enous" should read --exo-genous-- |

UNITED STATES PATENT AND TRADEMARK OFFICE
CERTIFICATE OF CORRECTION

PATENT NO. : 5,830,760
DATED : November 3, 1998
INVENTOR(S) : S. Tsai et al

It is certified that error appears in the above-identified patent and that said Letters Patent is hereby corrected as shown below:

| COLUMN | LINE | |
|---|---|---|
| 15 | 43 | "nix" should read --mix-- |
| 16 | 55 | "cytod-ifferentiation" should read --cyto-differentiation-- |
| 18 | 39 | "RARα" should read --RAR-- |
| 19 | 37 | after "RARα" delete "a" |
| 19 | 52 | "LRARα403 3SN" should read --LRARα403SN-- |
| 20 | 49 | "intrac-ellular" should read --intra-cellular-- |
| 21 | 6 | "LRARα403 3SN" should read --LRARα403SN-- |
| 22 | 34 | "Differeinial" should read --Differential-- |
| 24 | 55 | "param-eters" should read --para-meters-- |

UNITED STATES PATENT AND TRADEMARK OFFICE
CERTIFICATE OF CORRECTION

PATENT NO. : 5,830,760            Page 4 of 5
DATED : November 3, 1998
INVENTOR(S) : S. Tsai et al.

It is certified that error appears in the above-identified patent and that said Letters Patent is hereby corrected as shown below:

| COLUMN | LINE | |
|---|---|---|
| 24 | 56 | "LRARα403 3SN" should read --LRARα403SN-- |
| 26 | 54 | "2.5.µg" should read --2.5 µg-- |
| 27 | 5 | "LRARα403 3SN" should read --LRARα403SN-- |
| 27 | 49 | "LRARα403 3SN" should read --LRARα403SN-- |
| 28 | 2 | after "$O_2$," insert -- 5%-- |
| 29 | 43 | "(Table 4)," should read --(Table 4);-- |
| 29 | 66 | "RAR (X)" should read --RARα)-- |
| 30 | 33 | after "GMB cells." delete "cl", insert a paragraph return and center "EXAMPLE 10" on the next line |
| 32 | 43 | "RXRS" should read --RXRs-- |
| 33 | 57 | "LRARα403 3SN" should read --LRARα403SN-- |
| 36 | 30 | "$P_{32}$" should read --$P^{32}$-- |
| 36 | 42 | "$\beta_{major}$" should read --$\beta^{major}$-- |

UNITED STATES PATENT AND TRADEMARK OFFICE
CERTIFICATE OF CORRECTION

PATENT NO. : 5,830,760  
DATED : November 3, 1998  
INVENTOR(S) : S. Tsai et al.

Page 5 of 5

It is certified that error appears in the above-identified patent and that said Letters Patent is hereby corrected as shown below:

| COLUMN | LINE | |
|---|---|---|
| 37 | 12 | "Chornienne" should read --Chomienne-- |
| 37 | 22 | "Coffinan" should read --Coffman-- |
| 37 | 60 | "429433" should read --429-433-- |
| 39 | 15 | "Mangelsdorfet al." should read --Mangelsdorf et al.-- |
| 39 | 16 | "Mangelsdorfetal." should read --Mangelsdorf et al.-- |

Signed and Sealed this

Thirteenth Day of March, 2001

Attest:

NICHOLAS P. GODICI

Attesting Officer     Acting Director of the United States Patent and Trademark Office